US010942187B2

United States Patent
Sato et al.

(10) Patent No.: US 10,942,187 B2
(45) Date of Patent: Mar. 9, 2021

(54) METHOD FOR QUANTIFYING AMINO ACID AND AMINO ACID QUANTIFICATION KIT

(71) Applicants: IKEDA FOOD RESEARCH CO., LTD., Fukuyama (JP); Hiroshima City University, Hiroshima (JP)

(72) Inventors: Daisuke Sato, Hiroshima (JP); Tomoko Nakatsuka, Hiroshima (JP); Hideyuki Aoki, Hiroshima (JP); Mikiko Kida, Hiroshima (JP); Kenta Yamada, Hiroshima (JP); Shoji Kaneko, Hiroshima (JP); Akimitsu Kugimiya, Hiroshima (JP)

(73) Assignees: IKEDA FOOD RESEARCH CO., LTD., Hiroshima (JP); HIROSHIMA CITY UNIVERSITY, Hiroshima (JP)

( * ) Notice: Subject to any disclaimer, the term of this patent is extended or adjusted under 35 U.S.C. 154(b) by 194 days.

(21) Appl. No.: 16/145,509

(22) Filed: Sep. 28, 2018

(65) Prior Publication Data
US 2019/0094235 A1    Mar. 28, 2019

Related U.S. Application Data

(63) Continuation-in-part of application No. PCT/JP2017/012511, filed on Mar. 28, 2017.

(30) Foreign Application Priority Data

Sep. 28, 2017 (JP) .............................. JP2017-187385

(51) Int. Cl.
G01N 33/68 (2006.01)
G01N 27/416 (2006.01)

(52) U.S. Cl.
CPC ..... G01N 33/6812 (2013.01); G01N 27/4168 (2013.01); G01N 33/6806 (2013.01)

(58) Field of Classification Search
CPC ............... G01N 27/4168; G01N 33/68; G01N 33/6806; G01N 33/6812
(Continued)

(56) References Cited

U.S. PATENT DOCUMENTS

| 6,846,638 B2 | 1/2005 | Shipwash |
| 2003/0229015 A1 | 12/2003 | Fogelman et al. |
| 2014/0357524 A1 | 12/2014 | Asano et al. |

FOREIGN PATENT DOCUMENTS

| JP | 2000-69990 | 3/2000 |
| JP | 3135649 | 2/2001 |

(Continued)

OTHER PUBLICATIONS

Nakatsuka et al. Bioscience, Biotechnology, and Biochemistry, vol. 83, No. 9, 2019, pp. 1616-1623.*

(Continued)

*Primary Examiner* — Maureen Wallenhorst
(74) *Attorney, Agent, or Firm* — Wenderoth, Lind & Ponack LL..P.

(57) ABSTRACT

A method for selectively and easily quantifying the L-form and/or D-form amino acids to be measured using an aminoacyl tRNA synthetase (AARS) with high sensitivity, and an amino acid quantification kit. A method for quantifying amino acids (L-AA and/or D-AA) in a sample using an AARS, wherein the amino acids and the AARS are released from an aminoacyl AMP-AARS complex once formed, and they are used again for forming the aminoacyl AMP-AARS complex, so that reaction products such as pyrophosphoric acid to be measured can be ultimately produced up to a molar number larger than that of the amino acids contained in the sample, and an amino acid quantification kit for performing the method.

10 Claims, 34 Drawing Sheets
Specification includes a Sequence Listing.

(58) Field of Classification Search
USPC .............. 436/86, 89, 79, 84, 111, 149, 164
See application file for complete search history.

(56) References Cited

FOREIGN PATENT DOCUMENTS

| JP | 2006-166709 | 6/2006 |
|---|---|---|
| JP | 2006-246841 | 9/2006 |
| JP | 2011-50357 | 3/2011 |
| JP | 2013-146264 | 8/2013 |
| JP | 5305208 | 10/2013 |

OTHER PUBLICATIONS

International Search Report issued in International Application No. PCT/JP2017/012511 dated May 23, 2017.
"Kagaku to Seibutsu (Chemistry and Organisms)", vol. 53, p. 192-197, Japan 2015.
Anne Norris et al., "Transfer Ribonucleic Acid-induced Hydrolysis of Valyaldenylate Bound to Isoleucyl Ribonucleic Acid Synthetase", J. Biol. Chem, vol. 241, No. 4, Feb. 25, 1966.
Emiko Uchikawa and Michiko Konno, "An Insight into the Mechanism of Enzymatic Reaction on Aminoacyl-tRNA Synthetases", Journal of the Crystallographic Society of Japan, vol. 52, p. 125-132, Japan, 2010.
Akimitsu Kugimiya et al., "A luminol chemiluminescence method for sensing histidine and lysine using enzyme reactions", Anal Biochem. Dec. 1, 2013; 443(1) 22-26.
Akimitsu Kugimiya et al, "Microfluidic Analysis of Serine Levels Using Seryl-tRNA Synthetase Coupled with Spectrophotometric Detection", Appl Biochem Biotechnol (2014) 174, 2527-2536.
Akimitsu Kugimiya et al., "Amino Acid Sensing Using an Ion-Sensitive Field-Effect Transistor", J. Chem. Chem. Eng. 6 (2012) 397-400.
Akemi Sasanuma et al., "Synthesis of Ap$_4$A, a "Signal Molecule" in vivo by Aminoacyl-tRNA Synthetases and Analyses of the Related Nucleotides by High-Performance Liquid Chromatographies", Journal of Tokyo Medical University, vol. 51, p. 469-480, Japan, 1993.
Hiroshi Nakajima et al., "Facile and Selective Synthesis of Diadenosine Polyphosphates through Catalysis by Leucyl t-RNA Synthetase Coupled with ATP Regeneration", Agric. Biol. Chem., 53(3), 615-623, 1989.
Toshimitsu Takayama et al., "Esterification of *Eschericia coli* tRNAs with D-Histidine and D-Lysine by Aminoacyl-tRNA Synthetases", Biosci. Biotechnol. Biochem., 69(5), 1040-1041, 2005.
Masafumi Kameya et al., "Application of aminoacyl-tRNA synthetase for selective determination of amino acids", Active Enzyme Molecule 2014, Proceedings 200-201.
Joanne M. Ravel et al., "Glutamyl and Glutaminyl Ribonucleic Acid Synthestaes of *Escherichia coli* W", J. Biol. Chem. 1965, 240:432-438.
Josée Charlier et al., "Arginyl-tRNA Synthetase from *Escherichia coli*", Eur. J. Biochem. 70, 137-145(1976).
Chris D. Forbes et al., "A high-throughput competitive scintillation proximity aminoacyl-tRNA synthetase charging assay to measure amino acid concentration", Anal. Biochem. Apr. 15, 2007; 363(2)246-254.
Akimitsu Kugimiya et al., "Amino acid sensing using aminoacyl-tRNA synthetase", Anal. Biochem 378(2008) 90-92.
Akimitsu Kugimiya et al., "Chemiluminescence Detection of Serine, Proline, Glycine, Asparagine, Leucine, and Histidine by Using Corresponding Aminoacyl-tRNA Synthetases as Recognition Elements", Appl Biochem Biotechnol (2015) 176:1195-1202.
Akimitsu Kugimiya et al., "Spectrophotometric detection of histidine and lysine using combined enzymatic reactions", Materials Science and Engineering C 33 (2013) 4867-4870.
Flow Analysis of Amino Acids by Using a Newly Developed Aminoacyl-tRNA Synthetase-Immobilized, Small Reactor Column-Based Assay, Appl Biochem Biotechnol (2016) 178:924-931.
Voet's Biochemistry (Second volume), Japan, 3rd edition, 1024-1029.
Web page of Hiroshima City University [searched on Jan. 13, 2016], Internet (URL: http://rsw.office.hiroshima-cu.ac.jp/Profiles/2/000129/profile.html).
Extended European Search Report dated Jan. 13, 2020 in European Patent Application No. 17775006.4.
Forbes et al., "A high-throughput competitive scintillation proximity aminoacyl-tRNA synthetase charging assay to measure amino acid concentration", Analytical Biochemistry, 2007, vol. 363, No. 2, pp. 246-254.

\* cited by examiner

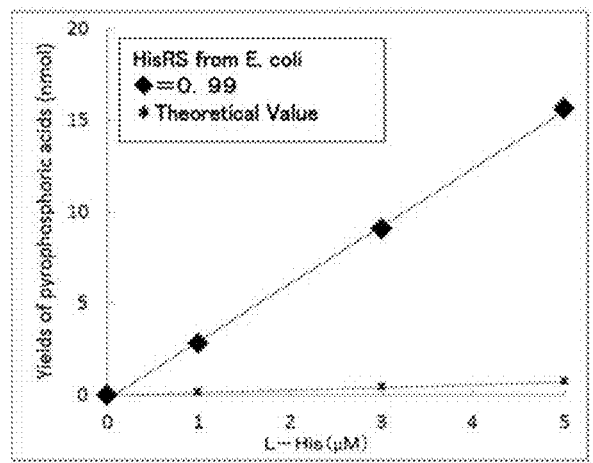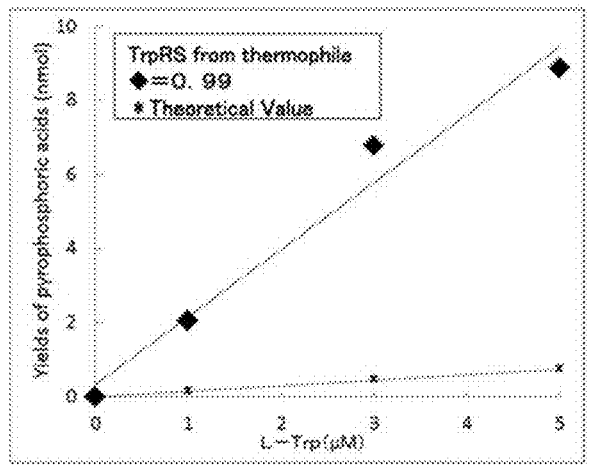

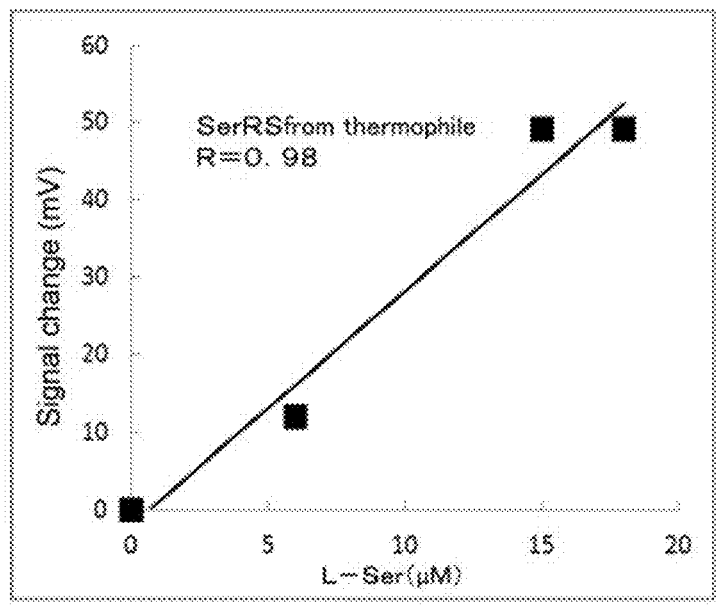

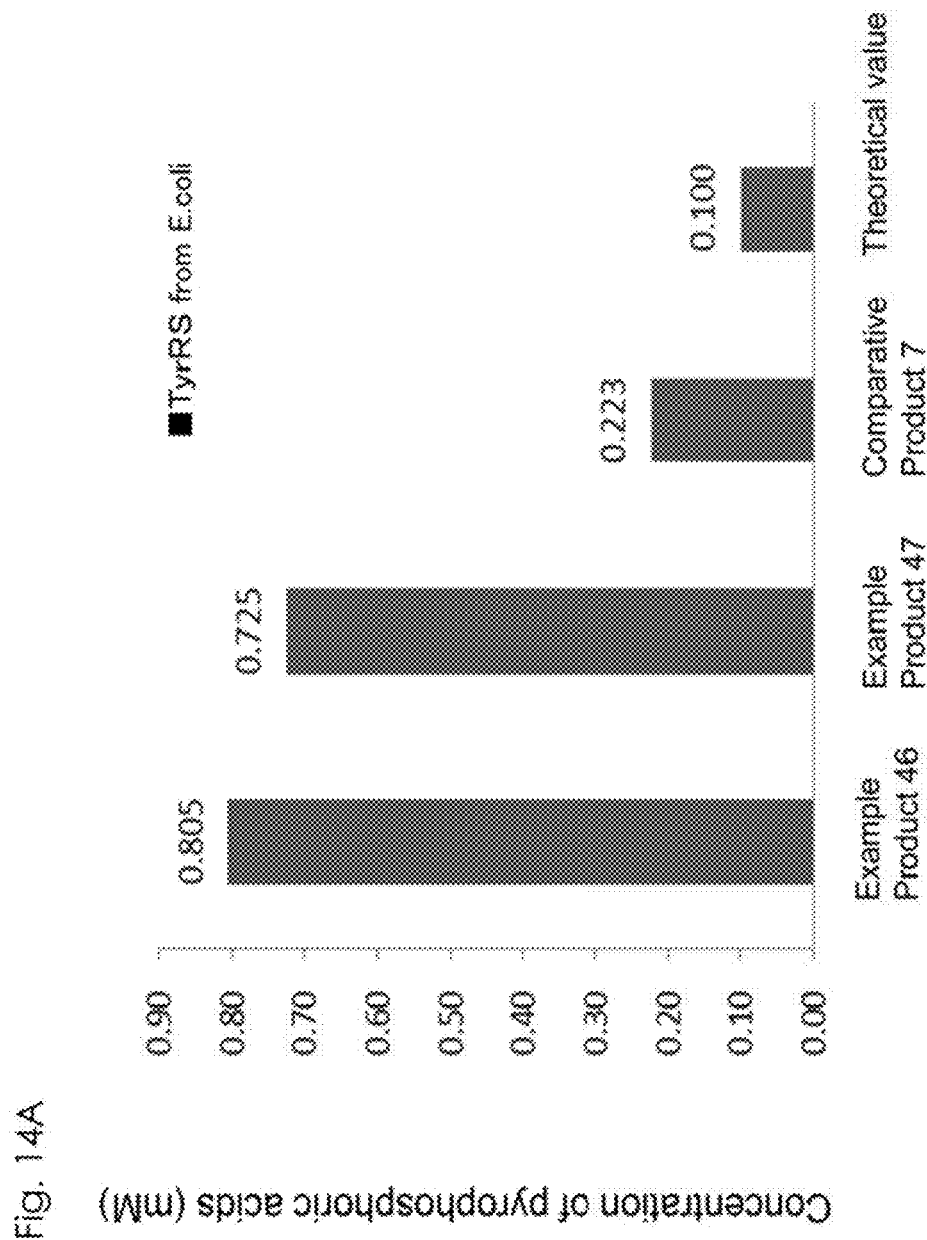

METHOD FOR QUANTIFYING AMINO ACID AND AMINO ACID QUANTIFICATION KIT

TECHNICAL FIELD

The present invention relates to a method for quantifying amino acids and an amino acid quantification kit.

BACKGROUND ART

L-amino acids (L-AA) play important roles as constituent components of proteins in living bodies and include 20 types. There have been many researches on the functionality of the L-amino acids, and the L-amino acids have been used in various industries of pharmaceuticals, processed foods, health foods and the like. For example, a free L-amino acid in a food is related to taste, scent after heating, preservability, biological control function after ingestion, etc., and has attracted attention as an important factor in fields of food science and nutritional science. Also, in recent years, it has been found that a blood level of the L-amino acid changes due to diseases, and the L-amino acid has also been utilized as a biomarker allowing diagnosis of cancers such as lung cancer, stomach cancer and colon cancer by measuring the blood level of the L-amino acid.

Also, amino acids include D-amino acids (D-AA), which are optical isomers of L-amino acids, including 19 types. Although D-amino acids are present in living bodies, their physiological functions have not been clearly understood. However, in recent years, D-amino acids have become analyzable by advancement of analytical techniques, and for example, it has been found that D-serines are increased in brains and spinal cords of Alzheimer's disease patients, that D-aspartic acids decrease in association with skin aging, and that D-alanines are involved in sweetness of crab and shrimp, etc. Thus, the physiological functions of D-amino acids have attracted attention. For this reason, the techniques for quantifying the L-form and D-form amino acids are indispensable techniques in various fields of product development, quality control, diagnosis, etc. using amino acids.

As an amino acid quantification technique for L-amino acids, a method wherein amino acids are separated by liquid chromatography and detected by color reaction with ninhydrin or a fluorescent derivatizing agent orthophthalaldehyde, is known. In addition, as amino acid quantification techniques for D-amino acids, a diastereomer method wherein D-amino acids are subjected to diastereomer fluorescence derivatization by adding a fluorescent derivatizing agent orthophthalaldehyde and a chiral derivatizing agent N-acyl-L-cysteine and analyzed by liquid chromatography, and a two-dimensional liquid chromatography method, are known (Non-Patent Document 1). However, the methods have had a problem that an analysis period is long because it takes about two hours to analyze one specimen, and the methods are unsuitable for measuring a large number of specimens.

As other amino acid quantification techniques, amino acid-measuring methods using enzymes capable of acting on L-amino acids and D-amino acids are known (Patent Document 1, Non-Patent Document 1). However, the methods have had problems that selectivity for an amino acid as a target substrate is low, the enzyme also reacts with amino acids other than the target, and there is no enzyme corresponding to 20 amino acids (19 amino acids in the case of D-amino acid).

An aminoacyl tRNA synthetase (AARS) is an enzyme related to protein synthesis in a living body and produces an aminoacyl tRNA in accordance with the following reaction formulas 1 and 2. There are 20 types of AARSs specific to 20 types of L-amino acids (L-AA). For this reason, the AARS is considered to be an enzyme with extremely high selectivity for targeted amino acids and tRNAs.

[Formula 1]

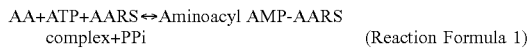
(Reaction Formula 1)

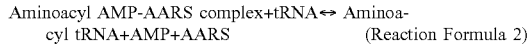
(Reaction Formula 2)

In this reaction, pyrophosphoric acid (PPi) is produced, and at the same time, each one molecule of adenosine triphosphate (ATP) and L-amino acid (L-AA) acts on the AARS to form a reaction intermediate called an aminoacyl adenylate (aminoacyl AMP)-AARS complex. Normally, the aminoacyl AMP strongly binds to the AARS in the complex, and thus it is considered that the above-described AARS reaction does not proceed unless the complex is decomposed by adding a tRNA or a nucleophile (an amine) (Patent Document 2, Non-Patent Documents 2 to 3). In addition, it is known when a large amount of pyrophosphoric acid is produced in Reaction Formula 1 of the reaction, the aminoacyl AMP-AARS complex is decomposed by pyrophosphoric acid as a reverse reaction of Reaction Formula 1, and an ATP-PPi exchange reaction producing the amino acid, the AARS and the ATP is caused (Non-Patent Document 4).

Quantification techniques for the L-amino acid using such an AARS-related reaction (AARS reaction) have been developed so far. For example, Patent Document 3 describes an amino acid analysis method based on the reaction represented by the following Reaction Formula 3.

(Reaction Formula 3)

[Formula 2]

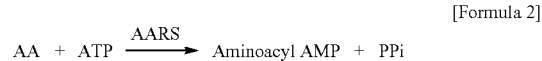

In this method, the L-amino acid is analyzed by using, as an index, pyrophosphoric acid generated while the AARS binds to the ATP and the L-amino acid. However, as can also be seen from Reaction Formula 3, since the AARS reacts with each one molecule of the L-amino acid and the ATP to produce one molecule of the aminoacyl AMP in this method, the pyrophosphoric acid is produced in only an amount equivalent to or smaller than the L-amino acid in the sample (Non-Patent Documents 5, 6, 7).

Furthermore, in Reaction Formula 3, it is expressed that the AARS functions as a catalyst and each one molecule of the ATP and the L-amino acid reacts with the AARS to produce the aminoacyl AMP and the pyrophosphoric acid, but Reaction Formula 2 does not proceed because the reaction system described in Patent Document 3 does not include the tRNA, and it is considered that the aminoacyl AMP-AARS complex is actually formed by Reaction Formula 1 (Paragraphs 0013 to 0016 in Patent Document 2). As a result, it is considered that only one molecule of the pyrophosphoric acid is produced from one molecule of the AARS. Thus, it is recognized that a large amount of AARS is required for allowing quantification of the L-amino acid contained in the sample by measuring the pyrophosphoric acid, not only from the above-described parts in Patent Document 2 but also by the inventors theirselves in Patent Document 3 (Paragraph 0046 in Patent Document 3, and Non-Patent Document 5).

As a result, since the amount of the produced pyrophosphoric acid is small relative to the L-amino acid, a quantitative range of the amino acid in the method is 300 to 900 µM by an ion-sensitive field effect transistor (ISFET) method and the amino acid can be quantified in a high concentration region, and meanwhile, in measurement of the amino acid in a low concentration region, the amino acid can be quantified in a range of 1 to 250 µM only by a high sensitive analysis through fluorometry using a multistep enzymatic reaction (Non-Patent Documents 6, 7, 8). However, the high sensitive analysis takes many costs. Furthermore, since pyrophosphoric acid is detected by the multistep enzymatic reaction, the high sensitive analysis is complicated and it is also concerned that each enzyme will be likely subject to external factors such as contaminants in blood.

Furthermore, the above Patent Document 2 describes an L-amino acid-quantifying method based on the AARS reaction of Reaction Formulas 1 and 2. That is, normally, the aminoacyl AMP tightly binds to the AARS to form an aminoacyl AMP-AARS complex, as described above. Thus, this method is characterized in that an amine (nucleophilic agent) such as hydroxylamine as an aminoacyl AMP-AARS complex-decomposing reagent is added so that the AARS is returned to a reactable state, and as a result, the L-amino acid is quantified with a small amount of AARS. The quantitative range of the amino acid in the method is supposed to be 5 to 200 µM.

However, in the method described in Patent Document 2, the complex-decomposing reagent reacts with the L-amino acid of the complex to produce a compound (e.g. as described in paragraph 0037 in Patent Document 2, when hydroxylamine is used as the complex-decomposing reagent, "amino acid hydroxamate" is produced), thus the L-amino acid cannot be reused, and as a result, a pyrophosphoric acid as a product is obtained only in an amount equivalent to the L-amino acid in the sample (paragraph 0023 in Patent Document 2). Furthermore, since the pyrophosphoric acid produced by the AARS reaction is detected by a multistep enzyme reaction in the method, the method is complicated and it is concerned that each enzyme is susceptible to blood contaminants and other external factors.

As described above, there have been many problems to be solved in the prior art regarding the amino acid-quantifying method capable of selectively measuring 20 types of L-amino acids and 19 types of D-amino acids, and a more effective amino acid-quantifying method is required.

On the other hand, as another AARS reaction, e.g. reactions of the following Reaction Formulas 4 and 5 are known. In this reaction, each one molecule of the ATP and the L-amino acid acts on the AARS to form the aminoacyl AMP-AARS complex. Subsequently, ATP, GTP, etc. are made to act on the complex to synthesize and produce a diadenosine polyphosphate (ApnA) such as diadenosine tetraphosphate (Ap4A), an adenosine guanosine tetraphosphate (Ap4G), and the like, which are expected as pharmaceuticals and pharmaceutical raw materials (Patent Document 4, Patent Document 5, Non-Patent Document 9, Non-Patent Document 10).

[Formula 3]

AA+ATP+AARS→aminoacyl AMP-AARS
complex+PPi             (Reaction Formula 4)

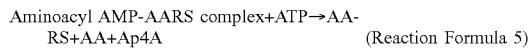
Aminoacyl AMP-AARS complex+ATP→AA-
RS+AA+Ap4A              (Reaction Formula 5)

These known documents describe that the synthetic ability of the ApnA varies depending on the type of the AARS, and e.g. a tryptophan of *Escherichia* and an AARS of arginine do not progress the reaction of Reaction Formula 5 and cannot synthesize the Ap4A. Additionally, in Reaction Formula 4 of the reaction, a reverse reaction is promoted in the presence of a pyrophosphoric acid, and the amino acid, the AARS and the ATP are produced from the aminoacyl AMP-AARS complex. For this reason, it is necessary to prevent occurrence of the reverse reaction in order to progress the reaction, and in the techniques described in the above known documents, an inorganic pyrophosphatase capable of decomposing a pyrophosphoric acid is used in order to decompose the pyrophosphoric acid produced in Reaction Formula 4.

Furthermore, the techniques described in these known documents absolutely relate to synthesis and production of ApnA, Ap4G etc. and are not intended to solve technical problems related to quantification of amino acids. Actually, in these known documents, there is no description on the quantification of amino acids utilizing the AARS reaction of the above Reaction Formulas 4 and 5, and no description on the reuse of the amino acid and the AARS caused in Reaction Formula 5.

AARS is known to include 20 types of AARSs specific to 20 types of L-amino acids. There is a report regarding some AARSs, wherein this AARS acts on D-amino acids (Non Patent Document 11). However, this document relates to an aspect that the AARS acts on the D-amino acid and transfers it to the tRNA, but is not intended to solve technical problems regarding the quantification of D-amino acids. In fact, in the document, there is no description on the quantification of D-amino acids utilizing the AARS reactions of the above Reaction Formulas 4 and 5, and no description on reuse of the D-amino acid and the AARS caused in Reaction Formula 5.

PRIOR ART DOCUMENTS

Patent Documents

Patent Document 1: Japanese Patent Application Laid-Open No. 2013-146264
Patent Document 2: JP Pat. No. 5305208
Patent Document 3: Japanese Patent Application Laid-Open No. 2011-50357
Patent Document 4: Japanese Patent Application Laid-Open No. 2000-69990
Patent Document 5: JP Pat. No. 3135649

Non-Patent Documents

Non-Patent Document 1: "Kagaku to Seibutsu (Chemistry and Organisms)", Vol. 53, p. 192-197, Japan, 2015
Non-Patent Document 2: "Voet's Biochemistry (Second volume)", Japan, 3rd edition, 1024-1029
Non-Patent Document 3: J. Biol. Chem., 241, 839-845, 1996
Non-Patent Document 4: "Journal of the Crystallographic Society of Japan", Vol. 52, p. 125-132, Japan, 2010
Non-Patent Document 5: Web page of Hiroshima City University [searched on Jan. 13, 2016], Internet (URL: http://rsw.office.hiroshima-cu.ac.jp/Profiles/2/000129/profile.html) [online], Akimitsu Kugimiya, majoring in creative science, Faculty of Information Sciences, Hiroshima City University
Non-Patent Document 6: Analytical Biochem., 443, 22-26, 2013
Non-Patent Document 7: Appl. Biochem. Biotechnol., 174, 2527-2536, 2014

Non-Patent Document 8: J. Chem. Eng. 6, 397-400, 2012
Non-Patent Document 9: "Journal of Tokyo Medical University", Vol. 51, p. 469-480, Japan, 1993
Non-Patent Document 10: Agric. Biol. Chem., 53, 615-623, 1989
Non-Patent Document 11: Biosci, Biotechnol. Biochem., 69, 1040-1041, 2005

SUMMARY OF INVENTION

Problem to be Solved

The objects of the present invention are to solve various problems in the above-described prior art regarding the method for quantifying L-form and D-form amino acids, and to provide a method for selectively and easily quantifying the L-form and/or D-form amino acids to be measured using an AARS in a short time, with high sensitivity and in a wide range of the amino acid concentration, and an amino acid quantification kit.

Solution to Problem

As a result of various investigations, the inventors have found that, in a method for quantifying amino acids (L-AA and/or D-AA) in a sample using an AARS, the AARS and the amino acids are released from an aminoacyl AMP-AARS complex once formed as shown in FIG. 1, and they are used again for forming the aminoacyl AMP-AARS complex, so that reaction products such as pyrophosphoric acid to be measured can be ultimately produced up to a molar number larger than that of the amino acids contained in the sample, and this finding has led to the completion of the invention.

The present invention relates to the following aspects of [1] to [7].

[1] A method for quantifying amino acids in a sample, which includes Step (I) including the following steps:
(Step I-1) a step including a reaction (Reaction 1) wherein L-form and/or D-form amino acids (L-AA and/or D-AA) in the sample, an aminoacyl tRNA synthetase (AARS) corresponding to the amino acids and an adenosine triphosphate (ATP) are reacted in the presence of a divalent ion or a polyamine to form a complex comprising an aminoacyl adenylate (aminoacyl AMP) and the AARS (aminoacyl AMP-AARS complex);
(Step I-2) a step including a reaction (Reaction 2) wherein an amino acid-regenerating agent acts on the aminoacyl AMP-AARS complex formed in Reaction 1 or Reaction 3 to release the AARS and the amino acids (L-AA and/or D-AA) from the complex;
(Step I-3) a step including a reaction (Reaction 3) wherein the amino acids (L-AA and/or D-AA) released in Reaction 2 and/or the AARS are reused in Reaction 1 to cause the aminoacyl AMP-AARS complex reaction; and
(Step I-4) a step of repeating Step I-2 and Step I-3, and Step (II) including measuring an amount of reaction products produced in Step (I) and determining an amount of the L-form and/or D-form amino acids on the basis of the measured amount of the reaction products.

[2] The method for quantifying amino acids according to [1], wherein an AARS concentration in a reaction solution of Step (I) is 5.3 μM or more.

[3] The method for quantifying amino acids according to [2], wherein the AARS concentration is in a range of 5.3 μM to 70 μM.

[4] The method for quantifying amino acids according to any one of [1] to [3], wherein the amino acid-regenerating agent used in Step (I) is a nucleotide and/or an alkaline compound.

[5] The method for quantifying amino acids according to any one of [1] to [4], wherein a polar solvent is added into the reaction solution of Step (I).

[6] The method for quantifying amino acids according to any one of [1] to [5], wherein an amino acid concentration in the sample is in a range of 300 μM to 1,000 μM.

[7] The method for quantifying amino acids according to any one of [1] to [6], wherein the amount of the reaction products produced in Step (I) is measured by measuring potential change by an ion-sensitive field effect transistor, a glass electrode or a multielectrode electrometer.

[8] The method for quantifying amino acids according to any one of [1] to [7], wherein the amount of the reaction products produced in Step (I) is measured by measuring change in absorbance in accordance with absorptiometry.

[9] The method for quantifying amino acids according to any one of [1] to [8], wherein at least one of a pyrophosphoric acid and hydrogen ion is measured as the reaction products produced in Step (I).

[10] The method for quantifying amino acids according to any one of [1] to [9], wherein the molar number of the reaction products produced in Step (I) is larger than that of the amino acids in the sample.

[11] The method for quantifying amino acids according to any one of [1] to [10], wherein either one of the L-form and D-form amino acids in the sample is removed as a pretreatment.

[12] An amino acid quantification kit for performing the amino acid-quantifying method according to any one of [1] to [11], which includes an ATP, an amino acid-regenerating agent, a divalent ion, a polyamine and an AARS corresponding to the amino acids, and/or a polar solvent.

Effects of Invention

In the amino acid-quantifying method according to the present invention, an AARS and amino acids (L-form and/or D-form amino acids) are released from a formed aminoacyl AMP-AARS complex, and they are repeatedly used for forming the aminoacyl AMP-AARS complex, so that reaction products such as pyrophosphoric acid to be measured can be produced up to a molar number larger than that of the amino acids contained in the sample. As a result, even when these reaction products are measured by a means simpler than the prior art, amino acids can be quantified in a short time and in a higher concentration range, for example, such as a range of 300 μM to 1,000 μM, than the amino acid quantification range in the amino acid-quantifying method which is the high sensitive analysis by fluorometry or the like using the multistep enzyme reaction in the prior art. In addition, when the same measuring means is used, amino acids can be quantified in a lower concentration range. Furthermore, both the L-form and D-form amino acids can be quantified. Additionally, after removing either one of the L-form and D-form amino acids, the remaining amino acid can also be measured by the AARS.

Consequently, the present invention can provide a method for selectively and easily quantifying amino acids to be measured using an AARS in a short time, with high sensitivity and in a wide concentration range such as that from as very low as 1 μM to as high as 300 μM-1,000 μM, and an amino acid quantification kit.

BRIEF DESCRIPTION OF DRAWINGS

FIGS. 9A-9D illustrate calibration curves for L-amino acids in pyrophosphoric acid measurement in accordance with a molybdenum blue method.

FIGS. 10A-10C illustrate calibration curves for L-amino acids in hydrogen ion concentration measurement by a cumulative ISFET electrode.

FIGS. 14A-14D illustrate comparison of yields of pyrophosphoric acids in the AARS reaction using L-amino acids between the present invention and under the condition of a low AARS concentration.

DESCRIPTION OF EMBODIMENTS

Figure 1:
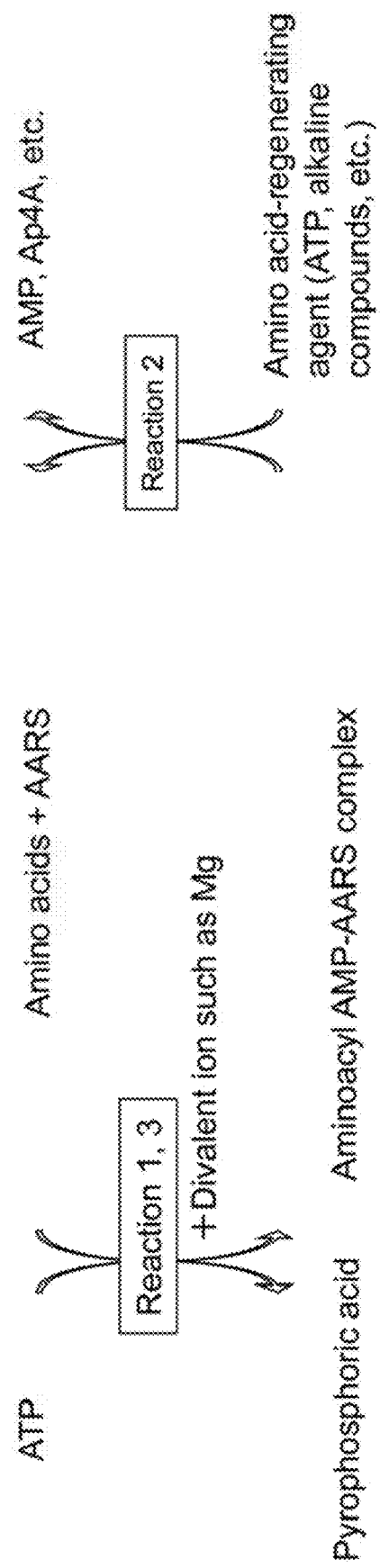
FIG. 1 illustrates reaction steps of the present invention.

In Reactions 1 and 3 in the method of the present invention, the amino acids, the AARS corresponding to the amino acids, and the ATP are reacted to form the aminoacyl AMP-AARS complex. For the AARS used in the method of the present invention, an AARS which specifically acts on 20 types of amino acids is used. For example, in the case of histidine (His), an AARS which specifically acts on histidine (HisRS) is used, in the case of serine (Ser), an AARS which specifically acts on serine (SerRS), in the case of tryptophan (Trp), an AARS which specifically acts on tryptophan (TrpRS) is used, and so on. In addition, the AARS used in the present invention may be any AARS as long as it is an AARS derived from an organism like an animal such as cattle, rat and mouse, a plant such as Lupin seed and *Phaseolus aurus*, and a microorganism such as *Escherichia*, *Thermus*, *Thermotoga* and *Saccharomyces*. Above all, the microorganism-derived AARS is preferred from the viewpoints of handling and productivity. Also, it may be a recombinant AARS or a synthesized AARS. Although it is preferably a soluble enzyme, it may be an insoluble enzyme combined with a surfactant, and may be an enzyme obtained by solubilizing an insoluble enzyme by fusion with a solubilized protein, deletion of a membrane-bound portion, or the like. The known amino acid sequence of the AARS can be used, and for the recombinant AARS, a protein having a sequence identity of 60%, 65%, 70%, 75%, 80%, 85%, 90%, 95% or higher and having an AARS activity may be used.

As the AARS prepared and used in the present invention, an AARS or the like obtained by any method/means known to those skilled in the art can be used, wherein e.g. an object containing the AARS is hydrogenated, pulverized by a pulverizer, an ultrasonic pulverizer or the like, then, from the pulverized product, solid matters are removed by centrifugation, filtration or the like to obtain an extract, and furthermore the extract is purified and isolated by column chromatography or the like. That is, a main technical feature of the present invention is that the AARS and the amino acids are released from the formed aminoacyl AMP-AARS complex, they are repeatedly used for forming the aminoacyl AMP-AARS complex, so that the reaction products such as a pyrophosphoric acid to be measured are produced up to a molar number larger than that of the amino acids contained in the sample, in the amino acid-quantifying method using the AARS. The method for preparing the AARS is not limited at all.

The sample used in the present invention is not particularly limited, and examples thereof include blood, fresh food, processed food and beverages. The amino acid concentration in each sample varies depending on each amino acid. For example, in relation to blood levels of the amino acids, the blood contains 11 to 44 nmol/mL of glutamic acid, 19 to 33 nmol/mL of methionine, 41 to 66 nmol/mL of tryptophan, 50 to 83 nmol/mL of tyrosine, 92 to 162 nmol/mL of serine, 68 to 97 nmol/mL of histidine, 119 to 257 nmol/ml of lysine, 488 to 733 nmol/ml of glutamine, 240 to 510 nmol/mL of alanine, and the like. In relation to contents of free amino acids in a fresh food, for example, a garlic contains 5 mg/100 g of lysine, 136 mg/100 g of arginine, 6 mg/100 g of serine, and the like. A tomato contains 94 mg/100 g of glutamine, 106 mg/100 g of proline, and the like. A dried shiitake mushroom contains 386 mg/100 g of glutamic acid, 268 mg/100 g of threonine, 46 mg/100 g of serine, and the like. Additionally, in relation to contents of L-form and D-form amino acids in a fruit, an apple contains 2071 µmol/L of L-form asparagine, 15 µmol/L of D-form asparagine, 105 µmol/L of L-form alanine and 3 µmol/L of D-form alanine, and a pineapple contains 3109 µmol/L of L-form asparagine, 25 µmol/L of D-form asparagine, 202 µmol/L of L-form valine, 2 µmol/L of D-form valine, and the like. In relation to contents of free amino acids in a processed food or a beverage, for example, Soy sauce contains 213 mg/100 g of lysine, 104 mg/100 g of histidine, 782 mg/100 g of glutamic acid, and the like. Green tea contains 107 mg/100 g of serine, 314 mg/100 g of arginine, 258 mg/100 g of glutamic acid, and the like. A fully ripened green robusta coffee bean contains 10 mg/100 g of lysine, 48 mg/100 g of histidine, 43 mg/100 g of serine, and the like. The sample is appropriately diluted and prepared depending on the expected concentrations of the amino acids in each of these samples, so that the sample can be used as the sample of the present invention.

The amino acids in the sample used in the present invention may include both L-form and D-form amino acids. In such a case, for example, it is preferred that either one of the L-form and D-form amino acids is removed as pretreatment in the method of the present invention. The method for removing either one of L-form and D-form amino acids can be exemplified by any method known to those skilled in the art, such as a method for removing either one of the L-form and D-form amino acids by column chromatography or an appropriate enzyme. Note that, although a biological sample contains both L-form and D-form amino acids, a ratio of most D-form amino acids in a mammalian body is about 0.1 to 1.0% of the L-form amino acids, and a ratio of the D-form amino acids in a fruit is 3.0% or less of the L-form amino acids, and thus the biological sample does not contain D-form amino acids so much as to affect the quantification of the L-form amino acids.

An AARS concentration in the reaction solution used for the reaction can be appropriately determined by a person skilled in the art depending on various reaction conditions such as the type of the sample, the estimated concentration of the amino acids in the sample, the ATP concentration and the reaction time/temperature. In order to suppress the reverse reaction in Reaction 1 of Step (I) as much as possible, it is preferred that the AARS concentration is increased when the amino acid concentration in the sample is expected to be low, and conversely, a low AARS concentration is allowed when the amino acid concentration in the sample is expected to be high. In addition, the reaction can be completed in a short time by increasing the AARS concentration, and conversely, when a long reaction time is allowed, a low AARS concentration is allowed. For example, a concentration of AARS derived from a microorganism such as *Escherichia*, *Thermus* and *Thermotoga* may be 0.05 µM or higher, more preferably 0.1 µM or higher, further preferably 0.5 µM or higher, particularly preferably 1.0 µM or higher, and most preferably 5.0 µM or higher. In any case, since the AARS is repeatedly used in the method of the present invention, the method has an advantage that there is no need to add an excessive amount of AARS to an expected amount of amino acid in the sample. Thus, the upper limit of the AARS concentration can be appropriately set by a person skilled in the art in consideration of economic efficiency and the like.

For example, when an amino acid in a high concentration range such as that of 300 µM to 1,000 µM is quantified, the AARS concentration is preferred to be 5.3 µM or higher. Specifically, the concentration of AARS derived from a microorganism such as *Escherichia*, *Thermus* and *Thermotoga* may be preferably 7.0 µM or higher, more preferably 10.0 µM or higher, further preferably 15.0 µM or higher, particularly preferably 50.0 µM or higher, and most preferably 70.0 µM or higher. Since the AARS is repeatedly used in the method of the present invention, the upper limit of the AARS concentration can be appropriately set by a person skilled in the art in consideration of economic efficiency and the like. Accordingly, the AARS concentration in the reaction solution may be in a range of 5.3 µM to 70 µM.

In Reaction 1 or Reaction 3 in the method of the present invention, ATP and divalent ions are used together with the AARS. For the ATP used in the present invention, a sodium salt, a lithium salt and the like can be used. The concentration of the ATP in the reaction solution used for the reaction can be appropriately determined by a person skilled in the art depending on various reaction conditions such as the type of the sample, the estimated amino acid concentration in the sample, the AARS concentration, the nucleotide concentration and the reaction time/temperature, but preferably the ATP is added in an amount excessive relative to the estimated amino acid concentration in the sample. For example, when the sample is blood, the ATP concentration may be 0.05 mM or higher, more preferably 0.1 mM or higher, further preferably 1.0 mM or higher, particularly preferably 5.0 mM or higher, most preferably 10.0 mM or higher. For example, when the amino acid in a high concentration range such as that of 300 µM to 1,000 µM is quantified, the ATP concentration may be preferably 25 mM or higher, more preferably 50 mM or higher, further preferably 150 mM or higher, most preferably 250 mM or higher. The upper limit of the ATP concentration can be appropriately set by a person skilled in the art in consideration of economic efficiency, equilibrium conditions of the reaction system and the like.

For the divalent ions used in the present invention, magnesium, manganese, cobalt, calcium, zinc and the like can be used. Since divalent ions have different requirements depending on the AARS, divalent ions suitable for the AARS to be used should be appropriately used, but it is more preferred to use magnesium or manganese which have common requirements for the AARS. Furthermore, polyamines such as spermine, spermidine and putrescine which have the same actions as of divalent ions can also be used. Although the concentration of the divalent ions in the reaction solution used for the reaction can be appropriately determined, it is preferred that the divalent ions are added in an amount equivalent to or larger than the ATP concentration. For example, a ratio of ATP:divalent ions in the AARS derived from a microorganism such as *Escherichia*, *Thermus* and *Thermotoga* may be at least 1:1, more preferably at least 1:3, even more preferably at least 1:5, particularly preferably at least 1:7, most preferably at least 1:10.

Subsequently, in Reaction 2 in the method of the present invention, the amino acid-regenerating agent acts on the aminoacyl AMP-AARS complex formed in Reaction 1 and Reaction 3 to decompose the complex, and the AARS and the amino acids are released from the complex. As the amino acid-regenerating agent used for the reaction can be used one arbitrarily selected from the nucleotides such as ATP, adenosine diphosphate (ADP), adenosine monophosphate (AMP), guanosine triphosphate (GTP), deoxyadenosine triphosphate (dATP) and the like, or a combination thereof, or alkaline compounds generating a hydroxide ion, such as sodium hydroxide, potassium hydroxide, sodium carbonate and the like. In Reaction 2, AMP, Ap4A, Ap3A, Ap4G, Ap3G, and the like are produced depending on the nucleotide to be used, at the same time of release of the AARS and the amino acids from the aminoacyl AMP-AARS complex. The concentration of the amino acid-regenerating agent in the reaction solution used for the reaction can be appropriately determined by a person skilled in the art depending on various reaction conditions such as the type of the sample, the estimated amino acid concentration in the sample, the AARS concentration, the ATP concentration and the reaction time/temperature. However, a sum of the nucleotides added in this Reaction and ATP used in Reaction 1 is preferably an amount excessive relative to the amino acid concentration in the sample, because the nucleotide is consumed in production of AMP, Ap4A, Ap3A, Ap4G, Ap3G and the like. For example, when the sample is blood, the nucleotide concentration may be 0.05 mM or higher, more preferably 0.1 mM or higher, further preferably 1.0 mM or higher, particularly preferably 5.0 mM or higher, most preferably 10.0 mM or higher. For example, when the amino acid in a high concentration range such as that of 300 μM to 1,000 μM is quantified, the nucleotide concentration may be preferably 25 mM or higher, more preferably 50 mM or higher, further preferably 150 mM or higher, most preferably 250 mM or higher. The upper limit of the nucleotide concentration can be appropriately set by a person skilled in the art in consideration of economic efficiency, equilibrium conditions of the reaction system and the like.

When the nucleotide is used as the amino acid-regenerating agent, the reaction pH may be any one for causing an AARS reaction with the amino acids in the sample. For example, in the cases of the AARSs of *Escherichia, Thermus* and *Thermotoga*, it may be preferably pH 4.0-10.0, more preferably pH 5.0-9.8, and most preferably pH 6.0-9.5. The reaction pH may be adjusted by means of any buffer known in the art. On the other hand, when the alkaline compound is used as the amino acid-regenerating agent, it will be enough to adjust the reaction system at pH 7 or higher. For example, in the cases of the AARSs of *Escherichia, Thermus* and *Thermotoga*, it may be preferably pH 7.0 or higher, more preferably pH 7.5 or higher, and most preferably pH 8.0 or higher. The reaction pH may be adjusted by means of any buffer known in the art such as HEPES buffer, CHES buffer, CAPS buffer, TRIS buffer, MOPS buffer and the like. Thus, in the method of the present invention, addition of the aminoacyl AMP-AARS complex-decomposing reagent such as an amine as described in Patent Document 2 is not required for returning the AARS to the reactable state, and since the released amino acid does not react with the reagent, it can be reused for forming the aminoacyl AMP-AARS complex.

In Reaction 3 in the method of the present invention, the amino acids and/or the AARS released in Reaction 2 is reused in Reaction 1, to cause the aminoacyl AMP-AARS complex reaction. Furthermore, in Step (I) in the method of the present invention, the ATP produced by reacting the pyrophosphoric acid produced in Reactions 1 and 3 and the AMP in the reaction system with phosphoenolpyruvic acid and pyruvate dikinase can be reused for formation of the aminoacyl AMP-AARS complex and release of the AARS and the amino acids from the complex, and/or an ADP produced by making the Ap4A pyrophosphohydrolase act on an Ap4A produced from the nucleotide in Reaction 2 can be reused as the nucleotide in Reaction 2, by any method known to those skilled in the art.

For example, when ATP is selected as the nucleotide that acts in Reaction 2 and ATP is not reproduced as mentioned above, it is preferable to add ATP at a higher concentration than a total of the above ATP and the nucleotide concentrations.

As a result, under reaction conditions such as compositions of the amino acid-regenarating agent (nucleotides such as ATP and/or the alkaline compound) and the AARS corresponding to the amino acids described above, molecules of each reaction product such as the pyrophosphoric acid and/or the hydrogen ions can be produced in a molar number larger than that of the amino acids to be measured in the sample, as a result of the reaction in Step (I). As a result, the amino acids can be quantified from an extremely low amino acid concentration of about 1 μM, which is lower than the concentration in the prior art, to an extremely high amino acid concentration of about 1 mM, which is higher than the concentration in the prior art, in the method of the present invention. Hence, it can be said that this point is a remarkable effect of the present invention as compared with the prior art.

However, even if the amount of the reaction products such as pyrophosphoric acid produced under the reaction conditions is not larger than the molar number of the amino acids in the sample, the reaction products such as pyrophosphoric acid need not be produced in a molar number larger than that of the amino acids as long as the amino acids can be quantified on the basis of the reaction products. Thus, the amounts of pyrophosphoric acid and hydrogen ions produced in Step (I) of the present invention are not particularly limited as long as the amino acids can be quantified by an appropriate method for measuring the reaction products in Step (II). Also, the repeat count of Reaction 2 (Step I-2) and Reaction 3 (Step I-3) in (Step I-4) in the method of the present invention is not particularly limited as long as the amino acid can be quantified by an appropriate method for measuring the reaction products in Step (II).

The reaction temperature in Step (I) in the method of the present invention may be any temperature for causing each reaction. For example, in the case of the AARS of *Escherichia*, the temperature is preferably 10 to 80° C., more preferably 20 to 70° C., most preferably 30 to 60° C. In the cases of the AARSs of *Thermus* and *Thermotoga*, the temperature is preferably 10 to 100° C., more preferably 30 to 98° C., most preferably 50 to 95° C. Also, the reaction time may be any period for causing an AARS reaction with the amino acids in the sample, but it is preferably about 1 to 90 minutes, more preferably about 5 to 60 minutes, further preferably about 10 to 30 minutes. Furthermore, when an amino acid in a high concentration range such as that of 300 μM to 1,000 μM is quantified, the temperature is preferably 30 sec. or more, more preferably 45 sec. or more, further preferably one minute or more, particularly preferably 5 minutes or more, most preferably 10 minutes or more.

It is possible to further increase the reaction products by adding (co-existing) of the polar solvent in the reaction system of Step (I) in the present method. The polar solvent includes any protic polar solvents known in the art such as glycerol and ethylene glycol; and an aprotic polar solvent such as dimethyl sulfoxide. The polar solvent concentration in the reaction solution to be used in the reaction can be appropriately set by a person skilled in the art in consideration of various reaction conditions such as a kind of the sample, a prospected concentration of an amino acid in the sample, AARS concentration, nucleotide concentration, reaction time and temperature. When the sample is blood, for example, the polar solvent concentration may be preferably 1-70% by weight, more preferably 5-60% by weight, most preferably 10-50% by weight.

Respective reaction components such as reagents and enzymes used in each step included in Step (I) in the method of the present invention can be added to the reaction system in accordance with any means, procedure and the like known to those skilled in the art, as long as the addition method can cause the AARS reaction. For example, respective components may be previously added to the reaction system at a time before starting the reaction, or alternatively the AARS or the amino acids may be finally added for reaction.

In Step (II) in the method of the present invention, each amount of each reaction product such as pyrophosphoric acid, adenosine monophosphate (AMP) and hydrogen ion produced in Step (I) is measured to determine an amount of the amino acid on the basis of the measured amount of the reaction product. Depending on the measurement method or the like, Step (II) can be appropriately carried out after the AARS reaction with the amino acids in the sample in Step (I) is terminated by any method/means known to those skilled in the art such as addition of trichloroacetic acid to the reaction system e.g. as described in Examples, or at any stage where the reaction progresses in Step (I).

For measuring the amount of pyrophosphoric acid produced in Step (I) of the present invention, any method/means known to those skilled in the art, e.g. enzyme methods capable of measuring pyrophosphoric acid, such as a molybdenum blue method wherein an absorbance of a blue complex produced by reacting molybdic acid with pyrophosphoric acid is measured, a method of combining a hypoxanthine-guanine phosphoribosyl transferase and a xanthine oxidase or a xanthine dehydrogenase, a method of measuring luminescence of a combined product of luminol with an inorganic pyrophosphatase, pyruvate oxidase and peroxidase, or the like can be used. Also, a measurement method of measuring a potential change by a multielectrode electrometer, wherein an oxidation-reduction reaction is caused by an enzyme reaction or the like, and a current value attributed to the oxidation-reduction reaction is detected, or the like can be used. Furthermore, for measuring hydrogen ions produced in the reaction, a measurement method of measuring a potential change by a glass electrode for detecting hydrogen ions or an ion-sensitive field effect transistor, or the like can be used. For measuring the adenosine monophosphate (AMP) produced by the reaction, measurement with an AMP sensor utilizing luminescence for detecting the adenosine monophosphate, or the like can be used. The pyrophosphoric acid, hydrogen ions, AMP, etc. produced in Step (I) of the present invention can be separated from the reaction solution and measured. Although the method for separating the pyrophosphoric acid, hydrogen ions, AMP, etc. from the reaction solution is not particularly limited as long as the method does not affect the measurement, examples of the method include protein removal by acid treatment, paper chromatography separation, separation by a microfluidic device, and the like. A main technical feature of the present invention is that, in the amino acid-quantifying method using AARS, the AARS and the amino acids are released from the formed aminoacyl AMP-AARS complex, and these compounds are repeatedly reused for formation of the complex to produce the reaction products such as pyrophosphoric acid to be measured up to a molar number larger than that of the amino acids contained in the sample, so that the amino acids can be quantified in such a wide range of from the low concentration of about 1 μM to the high concentration of about 1,000 μM. The method for measuring an amount of the reaction products is not limited at all.

The present invention provides an amino acid quantification kit for performing the above-described method of the present invention, which includes each component described above required for quantifying the amino acids in the sample. The kit may appropriately contain other optional components known to those skilled in the art such as a stabilizer and a buffer to enhance the stability of the reagent components such as an enzyme. Although the components are not particularly limited as long as they do not affect the measurement, they can be exemplified by bovine serum albumin (BSA), ovalbumin, saccharides, sugar alcohols, carboxyl group-containing compounds, an antioxidant, a surfactant, or amino acids having no activity with an enzyme, and the like. In addition, an example of the kit is a kit for measuring the above-described pyrophosphoric acid and hydrogen ions.

EXAMPLES

Hereinafter, the present invention will be specifically explained with reference to Examples, but the technical scope of the present invention is not limited by the following Examples.

Example 1

(Preparation of AARS Derived from Thermophiles)

An *E. coli* BL21 (DE3) pLys strain was transformed with a plasmid (pET28b) having AARS sequences derived from thermophile, and this was used as an expression strain. Each expression strain was cultured in a TB medium containing kanamycin and chloramphenicol as selection markers at 37° C., and after the OD600 reached about 0.6, IPTG was added so that its final concentration was 1 mM, and induction culture was carried out at 25° C. overnight. After completion of the culture, the bacteria were collected, and the obtained bacteria were crushed by sonication to prepare a cell-free extract. The prepared cell-free extract was subjected to heat treatment at 70° C. for 15 minutes and then centrifuged. The expression of the desired enzyme was confirmed by electrophoresis using a portion of the obtained supernatant. Subsequently, from the remaining supernatant, contaminant proteins were removed by a His tag column (trade name: TALON superflow, made by GE Healthcare) to obtain HisRS (SEQ ID NO:1), SerRS (SEQ ID NO:2), TrpRS (SEQ ID NO:3) derived from *Thermotoga maritima* MSB8 (NBRC100826, JCM10099, ATCC43589, DSM3109), and LysRS (SEQ ID NO:4) derived from *Thermus thermophilus* HB8 (NBRC101084, ATCC27634, DSM579, JCM10941, NCIMB 11244).

Example 2

(Preparation of AARS Derived from *E. coli*)

An *E. coli* BL21 (DE3) pLys strain was transformed with a plasmid (pET28b) having an AARS sequence derived from a variant of *E. coli* K12 (NBRC3992), and used as an expression strain. Each expression strain was cultured in a TB medium containing kanamycin and chloramphenicol as selection markers at 37° C., and after the OD600 reached about 0.6, IPTG was added so that its final concentration was 1 mM, and induction culture was carried out at 25° C. overnight. After completion of the culture, the bacteria were collected, and the obtained bacteria were crushed by sonication to prepare a cell-free extract. Furthermore, the extract was centrifuged, and the expression of the desired enzyme was confirmed by electrophoresis using a portion of the obtained supernatant. Subsequently, from the remaining supernatant, contaminant proteins were removed by a His tag column (trade name: TALON superflow, made by GE Healthcare) to obtain TyrRS (SEQ ID NO:5), ValRS (SEQ ID NO:6), TrpRS (SEQ ID NO:7), IleRS (SEQ ID NO:8), LysRS (SEQ ID NO:9), HisRS (SEQ ID NO:10), and SerRS (SEQ ID NO:11).

First Aspect of the Present Invention

Embodiments relating to quantification of the amino acid in a low concentration range of about 1 μM to 300 μM will be shown in the following Examples 3-43

(Yield of Pyrophosphoric Acid Depending on Concentrations of Various AARSs Using L-Amino Acids: Step (I) in the Method of the Present Invention)

Example 3

240 μL of a reaction solution containing 250 mM HEPES-KOH (pH 8), 31.3 mM ATP and 313 mM MgCl$_2$ was prepared, to which 30 μL of L-histidine was added so that its final concentration was 30 μM, and 30 μL of HisRS (derived from thermophile) was added so that its final concentration was 0.1 μM, and the solution was treated at 70° C. for 30 minutes. After the reaction, 60 μL of trichloroacetic acid was added so that its final concentration was 4%, to terminate the reaction. After the termination of the reaction, the precipitate was removed by centrifugation to prepare Example Product (inventive product) 1.

Example 4

240 μL of a reaction solution containing 250 mM HEPES-KOH (pH 8), 31.3 mM ATP and 313 mM $MgCl_2$ was prepared, to which 30 μL of L-histidine was added so that its final concentration was 30 μM, and 30 μL of HisRS (derived from E. coli) was added so that its final concentration was 0.12 μM, 0.17 μM or 0.21 μM, and the solution was treated at 50° C. for 30 minutes. After the reaction, 60 μL of trichloroacetic acid was added so that its final concentration was 4%, to terminate the reaction. After the termination of the reaction, the precipitate was removed by centrifugation to prepare Example Products 2, 3 and 4.

Example 5

240 μL of a reaction solution containing 250 mM HEPES-KOH (pH 8), 31.3 mM ATP and 313 mM $MgCl_2$ was prepared, to which 30 μL of L-serine was added so that its final concentration was 30 μM, and 30 μL of SerRS (derived from thermophile) was added so that its final concentration was 0.05 μM, 0.075 μM or 0.1 μM, and the solution was treated at 70° C. for 30 minutes. After the reaction, 60 μL of trichloroacetic acid was added so that its final concentration was 4%, to terminate the reaction. After the termination of the reaction, the precipitate was removed by centrifugation to prepare Example Products 5, 6 and 7.

Example 6

240 μL of a reaction solution containing 250 mM HEPES-KOH (pH 8), 31.3 mM ATP and 313 mM $MgCl_2$ was prepared, to which 30 μL of L-serine was added so that its final concentration was 30 μM, and 30 μL of SerRS (derived from E. coli) was added so that its final concentration was 0.12 μM, 0.17 μM or 0.21 μM, and the solution was treated at 50° C. for 30 minutes. After the reaction, 60 μL of trichloroacetic acid was added so that its final concentration was 4%, to terminate the reaction. After the termination of the reaction, the precipitate was removed by centrifugation to prepare Example Products 8, 9 and 10.
(Measurement of Pyrophosphoric Acid in Accordance with Molybdenum Blue Method: Step (II) in the Method of the Present Invention)

Example 7

Figure 2:
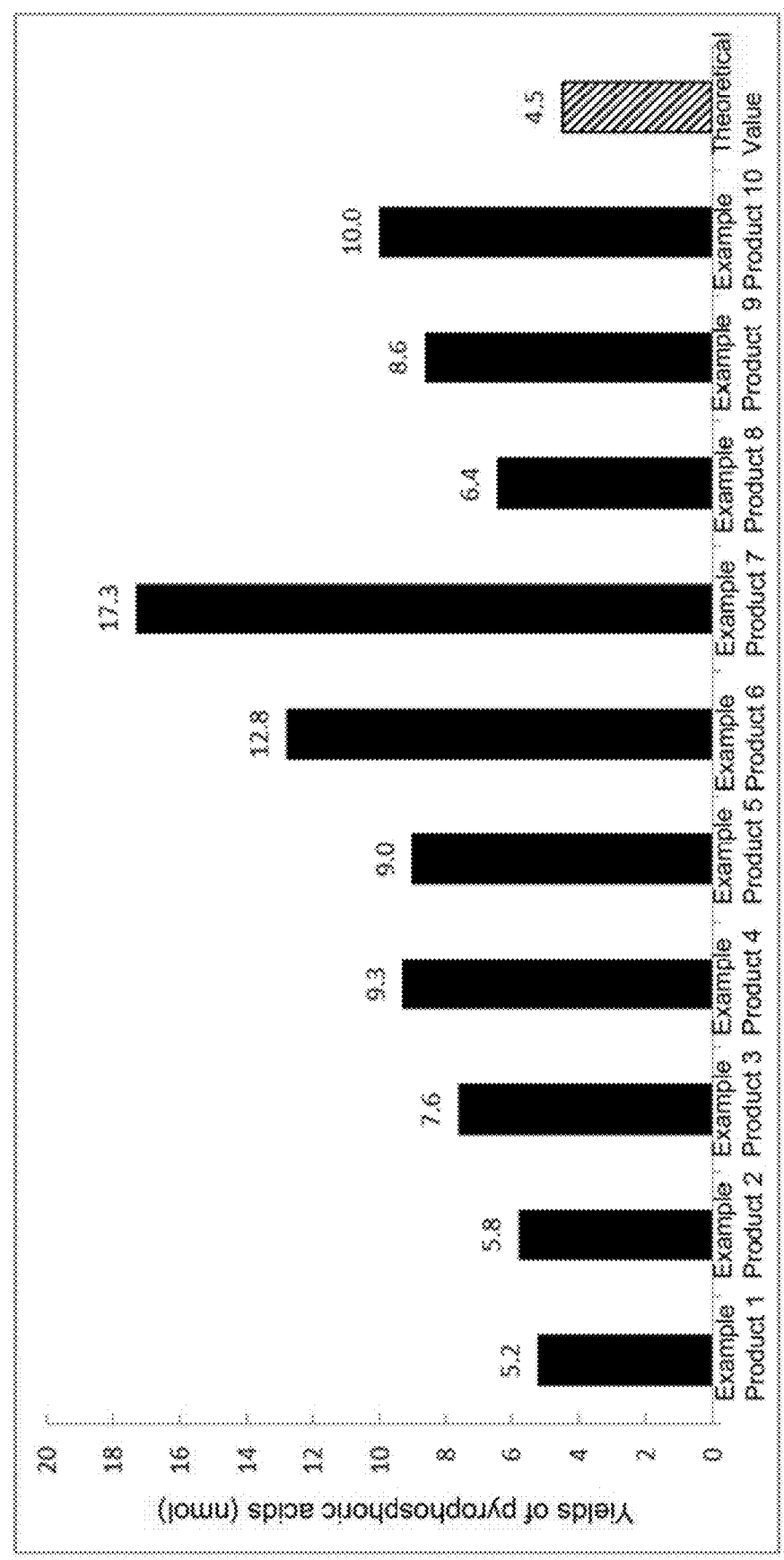
FIG. 2 illustrates yields of pyrophosphoric acids depending on concentrations of various AARSs using L-amino acids.

15 μL of 1 M mercaptoethanol and 60 μL of color developing liquid (2.5% ammonium molybdate/5 N sulfuric acid) were mixed in 150 μL of a reaction solution of each of the prepared Example Products 1 to 10, the solution was allowed to stand at room temperature for 20 minutes, and then an absorbance at 580 nm was measured. The pyrophosphoric acid amount in the reaction solution was determined from the volume of the solution and a pyrophosphoric acid concentration obtained by subtracting the absorbance value of each sample to which water was added instead of the L-amino acid as a blank from the absorbance value of the respective sample. As a result, as shown in FIG. 2, the pyrophosphoric acid was produced in an amount larger than the theoretical value of the pyrophosphoric acid amount produced when all of the added amino acids were used in the enzyme reaction. Thus, it was revealed that the pyrophosphoric acid could be produced in a molar number larger than the molecular number of the amino acids contained in the sample in accordance with the method of the present invention.
(Yield of Pyrophosphoric Acid Depending on Concentrations of Various ATPs Using L-Amino Acids: Step (I) in the Method of the Present Invention)

Example 8

240 μL of a reaction solution containing 250 mM HEPES-KOH (pH 8), 6.3 mM ATP and 63.5 mM $MgCl_2$, as well as 240 μL of a reaction solution containing 250 mM HEPES-KOH (pH 8), 31.3 mM ATP and 313 mM $MgCl_2$ were prepared, and to each of the solutions, 30 μL of L-histidine was added so that its final concentration was 30 μM, and 30 μL of HisRS (derived from thermophile) was added so that its final concentration was 5 μM, and the solution was treated at 70° C. for 15 minutes. After the reaction, 60 μL of trichloroacetic acid was added so that its final concentration was 4%, to terminate the reaction. After the termination of the reaction, the precipitate was removed by centrifugation to prepare Example Products 11 and 12.

Example 9

240 μL of a reaction solution containing 250 mM HEPES-KOH (pH 8), 12.5 mM ATP and 125 mM $MgCl_2$, as well as 240 μL of a reaction solution containing 250 mM HEPES-KOH (pH 8), 31.3 mM ATP and 313 mM $MgCl_2$ were prepared, and to each of the solutions, 30 μL of L-tyrosine was added so that its final concentration was 30 μM, and 30 μL of TyrRS (derived from E. coli) was added so that its final concentration was 5 μM, and the solution was treated at 50° C. for 30 minutes. After the reaction, 60 μL of trichloroacetic acid was added so that its final concentration was 4%, to terminate the reaction. After the termination of the reaction, the precipitate was removed by centrifugation to prepare Example Products 13 and 14.
(Measurement of Pyrophosphoric Acid in Accordance with Molybdenum Blue Method: Step (II) in the Method of the Present Invention)

Example 10

Figure 3:
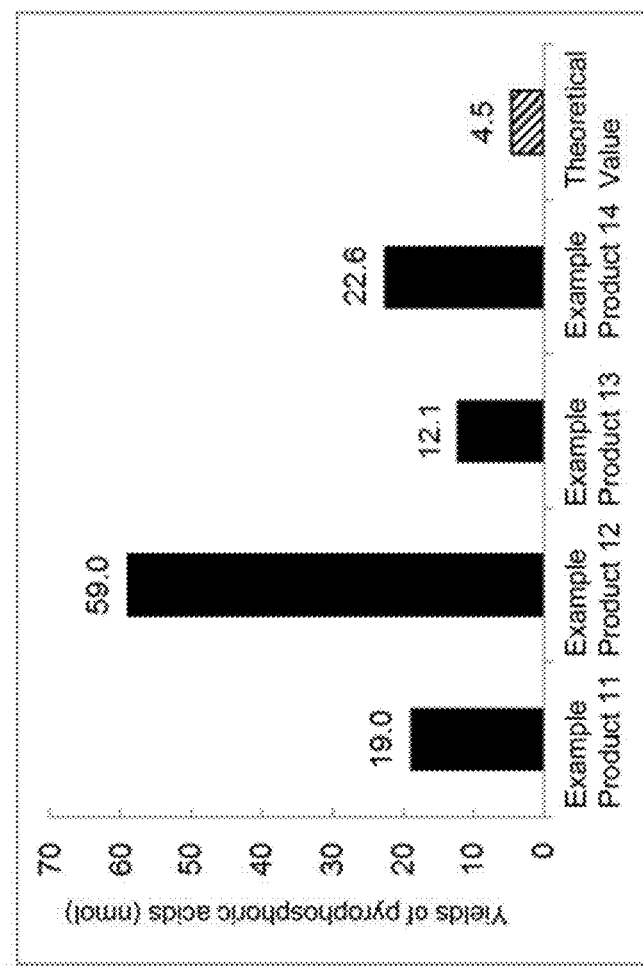
FIG. 3 illustrates yields of pyrophosphoric acids depending on various ATP concentrations in various AARSs using L-amino acids.
Figure 4A:
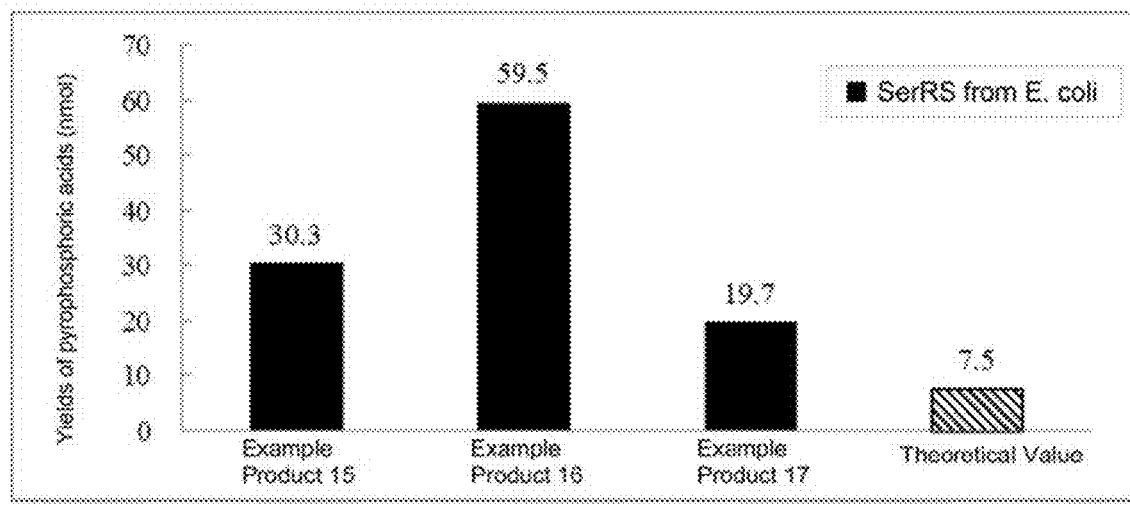
FIGS. 4A-4D illustrate yields of pyrophosphoric acids depending on various divalent ions in various AARSs using L-amino acids.
Figure 4B:
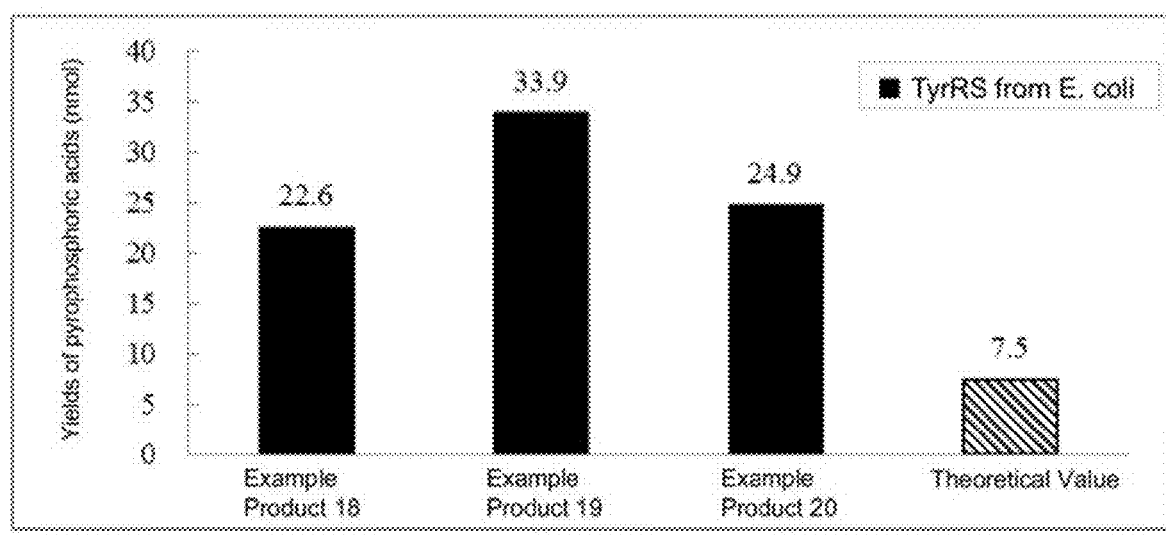
Figure 4C:
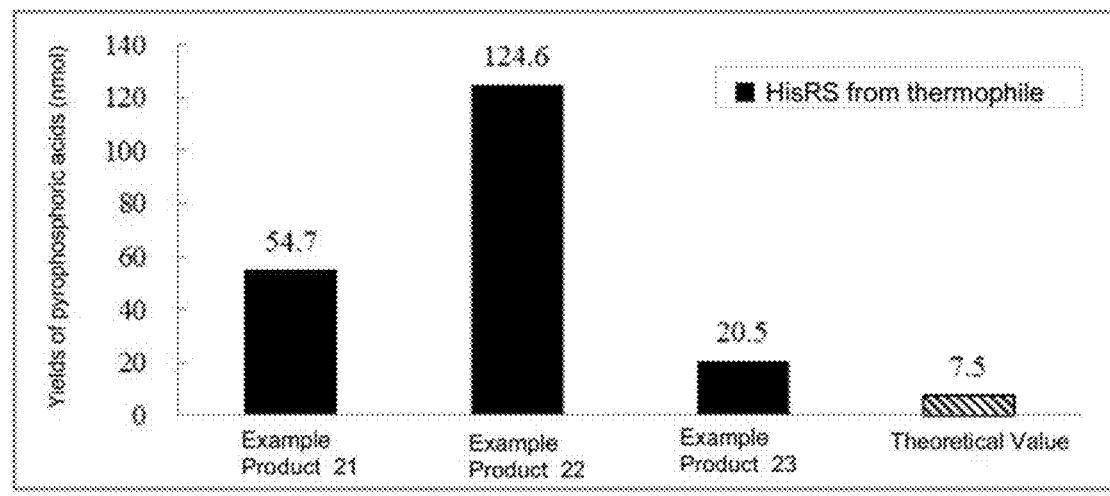
Figure 4D:
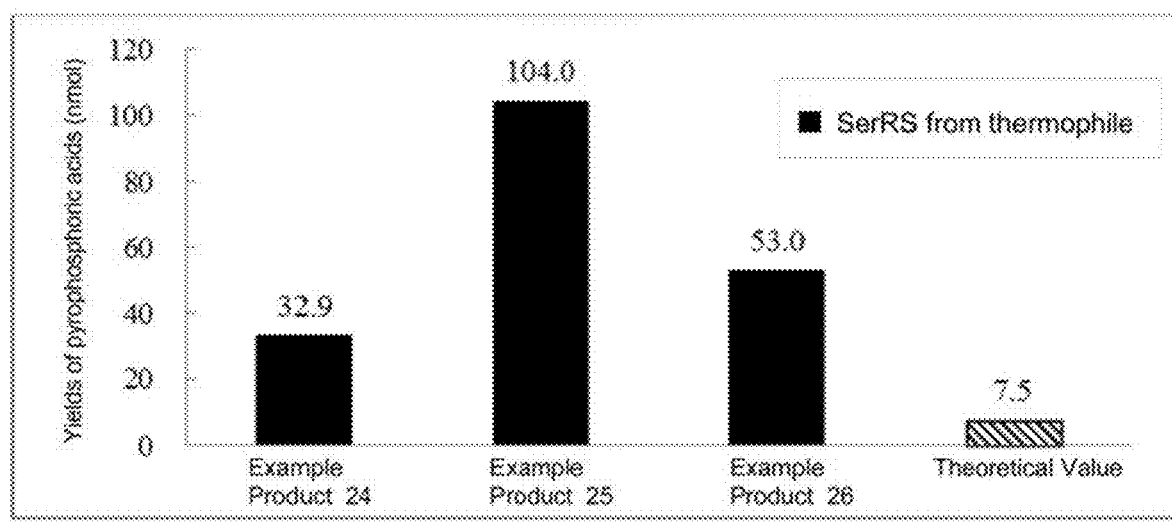

The prepared pyrophosphoric acids of Example Products 11 to 14 were measured in accordance with the molybdenum blue method described in Example 7. As a result, there was a tendency that the pyrophosphoric acid increased as the ATP concentration increased, as shown in FIG. 3. In addition, the pyrophosphoric acid was produced in an amount larger than the theoretical value of the pyrophosphoric acid amount produced when all of the added amino acids were used in the enzyme reaction. Thus, it was shown that the pyrophosphoric acid could be produced in a molar number larger than the molecular number of the amino acids contained in the sample in accordance with the method of the present invention.
(Yield of Pyrophosphoric Acid Depending on Various Divalent Ions in Various AARSs Using L-Amino Acids: Step (I) in the Method of the Present Invention)

Example 11

240 μL of reaction solutions respectively containing 250 mM HEPES-KOH (pH 8), 31.3 mM ATP and 31.3 mM $MgCl_2$ or $MnCl_2$ or $CoCl_2$ were prepared, and to each solution, 30 μL of L-serine was added so that its final concentration was 30 μM, and 30 μL of SerRS (derived from *E. coli*) was added so that its final concentration was 5 μM, and the solution was treated at 50° C. for 30 minutes. After the reaction, 60 μL of trichloroacetic acid was added so that its final concentration was 4%, to terminate the reaction. After the termination of the reaction, the precipitate was removed by centrifugation to prepare Example Products 15 to 17.

Example 12

240 μL of reaction solutions containing 250 mM HEPES-KOH (pH 8), 31.3 mM ATP and 31.3 mM $MgCl_2$ or $MnCl_2$ or $CoCl_2$ were prepared, and to each solution, 30 μL of L-tyrosine was added so that its final concentration was 30 μM, and 30 μL of TyrRS (derived from *E. coli*) was added so that its final concentration was 5 μM, and the solution was treated at 50° C. for 30 minutes. After the reaction, 60 μL of trichloroacetic acid was added so that its final concentration was 4%, to terminate the reaction. After the termination of the reaction, the precipitate was removed by centrifugation to prepare Example Products 18 to 20.

Example 13

240 μL of reaction solutions containing 250 mM HEPES-KOH (pH 8), 31.3 mM ATP and 31.3 mM $MgCl_2$ or $MnCl_2$ or $CoCl_2$ were prepared, and to each solution, 30 μL of L-histidine was added so that its final concentration was 30 μM, and 30 μL of HisRS (derived from thermophile) was added so that its final concentration was 5 μM, and the solution was treated at 70° C. for 30 minutes. After the reaction, 60 μL of trichloroacetic acid was added so that its final concentration was 4%, to terminate the reaction. After the termination of the reaction, the precipitate was removed by centrifugation to prepare Example Products 21 to 23.

Example 14

240 μL of reaction solutions containing 250 mM HEPES-KOH (pH 8), 31.3 mM ATP and 31.3 mM $MgCl_2$ or $MnCl_2$ or $CoCl_2$ were prepared, and to each solution, 30 μL of L-serine was added so that its final concentration was 30 μM, and 30 μL of SerRS (derived from thermophile) was added so that its final concentration was 5 μM, and the solution was treated at 70° C. for 30 minutes. After the reaction, 60 μL of trichloroacetic acid was added so that its final concentration was 4%, to terminate the reaction. After the termination of the reaction, the precipitate was removed by centrifugation to prepare Example Products 24 to 26.

(Measurement of Pyrophosphoric Acid in Accordance with Molybdenum Blue Method: Step (II) in the Method of the Present Invention)

Example 15

The Example Products 15 to 26 prepared in Examples 11 to 14 were measured in accordance with the molybdenum blue method described in Example 7. The result indicated that, among the same AARSs, the yield of the pyrophosphoric acid varied depending on the type of the bivalent cation, as shown in FIGS. 4A-4D. In addition, it was indicated that although the influence of the divalent ion on the yield of the pyrophosphoric acid also varied depending on the type of the AARS, Mg and Mn were optimum divalent ions commonly having for the AARSs.

(Yield of Pyrophosphoric Acid Depending on Various Nucleotides in Various AARSs Using L-Amino Acids: Step (I) in the Method of the Present Invention)

Example 16

240 μL of a reaction solution containing 250 mM HEPES-KOH (pH 8), 31.3 mM ATP and 31.3 mM $MgCl_2$, or 240 μL of a reaction solution containing 250 mM HEPES-KOH (pH 8), 31.3 mM ATP, 31.3 mM ADP and 313 mM $MgCl_2$, or 240 μL of a reaction solution containing 250 mM HEPES-KOH (pH 8), 31.3 mM ATP, 31.3 mM AMP and 313 mM $MgCl_2$ was prepared, and to each solution, 30 μL of L-tryptophan was added so that its final concentration was 50 μM, and 30 μL of TrpRS (derived from *E. coli*) was added so that its final concentration was 5 μM, and the solution was treated at 50° C. for 30 minutes. After the reaction, 60 μL of trichloroacetic acid was added so that its final concentration was 4%, to terminate the reaction. After the termination of the reaction, the precipitate was removed by centrifugation to prepare Example Products 27 to 29.

Example 17

240 μL of a reaction solution containing 250 mM HEPES-KOH (pH 8), 31.3 mM ATP and 313 mM $MgCl_2$, or 240 μL of a reaction solution containing 250 mM HEPES-KOH (pH 8), 31.3 mM ATP, 31.3 mM ADP and 313 mM $MgCl_2$ was prepared, and to each solutions, 30 μL of L-histidine was added so that its final concentration was 50 μM, and 30 μL of HisRS (derived from *E. coli*) was added so that its final concentration was 5 μM, and the solution was treated at 50° C. for 30 minutes. After the reaction, 60 μL of trichloroacetic acid was added so that its final concentration was 4%, to terminate the reaction. After the termination of the reaction, the precipitate was removed by centrifugation to prepare Example Products 30 and 31.

Example 18

240 μL of a reaction solution containing 250 mM HEPES-KOH (pH 8), 31.3 mM ATP and 31.3 mM $MgCl_2$, or 240 μL of a reaction solution containing 250 mM HEPES-KOH (pH 8), 31.3 mM ATP, 31.3 mM AMP and 313 mM $MgCl_2$ was prepared, and to each solutions, 30 μL of L-tyrosine was added so that its final concentration was 50 μM, and 30 μL of TyrRS (derived from *E. coli*) was added so that its final concentration was 5 μM, and the solution was treated at 50° C. for 30 minutes. After the reaction, 60 μL of trichloroacetic acid was added so that its final concentration was 4%, to terminate the reaction. After the termination of the reaction, the precipitate was removed by centrifugation to prepare Example Products 32 and 33.

(Measurement of Pyrophosphoric Acid in Accordance with Molybdenum Blue Method: Step (II) in the Method of the Present Invention)

Example 19

Figure 5B:
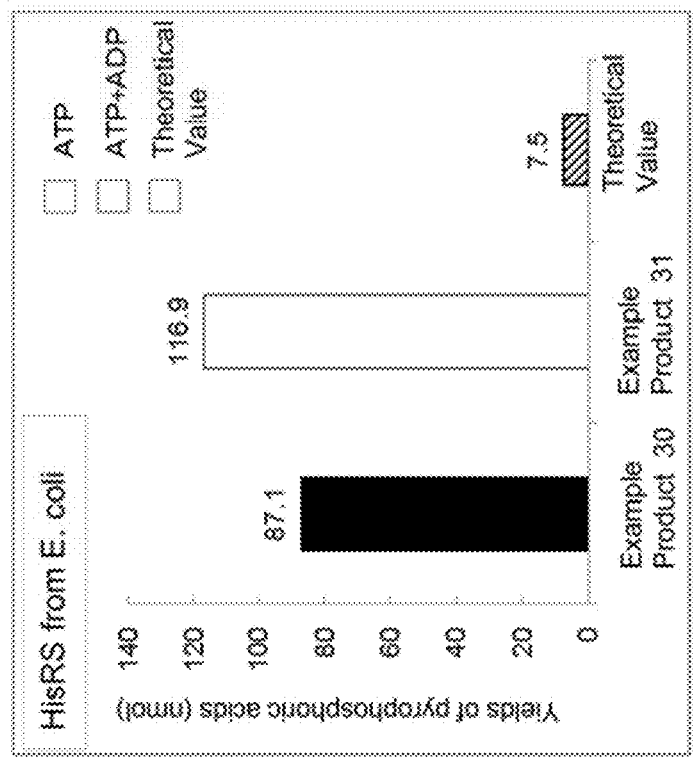
FIGS. 5A-5C illustrate yields of pyrophosphoric acids depending on various nucleotides in various AARSs using L-amino acids.
Figure 5A:
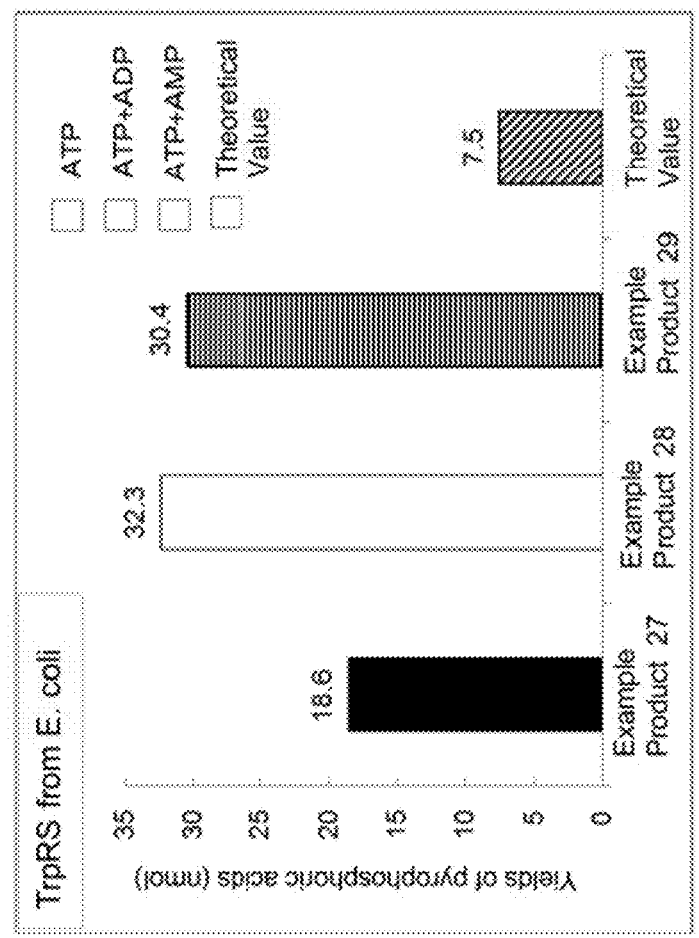
Figure 5C:
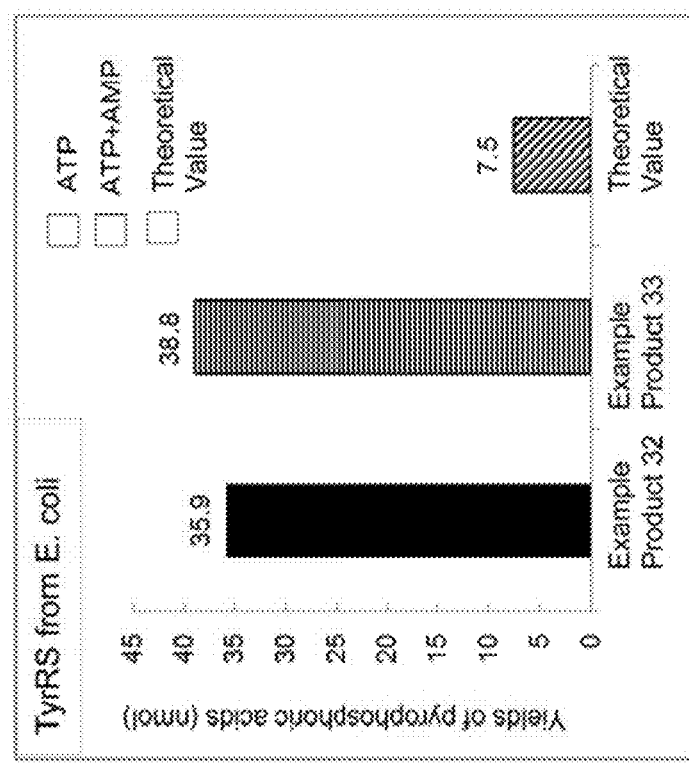

The Example Products 27 to 33 prepared in Examples 16 to 18 were measured in accordance with the molybdenum blue method described in Example 7. As a result, when ATP and ADP, or ATP and AMP were added, the yield of the pyrophosphoric acid increased compared to the case that only ATP was added, as shown in FIGS. 5A-5C. This result indicated that ADP and AMP were effective as nucleotides used for the AARS reaction.

(Comparison Between Yields of Pyrophosphoric Acids in AARS Reactions Described in the Present Invention and a Known Document)

Comparative Example 1

In accordance with the reaction conditions described in Non-Patent Documents 6, 150 µL of a reaction solution containing 4.7 µM HisRS (derived from thermophile), 50 µM L-histidine, 0.2 mM ATP, 5 mM $MgCl_2$, 15 mM HEPES-KOH (pH 8) and 10 mM KCl was prepared, and subjected to enzyme reaction at 80° C. for 30 minutes. After the enzyme reaction, 30 µL of trichloroacetic acid was added so that its final concentration was 4%, to terminate the reaction. After the termination of the reaction, the precipitate was removed by centrifugation to prepare Comparative Product 1.

Comparative Example 2

In accordance with the reaction conditions described in Non-Patent Documents 7, 150 µL of a reaction solution containing 3.1 µM SerRS (derived from thermophile), 50 µM L-serine, 2 mM ATP, 5 mM $MgCl_2$, 100 mM Tris-HCl (pH 8) and 10 mM KCl was prepared, and subjected to enzyme reaction at 80° C. for 30 minutes. After the enzyme reaction, 30 µL of trichloroacetic acid was added so that its final concentration was 4%, to terminate the reaction. After the termination of the reaction, the precipitate was removed by centrifugation to prepare Comparative Product 2.

Comparative Example 3

In accordance with the reaction conditions described in Non-Patent Documents 6, 150 µL of a reaction solution containing 4.5 µM LysRS (derived from thermophile), 50 µM L-lysine, 0.2 mM ATP, 5 mM $MgCl_2$, 15 mM HEPES-KOH (pH 8) and 10 mM KCl was prepared, and subjected to enzyme reaction at 80° C. for 30 minutes. After the enzyme reaction, 30 µL of trichloroacetic acid was added so that its final concentration was 4%, to terminate the reaction. After the termination of the reaction, the precipitate was removed by centrifugation to prepare Comparative Product 3.

Example 20

150 µL of a reaction solution containing 5.2 µM HisRS (derived from thermophile), 50 µM L-histidine, 25.9 mM ATP, 259 mM $MgCl_2$ and 20 mM HEPES-KOH (pH 8) was prepared, and subjected to enzyme reaction at 70° C. for 30 minutes. After the enzyme reaction, 30 µL of trichloroacetic acid was added so that its final concentration was 4%, to terminate the reaction. After the termination of the reaction, the precipitate was removed by centrifugation to prepare Example Product 34.

Example 21

150 µL of a reaction solution containing 5.1 µM SerRS (derived from thermophile), 50 µM L-serine, 25.6 mM ATP, 256 mM $MgCl_2$ and 20 mM HEPES-KOH (pH 8) was prepared, and subjected to enzyme reaction at 70° C. for 30 minutes. After the enzyme reaction, 30 µL of trichloroacetic acid was added so that its final concentration was 4%, to terminate the reaction. After the termination of the reaction, the precipitate was removed by centrifugation to prepare Example Product 35.

Example 22

150 µL of a reaction solution containing 4.4 µM LysRS (derived from thermophile), 50 µM L-lysine, 22 mM ATP, 220 mM $MgCl_2$ and 20 mM HEPES-KOH (pH 8) was prepared, and subjected to enzyme reaction at 70° C. for 30 minutes. After the enzyme reaction, 30 µL of trichloroacetic acid was added so that its final concentration was 4%, to terminate the reaction. After the termination of the reaction, the precipitate was removed by centrifugation to prepare Example Product 36.

Example 23

Figure 6:
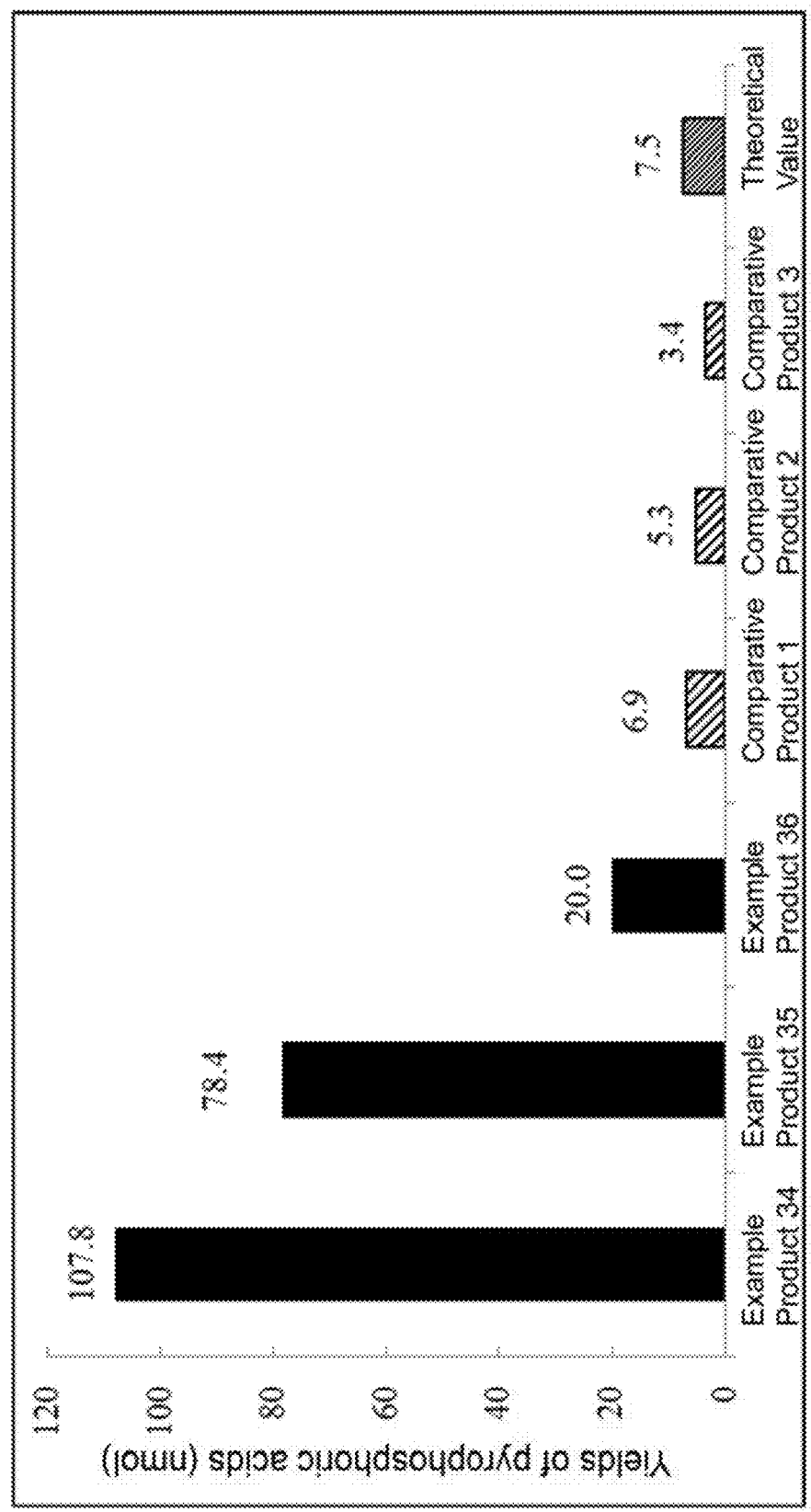
FIG. 6 illustrates yields of pyrophosphoric acids in the AARS reactions according to the present invention and the known documents (Non-Patent Documents 6 and 7).

Pyrophosphoric acids of Comparative Products 1 to 3 and Example Products 34 to 36 obtained in Comparative Examples 1 to 3 and Examples 20 to 22 were measured by the molybdenum blue method described in Example 7. As a result, as shown in FIG. 6, the pyrophosphoric acid was produced in an amount larger than the theoretical value of the pyrophosphoric acid presumably produced when all of the added amino acids were used in the reaction, in the method of the present invention. On the other hand, amounts of the pyrophosphoric acid for Comparative Products were the theoretical value or lower. This result indicated that the molecular number of the pyrophosphoric acid produced in the conventional measurement method using AARS was smaller than the molecular number of the amino acid, but in the method of the present invention, the pyrophosphoric acid was produced in an amount larger than the molecular number of the amino acid.

(Comparison Between Yields of Pyrophosphoric Acids by AARS Reactions with and without Addition of Nucleophilic Agent)

Comparative Example 4

150 µL of a reaction solution containing 1 µM HisRS (derived from thermophile), 30 µM L-histidine, 2 mM ATP, 20 mM $MgCl_2$, 400 mM hydroxylamine (nucleophilic agent) and 200 mM HEPES-KOH (pH 8) was prepared, and subjected to enzyme reaction at 70° C. for 30 minutes. After the enzyme reaction, 30 µL of trichloroacetic acid was added so that its final concentration was 4%, to terminate the reaction. After the termination of the reaction, the precipitate was removed by centrifugation to prepare Comparative Product 4.

Example 24

150 µL of a reaction solution containing 1 µM HisRS (derived from thermophile), 30 µM L-histidine, 2 mM ATP, 20 mM $MgCl_2$ and 200 mM HEPES-KOH (pH 8), and a 150 µL of reaction solution containing 5 µM SerRS (derived from thermophile), 30 µM L-serine, 2 mM ATP, 6 mM $MgCl_2$ and 200 mM HEPES-KOH (pH 8) were prepared, and subjected to enzyme reaction at 70° C. for 30 minutes. After the enzyme reaction, 30 µL of trichloroacetic acid was added so that its final concentration was 4%, to terminate the reaction. After the termination of the reaction, the precipitate was removed by centrifugation to prepare Example Products 37 and 38.

Example 25

Figure 7:
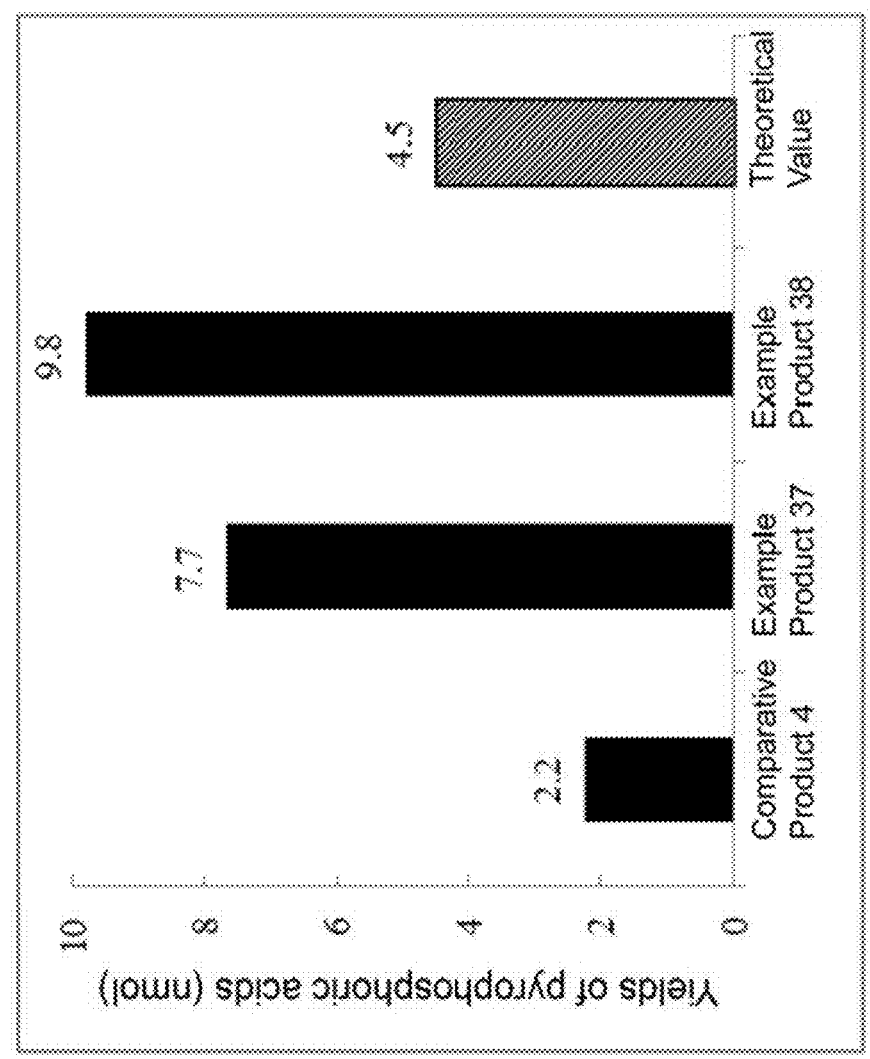
FIG. 7 illustrates comparison of yields of pyrophosphoric acids in the AARS reaction between the presence and the absence of nucleophilic agent.

Pyrophosphoric acids of Comparative Product 4 and Example Products 37 and 38 obtained in Comparative Example 4 and Example 24 were measured by the molybdenum blue method described in Example 7. As a result, as shown in FIG. 7, the pyrophosphoric acid was produced in an amount larger than the theoretical value of the pyrophosphoric acid presumably produced when all of the added amino acids were used in the reaction, in the method of the present invention. On the other hand, amounts of the pyrophosphoric acid for Comparative Products were the theoretical value or lower. This result indicated that the molecular number of the produced pyrophosphoric acid in the conventional measurement method using the AARS with the nucleophilic agent was smaller than the molecular number of the amino acid, but in the method of the present invention, the pyrophosphoric acid was produced in an amount larger than the molecular number of the amino acid.

(Temperature Dependency of AARS)

Example 26

Figure 8B:
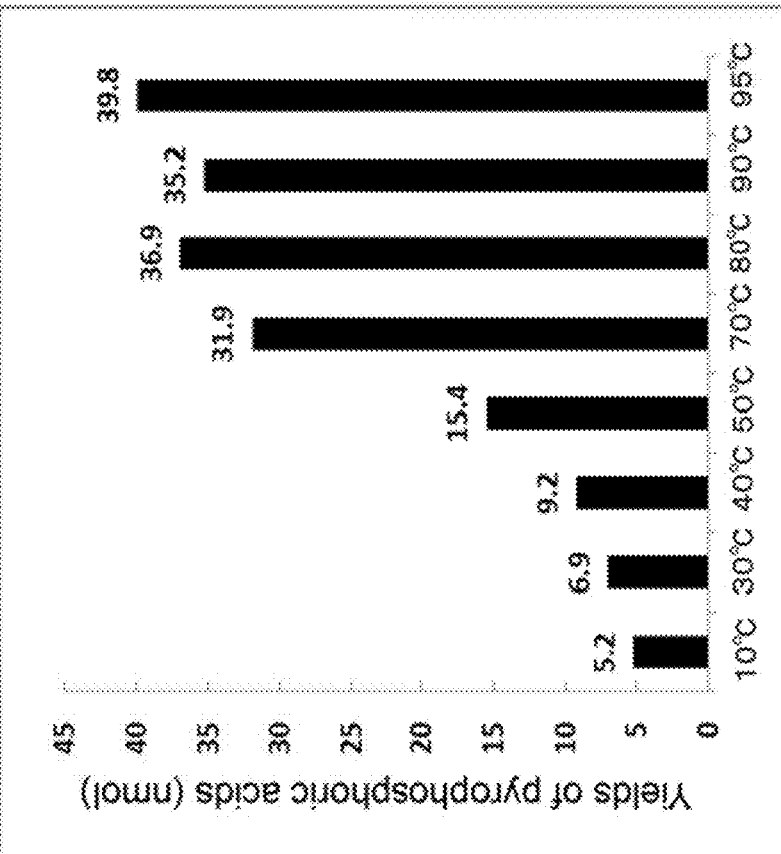
FIGS. 8A-8B illustrate temperature dependency of the AARS.
Figure 8A:
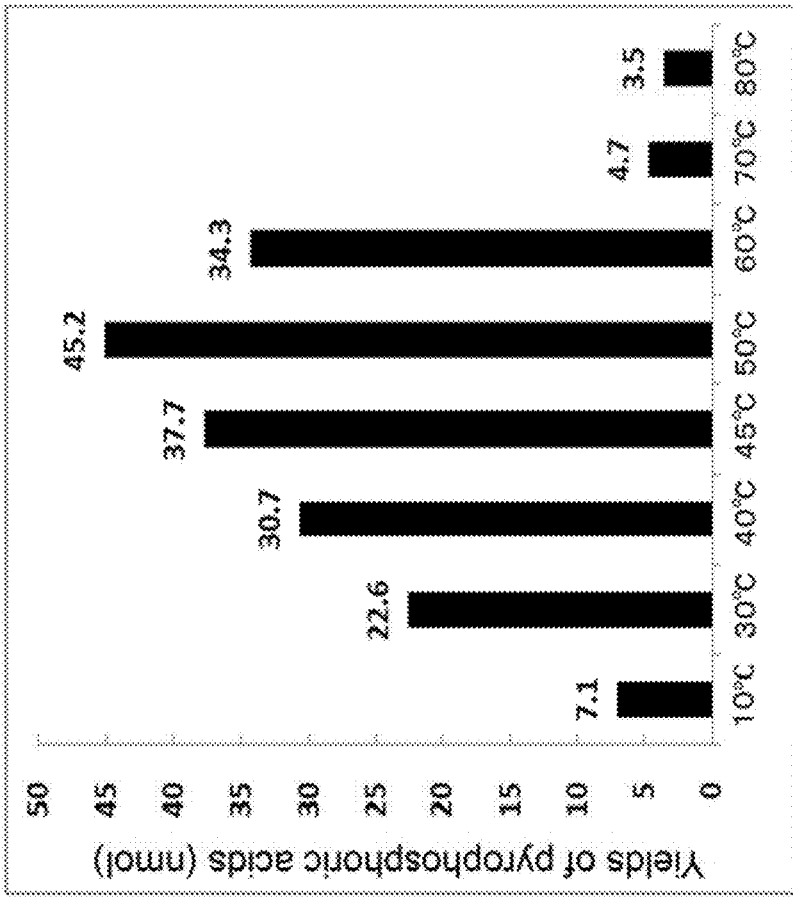
Figure 9A:
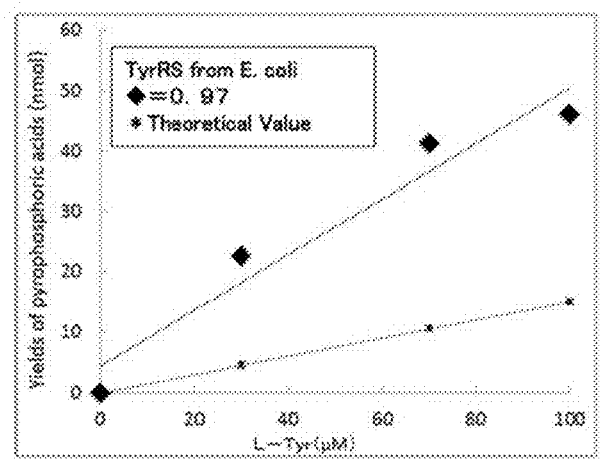
Figure 9B:
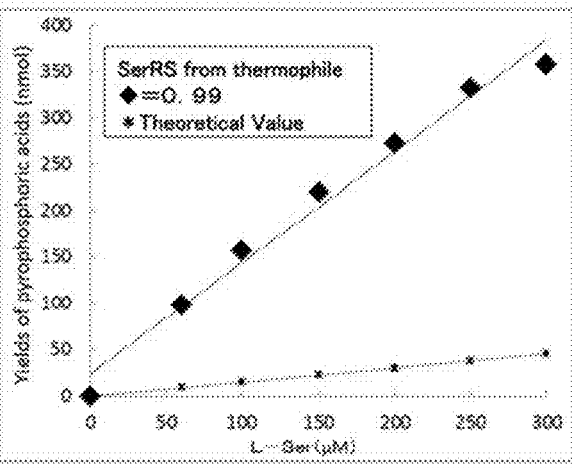

To 120 µL of a reaction solution containing 250 mM HEPES-KOH (pH 8), 31.3 mM ATP and 313 mM MgCl$_2$, 15 µL of L-serine was added so that its final concentration was 50 µM, and 15 µL of SerRS (derived from E. coli) was added so that its final concentration was 5 µM to prepare an enzyme reaction solution, which was reacted at 10° C., 30° C., 40° C., 45° C., 50° C., 60° C., 70° C. and 80° C. respectively for 30 minutes. After the reaction, 30 µL of trichloroacetic acid was added so that its final concentration was 4%, to terminate the reaction. After the termination of the reaction, the precipitate was removed by centrifugation, and the pyrophosphoric acid in the supernatant was measured in accordance with the molybdenum blue method described in Example 7. As a result, as shown in FIGS. 8A-B, it was found that the pyrophosphoric acid was produced within a temperature range of 10 to 80° C., particularly pyrophosphoric acid was well produced within a temperature range of 30 to 60° C.

Example 27

To 120 µL of a reaction solution containing 250 mM HEPES-KOH (pH 8), 12.5 mM ATP and 125 mM MgCl$_2$, 15 µL of L-histidine was added so that its final concentration was 30 µM, and 15 µL of HisRS (derived from thermophile) was added so that its final concentration was 5 µM to prepare an enzyme reaction solution, which was reacted at 10° C., 30° C., 40° C., 50° C., 70° C., 80° C., 90° C. and 95° C. respectively for 15 minutes. After the reaction, 30 µL of trichloroacetic acid was added so that its final concentration was 4%, to terminate the reaction. After the termination of the reaction, the precipitate was removed by centrifugation, and the pyrophosphoric acid in the supernatant was measured in accordance with the molybdenum blue method described in Example 7. As a result, as shown in FIG. 8, it was found that the pyrophosphoric acid was well produced within a temperature range of 10 to 95° C.

(Preparation of Calibration Curve for Amino Acid in Pyrophosphoric Acid Measurement in Accordance with Molybdenum Blue Method)

Example 28

To 120 µL of a reaction solution containing 250 mM HEPES-KOH (pH 8), 31.3 mM ATP and 313 mM MgCl$_2$, 15 µL of L-tyrosine was added so that its final concentration was 0 µM, 30 µM, 70 µM or 100 µM to prepare each sample, then to each sample, 15 µL of TyrRS (derived from E. coli) was further added so that its final concentration was 5 µM, and the sample was reacted at 50° C. for 30 minutes. After the reaction, 30 µL of trichloroacetic acid was added so that its final concentration was 4%, to terminate the reaction. After the termination of the reaction, the precipitate was removed by centrifugation, and the pyrophosphoric acid in the supernatant was measured in accordance with the molybdenum blue method described in Example 7. As a result, as shown in FIGS. 9A-D, the pyrophosphoric acid was produced in an amount larger than the theoretical value of the pyrophosphoric acid presumably produced when all of the added amino acids were used in the reaction. In addition, a correlation between the amino acid concentration and the pyrophosphoric acid amount (R=0.97) was found in a range of the amino acid concentration of 0 to 100 µM, indicating that quantification of L-tyrosine was possible.

Example 29

To 120 µL of a reaction solution containing 250 mM HEPES-KOH (pH 8), 31.3 mM ATP and 313 mM MgCl$_2$, 15 µL of L-serine was added so that its final concentration was 0 µM, 60 µM, 100 µM, 150 µM, 200 µM, 250 µM or 300 µM to prepare each sample, then to each sample, 15 µL of SerRS (derived from thermophile) was further added so that its final concentration was 5 µM, and the sample was reacted at 70° C. for 30 minutes. After the reaction, 30 µL of trichloroacetic acid was added so that its final concentration was 4%, to terminate the reaction. After the termination of the reaction, the precipitate was removed by centrifugation, and the pyrophosphoric acid in the supernatant was measured in accordance with the molybdenum blue method described in Example 7. As a result, as shown in FIGS. 9A-9D, the pyrophosphoric acid was produced in an amount larger than the theoretical value of the pyrophosphoric acid presumably produced when all of the added amino acids were used in the reaction. In addition, a correlation between the amino acid concentration and the pyrophosphoric acid amount (R=0.99) was found in a range of the amino acid concentration of 0 to 300 µM, indicating that quantification of L-serine was possible.

Example 30

To 120 µL of a reaction solution containing 250 mM HEPES-KOH (pH 8), 31.3 mM ATP and 313 mM MgCl$_2$, 15 µL of L-histidine was added so that its final concentration was 0 µM, 1.0 µM, 3.0 µM or 5.0 µM to prepare each sample, then to each sample, 15 µL of HisRS (derived from E. coli) was further added so that its final concentration was 5 µM, and the sample was reacted at 50° C. for 30 minutes. After the reaction, 30 µL of trichloroacetic acid was added so that its final concentration was 4%, to terminate the reaction. After the termination of the reaction, the precipitate was removed by centrifugation, and the pyrophosphoric acid in the supernatant was measured in accordance with the molybdenum blue method described in Example 7. As a result, as shown in FIGS. 9A-9D, the pyrophosphoric acid was produced in an amount larger than the theoretical value of the pyrophosphoric acid presumably produced when all of the added amino acids were used in the reaction. In addition, a correlation between the amino acid concentration and the pyrophosphoric acid amount (R=0.99) was found in a range of the amino acid concentration of 0 to 5 µM, indicating that quantification of L-histidine was possible.

Example 31

To 120 µL of a reaction solution containing 250 mM HEPES-KOH (pH 8), 31.3 mM ATP and 313 mM $MgCl_2$, 15 µL of L-tryptophan was added so that its final concentration was 0 µM, 1.0 µM, 3.0 µM or 5.0 µM to prepare each sample, then to each sample, 15 µL of TrpRS (derived from thermophile) was further added so that its final concentration was 5 µM, and the sample was reacted at 70° C. for 30 minutes. After the reaction, 30 µL of trichloroacetic acid was added so that its final concentration was 4%, to terminate the reaction. After the termination of the reaction, the precipitate was removed by centrifugation, and the pyrophosphoric acid in the supernatant was measured in accordance with the molybdenum blue method described in Example 7. As a result, as shown in FIGS. 9A-9D, the pyrophosphoric acid was produced in an amount larger than the theoretical value of the pyrophosphoric acid presumably produced when all of the added amino acids were used in the reaction. In addition, a correlation between the amino acid concentration and the pyrophosphoric acid amount (R=0.99) was found in a range of the amino acid concentration of 0 to 5 µM, indicating that quantification of L-tryptophan was possible.
(Preparation of Calibration Curve for Amino Acid in Hydrogen Ion Concentration Measurement by Cumulative ISFET Electrode)

Example 32

100 µL of samples respectively containing TrpRS (derived from thermophile) at a final concentration of 5 µM, L-tryptophan at a final concentration of 0 µM, 15 µM, 20 µM, 40 µM or 50 µM, ATP at a final concentration of 10 mM, $MgCl_2$ at a final concentration of 100 mM and HEPES-KOH (pH 8) at a final concentration of 1 mM as reaction compositions were prepared, and reacted at 70° C. for 30 minutes. After the reaction, they were allowed to stand at room temperature for 10 minutes.

Example 33

100 µL of samples respectively containing LysRS (derived from thermophile) at a final concentration of 5 µM, L-lysine at a final concentration of 0 µM, 15 µM, 20 µM, 40 µM or 50 µM, ATP at a final concentration of 10 mM, $MgCl_2$ at a final concentration of 100 mM and HEPES-KOH (pH 8) at a final concentration of 1 mM as reaction compositions were prepared, and treated in the same manner as in Example 32.

Example 34

100 µL of each sample containing SerRS (derived from thermophile) at a final concentration of 5 µM, L-serine at a final concentration of 0 µM, 20 µM, 50 µM or 60 µM, ATP at a final concentration of 10 mM, $MgCl_2$ at a final concentration of 100 mM and HEPES-KOH (pH 8) at a final concentration of 1 mM as reaction compositions was prepared, and treated in the same manner as in Example 32.

Example 35

Figure 10A:
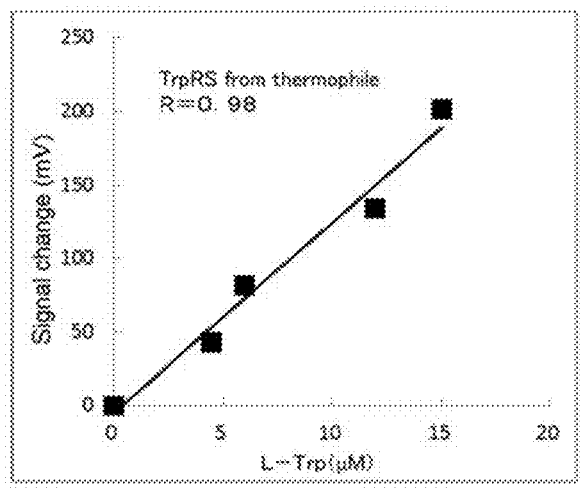
Figure 10B:
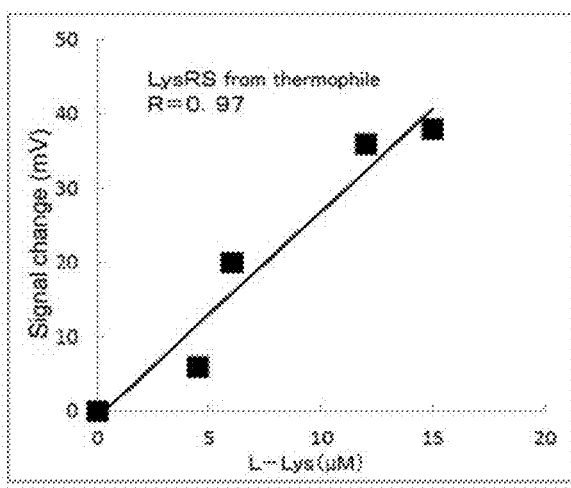

Measurement using a physiological activity reaction measurement apparatus (AMIS-101X, made by Bio-X Inc.) was carried out. As a cumulative ISFET sensor, a reference electrode-housing AMIS sensor (AMIS-051) was used. 70 µL of a solution containing HEPES-KOH (pH 8) at a final concentration of 1 mM, $MgCl_2$ at a final concentration of 200 mM and KCl at a final concentration of 10 mM was added to each of sensing parts A and B in the AMIS-051. Preheating was carried out at 30° C. for 3 minutes, and after the signal was stabilized, 30 µL of the prepared measurement object (each sample in Examples 32 to 34) was added to the sensing part A and 30 µL of a solution which had the same composition as of each sample in Examples 32 to 34 except that water was added instead of the amino acid was added to the sensing part B, and mixed to measure an amount of signal change (signal change at the sensing part A compared to the signal at the sensing part B) every 5 seconds for 250 seconds. The cumulative frequency of the cumulative ISFET sensor was 10 for this measurement. As a result, as shown in FIGS. 10A-10C, a calibration curve can be prepared for each amino acid, indicating that the amino acids could be quantified in the cumulative ISFET sensor.
(Yield of Pyrophosphoric Acid Depending on Various ATP Concentrations and Divalent Ions in Various AARSs Using D-Amino Acids: Step (I) in the Method of the Present Invention)

Example 36

240 µL of a reaction solution containing 250 mM HEPES-KOH (pH 8), 31.3 mM ATP and 31.3 mM $MnCl_2$, or 240 µL of a reaction solution containing 250 mM HEPES-KOH (pH 8), 50 mM ATP and 50 mM $MnCl_2$, or 240 µL of a reaction solution containing 250 mM HEPES-KOH (pH 8), 62.5 mM ATP and 62.5 mM $MnCl_2$ was prepared, and to each solution, 30 µL of D-histidine was added so that its final concentration was 50 µM, and 30 µL of HisRS (derived from *E. coli*) was added so that its final concentration was 5 µM, and the solution was treated at 50° C. for 30 minutes. After the reaction, 60 µL of trichloroacetic acid was added so that its final concentration was 4%, to terminate the reaction. After the termination of the reaction, the precipitate was removed by centrifugation to prepare Example Products 39 to 41.

Example 37

240 µL of a reaction solution containing 250 mM HEPES-KOH (pH 8), 31.3 mM ATP and 31.3 mM $MnCl_2$, or 240 µL of a reaction solution containing 250 mM HEPES-KOH (pH 8), 50 mM ATP and 50 mM $MnCl_2$, or 240 µL of a reaction solution containing 250 mM HEPES-KOH (pH 8), 62.5 mM ATP and 62.5 mM $MnCl_2$ were prepared, and to each solution, 30 µL of D-tryptophan was added so that its final concentration was 50 µM, and 30 µL of TrpRS (derived from thermophile) was added so that its final concentration was 5 µM, and the solution was treated at 70° C. for 30 minutes. After the reaction, 60 µL of trichloroacetic acid was added so that its final concentration was 4%, to terminate the reaction. After the termination of the reaction, the precipitate was removed by centrifugation to prepare Example Products 42 to 44.
(Measurement of Pyrophosphoric Acid in Accordance with Molybdenum Blue Method: Step (II) in the Method of the Present Invention)

Example 38

Figure 11A:
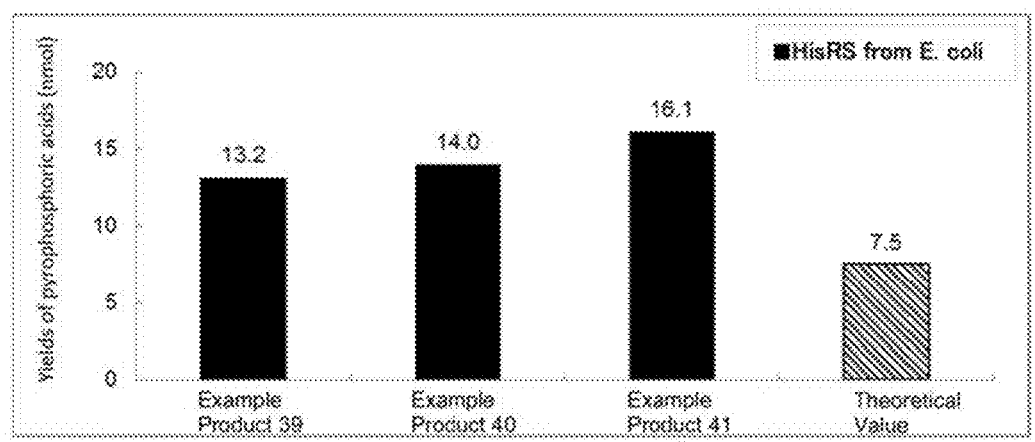
FIGS. 11A-11B yields of pyrophosphoric acids depending on various ATP concentrations and divalent ions in various AARSs using D-amino acids.
Figure 11B:
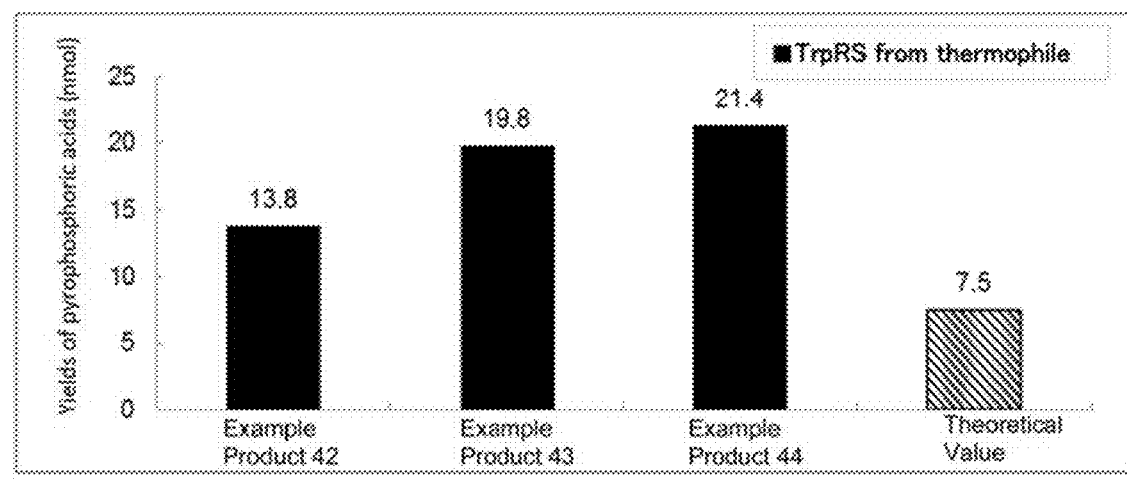

As a result of measuring Example Products 39 to 44 prepared in Examples 36 and 37 in accordance with the molybdenum blue method described in Examples 7, it was found that the pyrophosphoric acid increased as the concentrations of ATP and MnCl$_2$ increased, as shown in FIGS. 11A-11B. In addition, the pyrophosphoric acid was produced in an amount larger than the theoretical value of the pyrophosphoric acid produced when all of the added amino acids were used in the enzyme reaction. Thus, it was shown that the pyrophosphoric acid was produced in a molar number larger than the molecular number of the amino acids contained in the sample in accordance with the method of the present invention.

(Preparation of Calibration Curve for D-Amino Acid in Pyrophosphoric Acid Measurement in Accordance with Molybdenum Blue Method)

Example 39

Figure 12A:
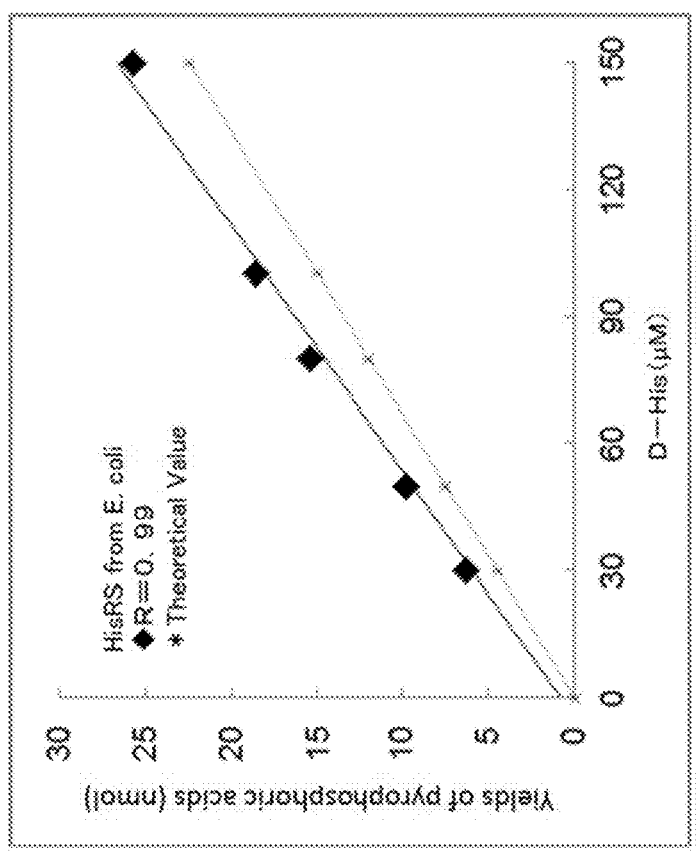
FIGS. 12A-12B illustrate calibration curves for D-amino acids in pyrophosphoric acid measurement in accordance with a molybdenum blue method.
Figure 12B:
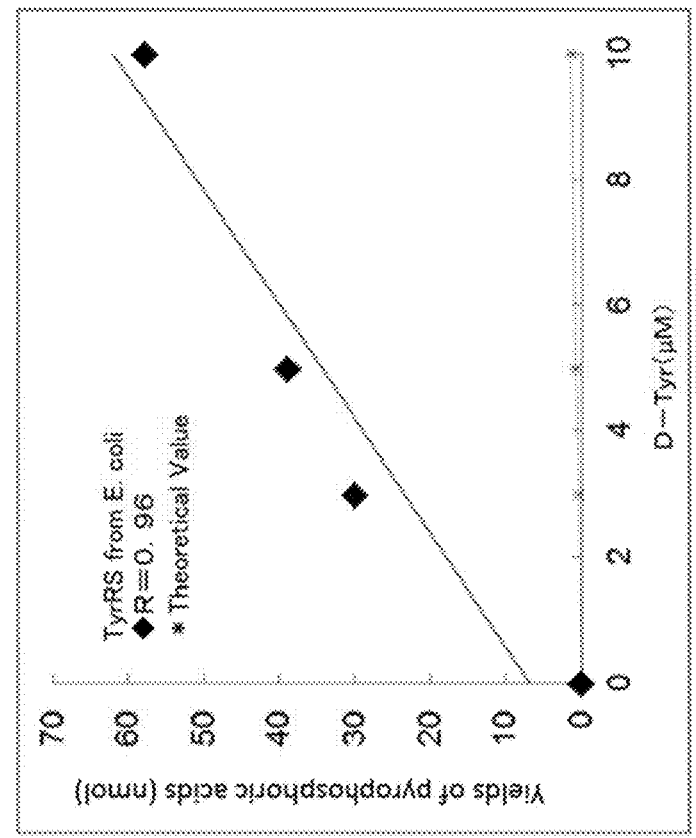

To 120 µL of a reaction solution containing 250 mM HEPES-KOH (pH 8), 50 mM ATP and 50 mM MnCl$_2$, 15 µL of D-tyrosine was added so that its final concentration was 0 µM, 3 µM, 5 µM or 10 µM to prepare each sample, then to each sample, 15 µL of TyrRS (derived from *E. coli*) was further added so that its final concentration was 5 µM, and the sample was reacted at 40° C. for 30 minutes. After the reaction, 30 µL of trichloroacetic acid was added so that its final concentration was 4%, to terminate the reaction. After the termination of the reaction, the precipitate was removed by centrifugation, and the pyrophosphoric acid in the supernatant was measured in accordance with the molybdenum blue method described in Example 7. As a result, as shown in FIGS. 12A-12B, the pyrophosphoric acid was produced in an amount larger than the theoretical value of the pyrophosphoric acid presumably produced when all of the added amino acids were used in the reaction. In addition, a correlation between the amino acid concentration and the pyrophosphoric acid amount (R=0.96) was found in a range of the amino acid concentration of 0 to 10 µM, indicating that quantification of D-tyrosine was possible.

Example 40

To 120 µL of a reaction solution containing 250 mM HEPES-KOH (pH 8), 50 mM ATP and 50 mM MnCl$_2$, 15 µL of D-histidine was added so that its final concentration was 0 µM, 30 µM, 50 µM, 80 µM, 100 µM or 150 µM to prepare each sample, then to each sample, 15 µL of HisRS (derived from *E. coli*) was further added so that its final concentration was 5 µM, and the sample was reacted at 40° C. for 30 minutes. After the reaction, 30 µL of trichloroacetic acid was added so that its final concentration was 4%, to terminate the reaction. After the termination of the reaction, the precipitate was removed by centrifugation, and the pyrophosphoric acid in the supernatant was measured in accordance with the molybdenum blue method described in Example 7. As a result, as shown in FIGS. 12A-12B, the pyrophosphoric acid was produced in an amount larger than the theoretical value of the pyrophosphoric acid presumably produced when all of the added amino acids were used in the reaction. In addition, a correlation between the amino acid concentration and the pyrophosphoric acid amount (R=0.99) was found in a range of the amino acid concentration of 0 to 150 µM, indicating that quantification of D-histidine was possible.

(Measurement of D-Amino Acid after Removal of L-Amino Acid)

Example 41

A solution was prepared so as to contain HEPES-KOH (pH 8) at a final concentration of 200 mM, L-tryptophan at a final concentration of 0.5 mM, D-tryptophan at a final concentration of 0.5 mM, pyridoxal phosphate at a final concentration of 25 µM and tryptophanase at a final concentration of 0.8 U/mL, and reacted at 37° C. for 5 minutes. After the reaction, the solution was subjected to heat treatment at 80° C. for 30 minutes, and the precipitate was removed by centrifugation.

Example 42

30 µL of the amino acid solution prepared in Example 41 was added to 240 µL of a reaction solution containing 250 mM HEPES-KOH (pH 8), 50 mM ATP and 50 mM MnCl$_2$ to prepare each sample, then to each sample, 30 µL of TrpRS (derived from *E. coli*) was further added so that its final concentration was 5 µM, and the sample was reacted at 40° C. for 30 minutes. After the reaction, 60 µL of trichloroacetic acid was added so that its final concentration was 4%, to terminate the reaction. After the termination of the reaction, the precipitate was removed by centrifugation to prepare Example Product 45. In the same manner, Comparative Products 5 and 6 were prepared in order to measure the yield of the pyrophosphoric acid produced by the AARS reaction from an amino acid solution containing only 0.5 mM D-tryptophan or 0.5 mM L-tryptophan as amino acids and not treated with tryptophanase.

Example 43

Figure 13:
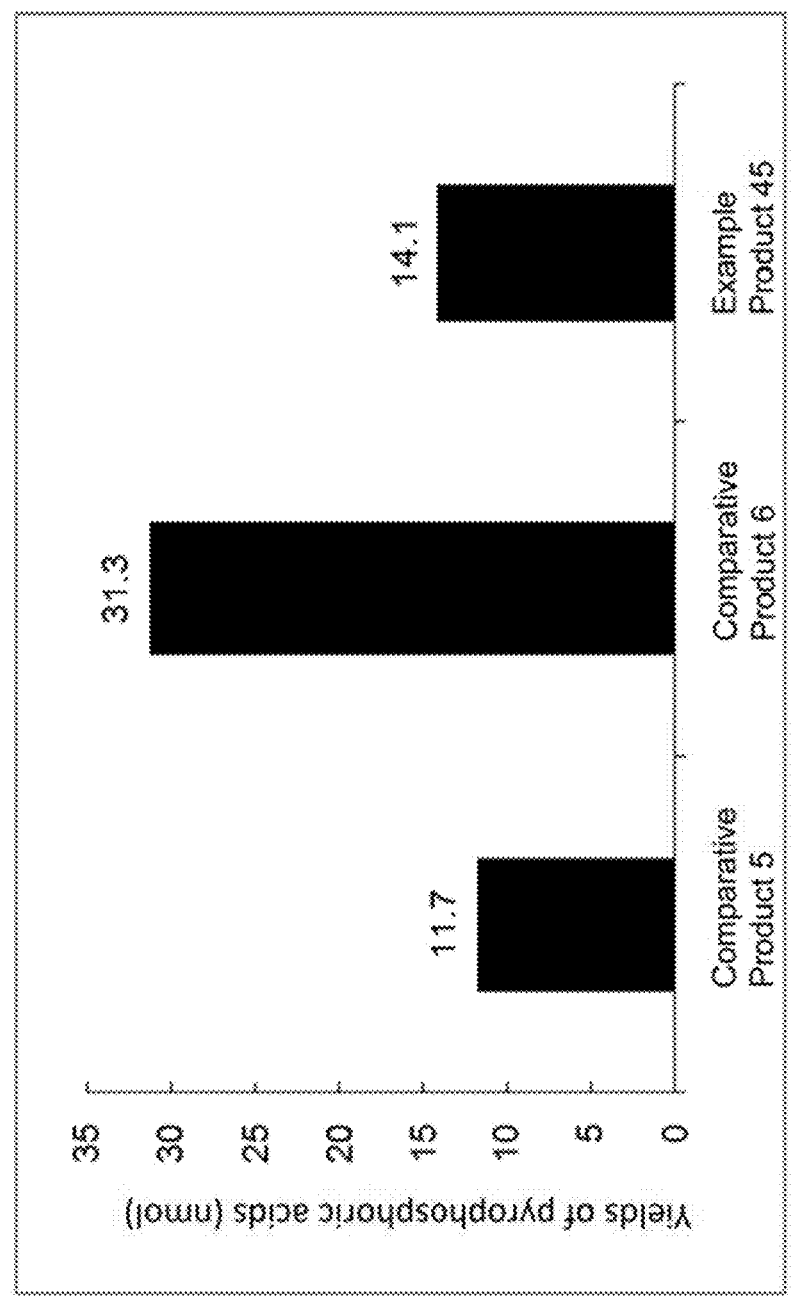
FIG. 13 illustrates measurement of D-amino acids after removal of L-amino acids.
Figure 14B:
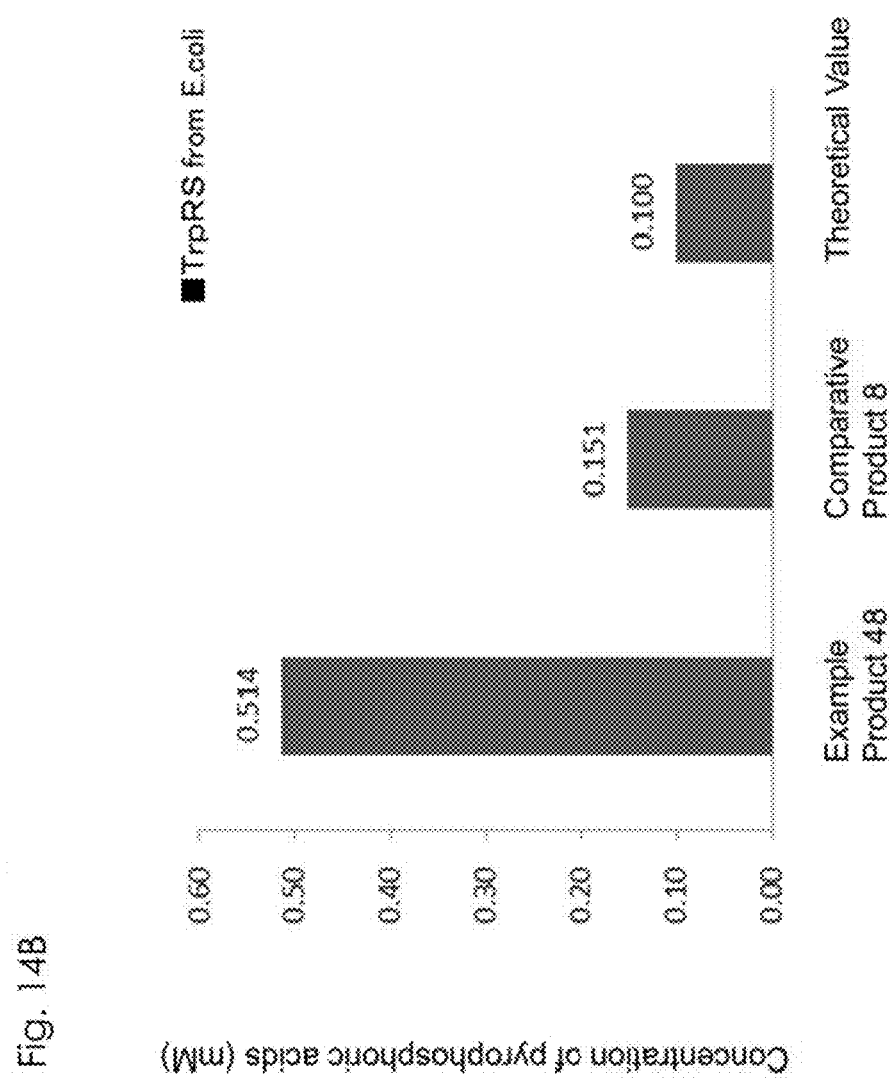
Figure 14C:
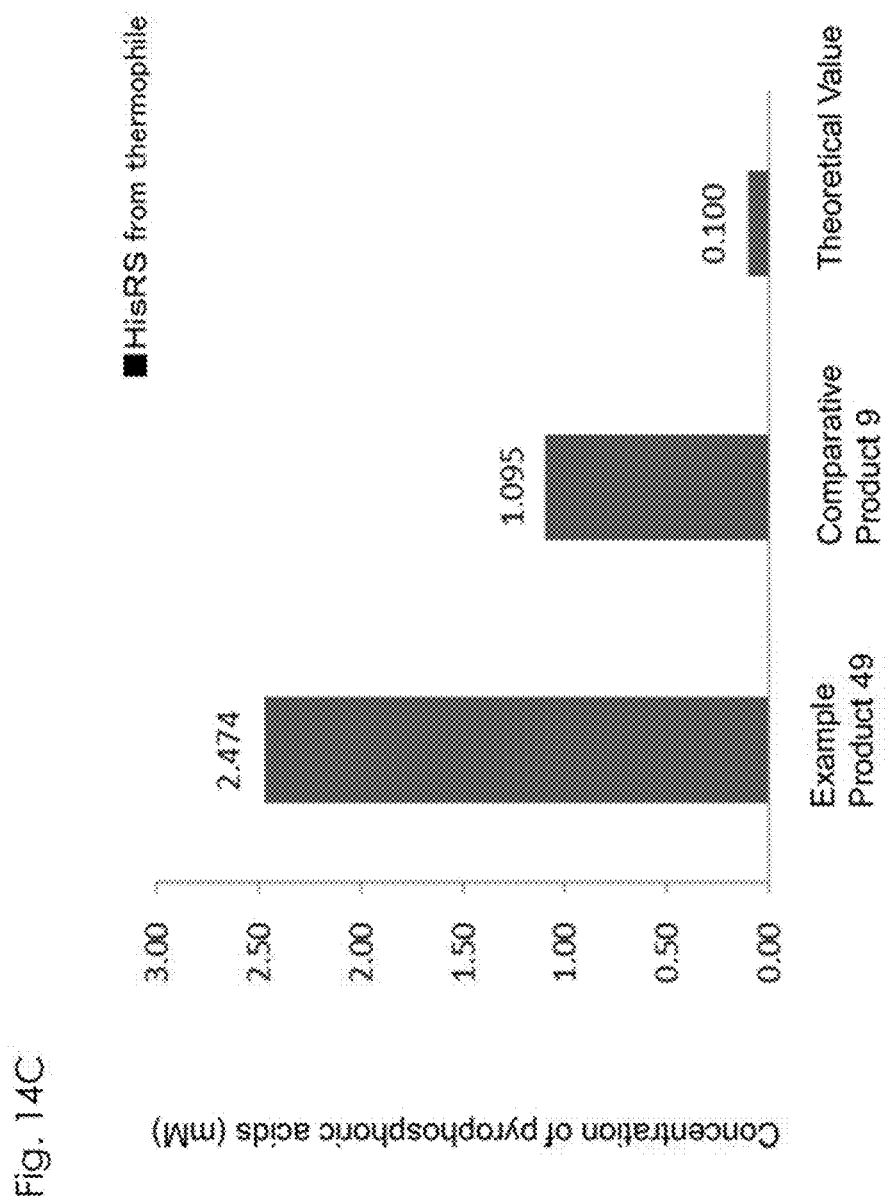
Figure 14D:
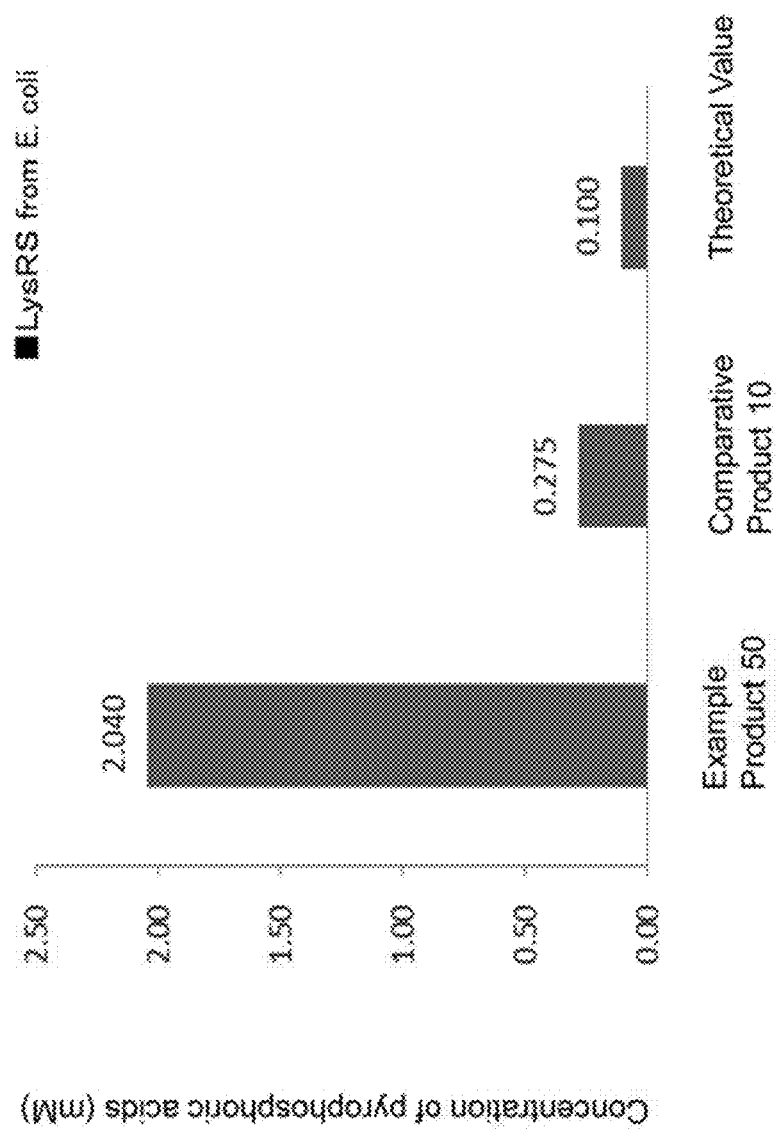
Figure 15A:
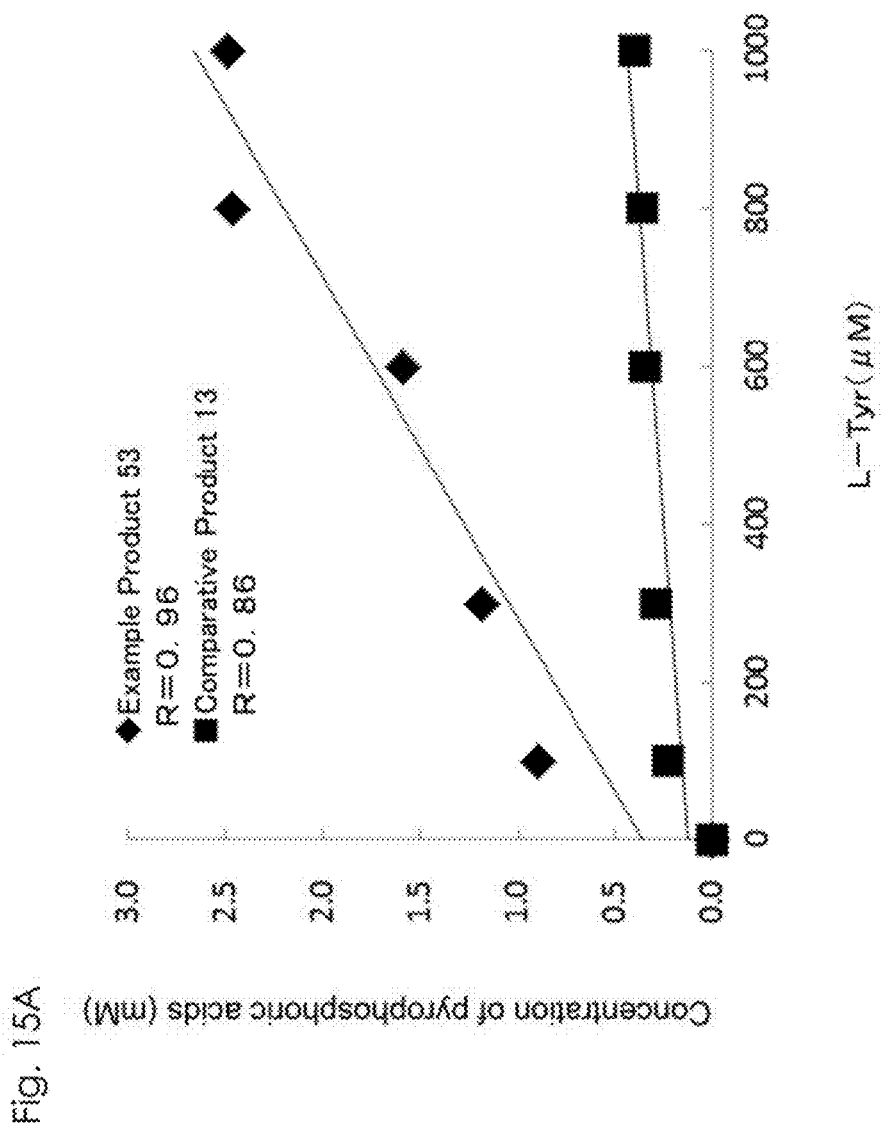
FIGS. 15A-15D illustrate calibration curves for L-amino acids in pyrophosphoric acid measurement in accordance with a molybdenum blue method.
Figure 15B:
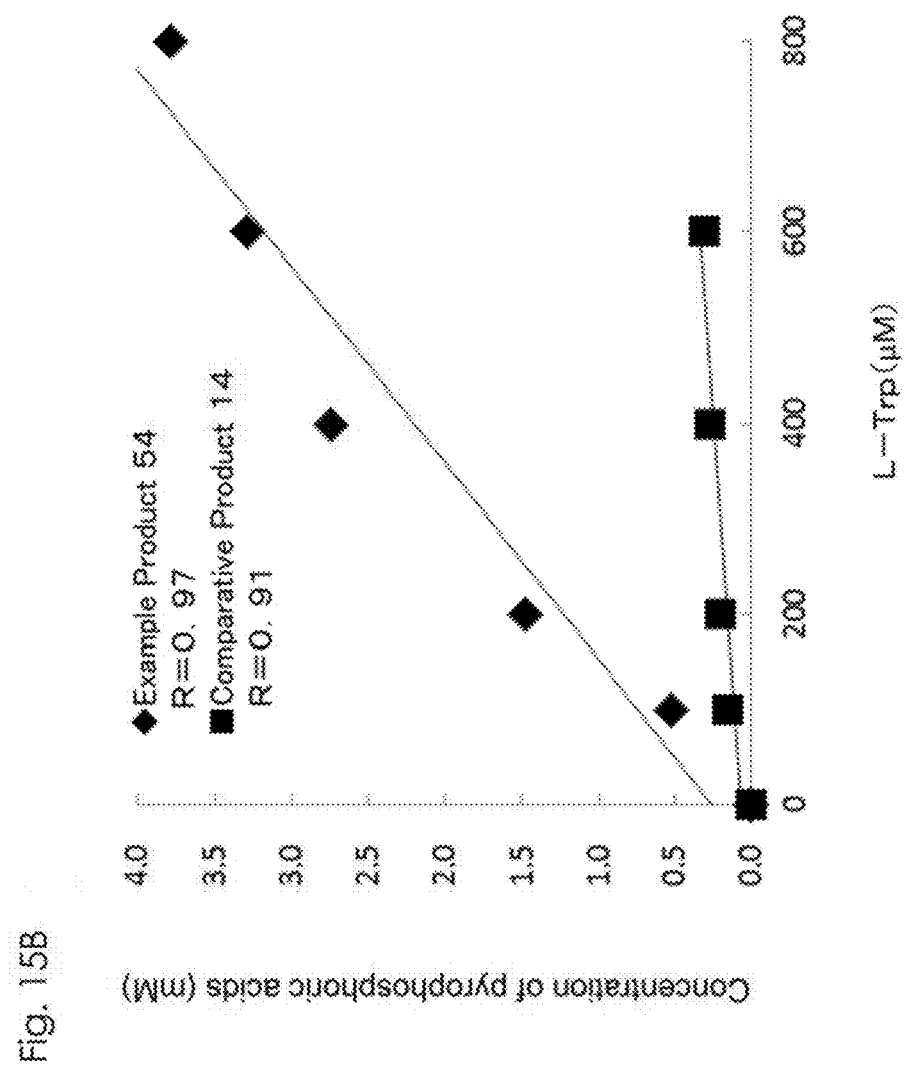
Figure 15C:
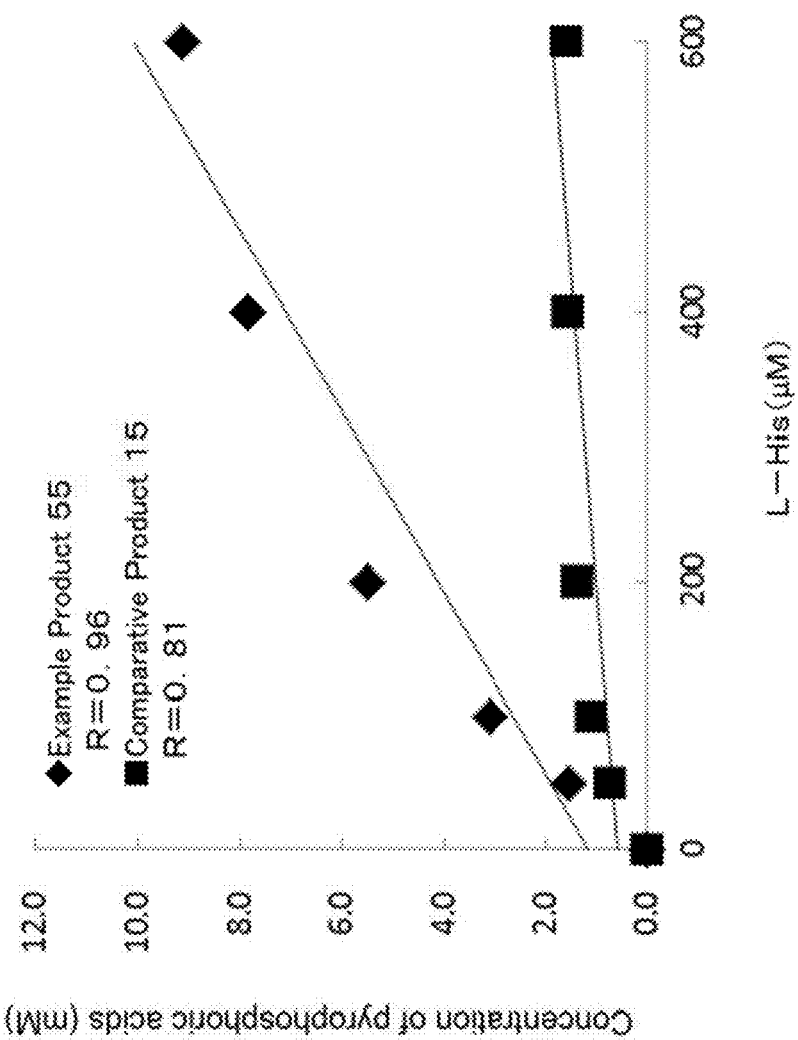
Figure 15D:
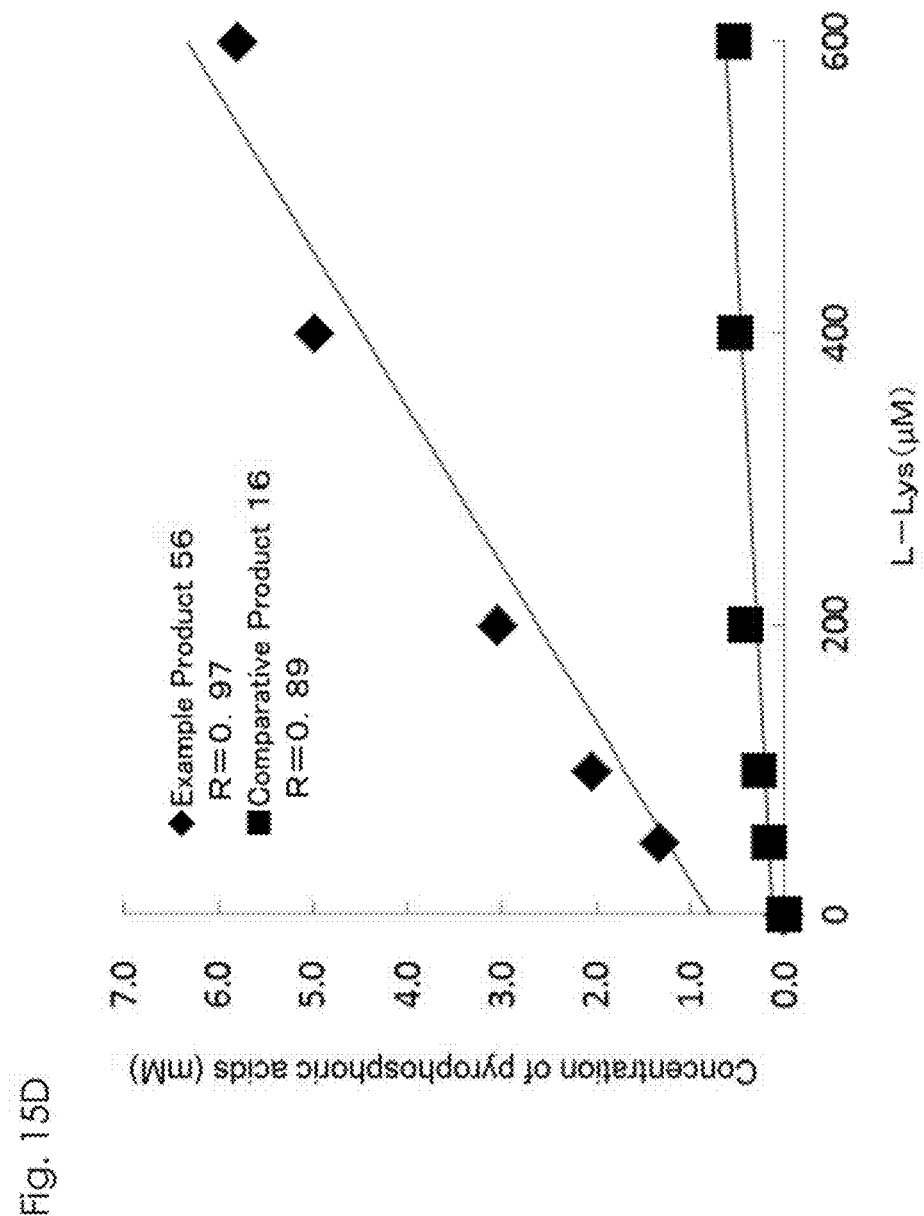

Pyrophosphoric acids in supernatants of Example Product 45 and Comparative Products 5 and 6 obtained in Example 42 were measured in accordance with the molybdenum blue method described in Example 7. As a result, as shown in FIG. 13, Example Product 45 and Comparative Product 5 showed substantially equivalent yields of pyrophosphoric acid. From this result, it was considered that the L-tryptophan in the mixture solution of D-form and L-form tryptophans could been removed by enzyme treatment. Thus, it was indicated that the D-amino acid in the mixture solution of D-form and L-form amino acids could be measured by removing the L-amino acid.

The above results indicated that it was difficult to produce pyrophosphoric acid produced by the AARS reaction in an amount larger than the molar number of the amino acids contained in the sample in the conventional method described in the known documents as shown in Comparative Examples 1 to 4, but in the method of the present invention, reaction products could be amplified by repeatedly using the AARS and the amino acids for reactions. From this fact, in the AARS reaction in the method of the present invention, the pyrophosphoric acid could be produced in the reaction in an amount larger than the molar numbers of amino acids in both cases of the L-form and D-form, as shown in Examples 3 to 19 and Examples 36 to 38. In addition, it was found that the yield of the pyrophosphoric acid varied depending on the enzyme reaction temperature, and the AARS reaction preferably occurred at 10 to 95° C. for the AARSs derived from *E. coli* and thermophile, as shown in Examples 26 and 27. Furthermore, as shown in Examples 28 to 31 and Examples 39 and 40, it was found that the pyrophosphoric acid linearly increased depending on the amino acid concentration for each AARS in both cases of L-form and D-form amino acids, i.e. there was a correlation between the amino acid concentration and the pyrophosphoric acid amount, and it was confirmed that calibration curves of various amino acids in accordance with the molybdenum blue method that is a simple method could be prepared for the pyrophosphoric acid produced by the AARS reaction of the present invention. In addition, from Examples 41 to 43, it was confirmed that, in the case of the mixture solution of the L-form and D-form amino acids, after removing one amino acid, the remaining amino acid could be measured by AARS.

As apparent from the above description, even when using a simple method such as the molybdenum blue method, the method of the present invention allows quantification of the amino acids in a concentration range of 1 to 300 µM, and this range was comparable to the amino acid quantification range of 1 to 250 µM in the amino acid-quantifying method of high sensitivity analysis in the prior art. In addition, as shown in Example 35, calibration curves for various amino acids could be prepared by the cumulative ISFET electrode. The amino acid quantification range was 0 to 20 µM, and thus it was found that the amino acids could be quantified in a concentration range significantly lower than the amino acid quantification range of 300 to 900 µM for the ISFET electrode of the prior art (90 to 270 µM when converted to the range for the cumulative ISFET electrode used in the above Examples).

Second Aspect of the Present Invention

Embodiments relating to quantification of the amino acid in a high concentration range up to 1,000 µM will be shown in the following Examples 44-63
(Comparison of Yield of Pyrophosphoric Acid Using L-Amino Acids)

Example 44

200 µL of a reaction solution containing 50 mM CHES-KOH (pH 9.5), 530 mM ATP, 1,060 mM $MgCl_2$, 100 µM of L-tyrosine disodium salt dihydrate and 5.3 µM of TyrRS (derived from *E. coli*), or containing 50 mM CHES-KOH (pH 9.5), 424 mM ATP, 590 mM $MgCl_2$, 100 µM of L-tyrosine disodium salt dihydrate and 5.3 µM of TyrRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation to prepare Example Products 46 and 47.

Comparative Example 5

As the reaction conditions of such a low AARS concentration as 5 µM, 200 µL of a reaction solution containing 200 mM HEPES-KOH (pH 8), 25 mM ATP, 250 mM $MgCl_2$, 100 µM of L-tyrosine disodium salt dihydrate and 5 µM of TyrRS (derived from *E. coli*) was prepared and treated at 50° C. for 30 minutes. After the reaction, 40 µL of trichloroacetic acid was added so that its final concentration was 4%, to terminate the reaction. After the termination of the reaction, the precipitate was removed by centrifugation to prepare Comparative Product 7.

Example 45

200 µL of a reaction solution containing 200 mM HEPES-KOH (pH 8.5), 25 mM ATP, 50 mM $CoCl_2$, 100 µM of L-tryptophan and 70 µM of TrpRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation to prepare Example Product 48.

Comparative Example 6

As the reaction conditions of such a low AARS concentration as 5 µM, 200 µL of a reaction solution containing 200 mM HEPES-KOH (pH 8), 25 mM ATP, 250 mM $MgCl_2$, 100 µM of L-tryptophan and 5 µM of TrpRS (derived from *E. coli*) was prepared and treated at 50° C. for 30 minutes. After the reaction, 40 µL of trichloroacetic acid was added so that its final concentration was 4%, to terminate the reaction. After the termination of the reaction, the precipitate was removed by centrifugation to prepare Comparative Product 8.

Example 46

200 µL of a reaction solution containing 200 mM HEPES-KOH (pH 8.5), 75 mM ATP, 375 mM $MgCl_2$, 100 µM of L-histidine and 5.3 µM of HisRS (derived from the thermophile) was prepared and treated at 70° C. for 30 minutes. After the reaction, 40 µL of trichloroacetic acid was added so that its final concentration was 4%, to terminate the reaction. After the termination of the reaction, the precipitate was removed by centrifugation to prepare Example Product 49.

Comparative Example 7

As the reaction conditions of such a low AARS concentration as 5 µM, 200 µL of a reaction solution containing 200 mM HEPES-KOH (pH 8), 25 mM ATP, 250 mM $MgCl_2$, 100 µM of L-histidine and 5 µM of HisRS (derived from the thermophile) was prepared and treated at 70° C. for 30 minutes. After the reaction, 40 µL of trichloroacetic acid was added so that its final concentration was 4%, to terminate the reaction. After the termination of the reaction, the precipitate was removed by centrifugation to prepare Comparative Product 9.

Example 47

200 µL of a reaction solution containing 200 mM HEPES-KOH (pH 8), 100 mM ATP, 100 mM $CoCl_2$, 100 µM of L-lysine and 10 µM of LysRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation to prepare Example Product 50.

Comparative Example 8

As the reaction conditions of such a low AARS concentration as 5 µM, 200 µL of a reaction solution containing 200 mM HEPES-KOH (pH 8), 20 mM ATP, 200 mM $MgCl_2$, 100 µM of L-lysine and 5 µM of LysRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation to prepare Comparative Product 10.

(Measurement of Pyrophosphoric Acid in Accordance with Molybdenum Blue Method: Comparison of Yield of Pyrophosphoric Acid)

Example 48

15 µL of 1 M mercaptoethanol and 60 µL of color developing liquid (2.5% ammonium molybdate/5 N sulfuric acid) were mixed in 150 μL of a reaction solution of each of Example Products 46-50 prepared in Examples 44, 45, 46 and 47, and Comparative Products 7-10 prepared in Comparative Examples 5, 6, 7 and 8, the solution was allowed to stand at room temperature for 20 minutes, and then an absorbance at 580 nm was measured. The pyrophosphoric acid concentration in the reaction solution was determined from a value obtained by subtracting the absorbance value of each sample to which water was added instead of the L-amino acid as a blank from the absorbance value of the respective sample. As a result, as shown in FIGS. 14A-14D, pyrophosphoric acid was produced in Example Products 46-50 in an amount twice or more than that in Comparative Products 7-10 (5 μM of AARS was used), and in an amount five times or more than the theoretical value of the pyrophosphoric acid amount produced when all of the added amino acids were used in the enzyme reaction. Thus, it was revealed that the yields of the pyrophosphoric acid could be significantly increased when compared with the comparative examples, by using the high AARS concentration, and accordingly the high ATP and/or divalent ion concentration as well in the present method.

(Comparison of a Reaction Time)

Example 49

200 μL of a reaction solution containing 200 mM CHES-KOH (pH 9.5), 82.5 mM ATP, 385 mM $MgCl_2$, 20 μM of L-tyrosine disodium salt dihydrate and 5.5 μM of TyrRS (derived from *E. coli*) was prepared and treated at 40° C. for 3 minutes. After the reaction, 40 μL of trichloroacetic acid was added so that its final concentration was 4%, to terminate the reaction. After the termination of the reaction, the precipitate was removed by centrifugation to prepare Example Product 51.

Comparative Example 9

As the reaction conditions of such a low AARS concentration as 5 μM, 200 μL of a reaction solution containing 200 mM HEPES-KOH (pH 8), 25 mM ATP, 250 mM $MgCl_2$, 20 μM of L-tyrosine disodium salt dihydrate and 5 μM of TyrRS (derived from *E. coli*) was prepared and treated at 50° C. for 10 minutes. After the reaction, 40 μL of trichloroacetic acid was added so that its final concentration was 4%, to terminate the reaction. After the termination of the reaction, the precipitate was removed by centrifugation to prepare Comparative Product 11.

Example 50

200 μL of a reaction solution containing 200 mM HEPES-KOH (pH 8.5), 100 mM ATP, 100 mM $CoCl_2$, 50 μM of L-tryptophan and 5.5 μM of TrpRS (derived from *E. coli*) was prepared and treated at 40° C. for 2.5 minutes. After the reaction, 40 μL of trichloroacetic acid was added so that its final concentration was 4%, to terminate the reaction. After the termination of the reaction, the precipitate was removed by centrifugation to prepare Example Product 52.

Comparative Example 10

As the reaction conditions of such a low AARS concentration as 5 μM, 200 μL of a reaction solution containing 200 mM HEPES-KOH (pH 8), 25 mM ATP, 250 mM $MgCl_2$, 50 μM of L-tryptophan and 5 μM of TrpRS (derived from *E. coli*) was prepared and treated at 50° C. for 12 minutes. After the reaction, 40 μL of trichloroacetic acid was added so that its final concentration was 4%, to terminate the reaction. After the termination of the reaction, the precipitate was removed by centrifugation to prepare Comparative Product 12.

(Measurement of Pyrophosphoric Acid in Accordance with Molybdenum Blue Method: Comparison of Reaction Time)

Example 51

Pyrophosphoric acid of each of Example Products 51 and 52 prepared in Examples 49 and 50, and Comparative Products 11 and 12 prepared in Comparative Examples 9 and 10 was measured by the molybdenum blue method as described in Example 48. As a result, as shown in Tables 1 and 2, the same amount of pyrophosphoric acid was produced in Example Products 51 and 52 in such a short time as one thirds or less than in Comparative Products 11 and 12 (5 μM of AARS was used). Thus, it was revealed that the quantification of the pyrophosphoric acid could be done in a shorter time than in Comparative Examples, by using the high AARS concentration, and accordingly the high ATP and/or divalent ion concentration as well in the present method.

TABLE 1

Reaction time for producing a certain amount of pyrophosphoric acid (TyrRS derived from *E. coli*)

| | Reaction time for producing a certain amount of pyrophosphoric acid | Yield of pyrophosphoric acid |
|---|---|---|
| Example Product 51 | 3 minutes | 49.6 μM |
| Comparative Product 11 | 10 minutes | 48.7 μM |

TABLE 2

Reaction time for producing a certain amount of pyrophosphoric acid (TrpRS derived from *E. coli*)

| | Reaction time for producing a certain amount of pyrophosphoric acid | Yield of pyrophosphoric acid |
|---|---|---|
| Example Product 52 | 2.5 minutes | 84.9 μM |
| Comparative Product 12 | 12 minutes | 65.6 μM |

(Comparison of a Measuring Range Using L-Amino Acids)

Example 52

200 μL of a reaction solution containing 150 mM CHES-KOH (pH 9.5), 318 mM ATP, 1,060 mM $MgCl_2$, 0 μM, 100 μM, 300 μM, 600 μM, 800 μM or 1,000 μM of L-tyrosine disodium salt dihydrate, and 5.3 μM of TyrRS (derived from *E. coli*) was prepared and treated at 40° C. for 30 minutes. After the reaction, 40 μL of trichloroacetic acid was added so that its final concentration was 4%, to terminate the reaction. After the termination of the reaction, the precipitate was removed by centrifugation and the pyrophosphoric acid in the supernatant (Example Product 53) was measured by the molybdenum blue method as described in Example 48. On the other hand, as the reaction conditions of such a low AARS concentration as 5 μM, 200 μL a reaction solution containing 200 mM HEPES-KOH (pH 8), 25 mM ATP, 250 mM MgCl$_2$, 0 µM, 100 µM, 300 µM, 600 µM, 800 µM or 1,000 µM of of L-tyrosine disodium salt dihydrate, and 5 µM of TyrRS (derived from *E. coli*) was prepared and treated at 50° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Comparative Product 13) was measured by the molybdenum blue method as described in Example 48. As a result, as shown in FIGS. 15A-15D, while a correlation "R" between the amino acid concentration and the pyrophosphoric acid amount was decreased to 0.86 when measured to a higher amino acid concentration in Comparative Product 13 wherein only 5 µM of TyrRS was used, the correlation (R=0.96) was recognized over a wide range of the amino acid concentration in the present method that used 5.3 µM of TyrRS and accordingly the high ATP and/or divalent ion concentration as well.

Example 53

200 µL of a reaction solution containing 200 mM HEPES-KOH (pH 8.5), 25 mM ATP, 50 mM CoCl$_2$, 0 µM, 100 µM, 200 µM, 400 µM, 600 µM or 800 µM of L-tryptophan, and 70 µM of TrpRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Example Product 54) was measured by the molybdenum blue method as described in Example 48. On the other hand, as the reaction conditions of such a low AARS concentration as 5 µM, 200 µL a reaction solution containing 200 mM HEPES-KOH (pH 8), 25 mM ATP, 250 mM MgCl$_2$, 0 µM, 100 µM, 200 µM, 400 µM or 600 µM of L-tryptophan, and 5 µM of TrpRS (derived from *E. coli*) was prepared and treated at 50° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Comparative Product 14) was measured by the molybdenum blue method as described in Example 48. As a result, as shown in FIGS. 15A-15D, while a correlation "R" between the amino acid concentration and the pyrophosphoric acid amount was decreased to 0.91 when measured to a higher amino acid concentration in Comparative Product 14 wherein only 5 µM of TrpRS was used, the correlation (R=0.97) was recognized over a wide range of the amino acid concentration in the present method that used 70 µM of TrpRS.

Example 54

200 µL of a reaction solution containing 200 mM HEPES-KOH (pH 8.5), 75 mM ATP, 375 mM MgCl$_2$, 0 µM, 50 µM, 100 µM, 200 µM, 400 µM or 600 µM of L-histidine, and 15 µM of HisRS (derived from the thermophile) was prepared and treated at 70° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Example Product 55) was measured by the molybdenum blue method as described in Example 48. On the other hand, as the reaction conditions of such a low AARS concentration as 5 µM, 200 µL a reaction solution containing 200 mM HEPES-KOH (pH 8), 25 mM ATP, 250 mM MgCl$_2$, 0 µM, 50 µM, 100 µM, 200 µM, 400 µM or 600 µM of of L-histidine, and 5 µM of HisRS (derived from the thermophile) was prepared and treated at 70° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Comparative Product 15) was measured by the molybdenum blue method as described in Example 48. As a result, as shown in FIGS. 15A-15D, while a correlation "R" between the amino acid concentration and the pyrophosphoric acid amount was decreased to 0.81 when measured to a higher amino acid concentration in Comparative Product 15 wherein only 5 µM of HisRS was used, the correlation (R=0.96) was recognized over a wide range of the amino acid concentration in the present method that used 15 µM of HisRS.

Example 55

200 µL of a reaction solution containing 200 mM HEPES-KOH (pH 8), 100 mM ATP, 100 mM CoCl$_2$, 0 µM, 50 µM, 100 µM, 200 µM, 400 µM or 600 µM of L-lysine, and 10 µM of LysRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Example Product 56) was measured by the molybdenum blue method as described in Example 48. On the other hand, as the reaction conditions of such a low AARS concentration as 5 µM, 200 µL a reaction solution containing 200 mM HEPES-KOH (pH 8), 20 mM ATP, 200 mM MgCl$_2$, 0 µM, 50 µM, 100 µM, 200 µM, 400 µM or 600 µM of L-lysine, and 5 µM of LysRS (derived from *E. coli*.) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Comparative Product 16) was measured by the molybdenum blue method as described in Example 48. As a result, as shown in FIGS. 15A-15D, while a correlation "R" between the amino acid concentration and the pyrophosphoric acid amount was decreased to 0.89 when measured to a higher amino acid concentration in Comparative Product 16 wherein only 5 µM of LysRS was used, the correlation (R=0.97) was recognized over a wide range of the amino acid concentration in the present method that used 10 µM of LysRS.

(Effects of the Addition of Polar Solvent)

Example 56

200 µL of a reaction solution containing 100 mM HEPES-KOH (pH 7), 150 mM ATP, 150 mM MgCl$_2$, 10 mM ZnSO$_4$, 100 µM of L-valine and 10 µM of ValRS (derived from *E. coli*) (Comparative Product 17) was prepared. And, 200 µL of a reaction solution containing 100 mM HEPES-KOH (pH 7), 150 mM ATP, 150 mM MgCl$_2$, 10 mM ZnSO$_4$, 100 µM of L-valine, and 10 µM of ValRS (derived from *E. coli*) plus 50% glycerol, 10% ethyleneglycol or 10% dimethyl sulfoxide was prepared (Example Products 57-59). These solutions were treated at 50° C. for 30 minutes. After the reaction, 40 µL of trichloroacetic acid was added so that its final concentration was 4%, to terminate the reaction. After the termination of the reaction, the precipitate was removed by centrifugation.

Example 57

200 µL of a reaction solution containing 100 mM MOPS-KOH (pH 6.5), 40 mM ATP, 40 mM MnCl$_2$, 30 µM of L-isoleucine and 10 µM of IleRS (derived from *E. coli*) (Comparative Product 18) was prepared. And, 200 µL of a reaction solution containing 100 mM MOPS-KOH (pH 6.5), 40 mM ATP, 40 mM MnCl$_2$, 30 µM of L-isoleucine, and 10 µM of IleRS (derived from *E. coli*) plus 60% glycerol, 30% ethyleneglycol or 30% dimethyl sulfoxide was prepared (Example Products 60-62). These solutions were treated at 60° C. for 30 minutes. After the reaction, 40 µL of trichloroacetic acid was added so that its final concentration was 4%, to terminate the reaction. After the termination of the reaction, the precipitate was removed by centrifugation.
(Measurement of Pyrophosphoric Acid in Accordance with Molybdenum Blue Method: Effects of the Addition of the Polar Solvent)

Example 58

Figure 16A:
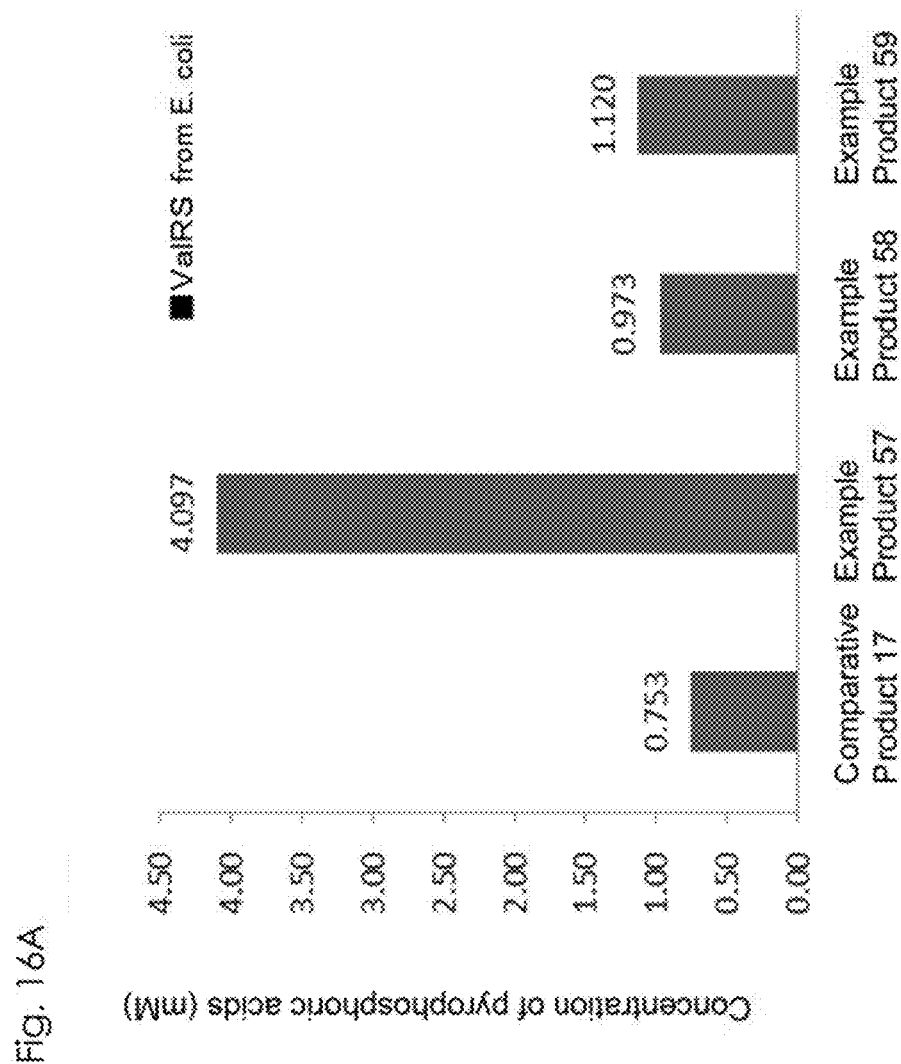
FIGS. 16A-16B illustrate comparison of yields of pyrophosphoric acids in the AARS reaction between the addition and non-addition of the polar solvent.
Figure 16B:
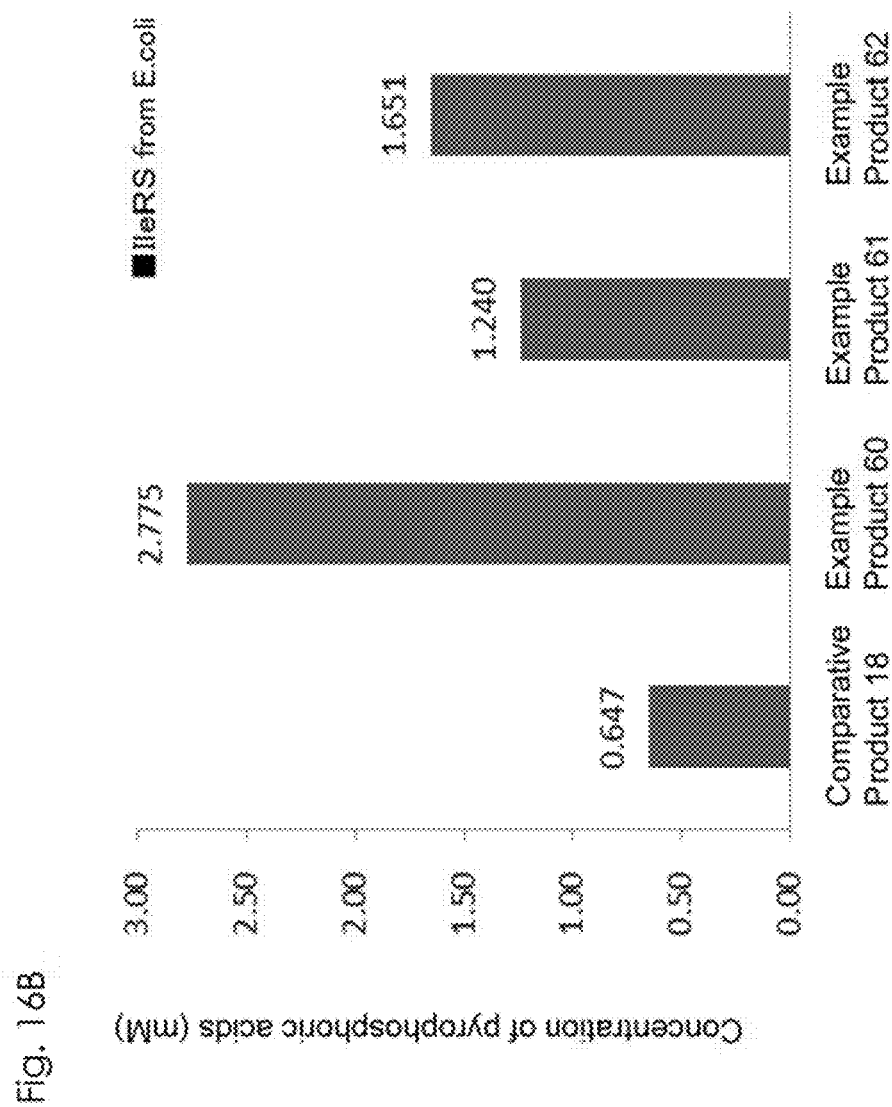

Pyrophosphoric acid of each of Example Products 57-62 and Comparative Products 17 and 18 prepared in Examples 56 and 57 was measured by the molybdenum blue method as described in Example 48. As a result, as shown in FIGS. 16A-16B, the yield of pyrophosphoric acid was increased in the case where the polar solvent was added when compared with the case where the polar solvent was not added, demonstrating that the addition of the polar solvent increased the yield of pyrophosphoric acid in the AARS reaction.
(Comparison of Yield of Pyrophosphoric Acid Using D-Amino Acids)

Example 59

200 µL of a reaction solution containing 200 mM HEPES-KOH (pH 8), 75 mM ATP, 500 mM MgCl$_2$, 50 µM of D-tyrosine and 10 µM of TyrRS (derived from *E. coli*) was prepared and treated at 50° C. for 30 minutes. After the reaction, 40 µL of trichloroacetic acid was added so that its final concentration was 4%, to terminate the reaction. After the termination of the reaction, the precipitate was removed by centrifugation to prepare Example Product 63.

Comparative Example 11

As the reaction conditions of such a low AARS concentration as 5 µM, 200 µL of a reaction solution containing 200 mM HEPES-KOH (pH 8), 40 mM ATP, 40 mM MnCl$_2$, 50 µM of D-tyrosine and 5 µM of TyrRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation to prepare Comparative Product 19.

Example 60

200 µL of a reaction solution containing 200 mM CHES-KOH (pH 9.5), 50 mM ATP, 100 mM CoCl$_2$, 50 µM of D-tryptophan and 10 µM of TrpRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation to prepare Example Product 64.

Comparative Example 12

As the reaction conditions of such a low AARS concentration as 5 µM, 200 µL of a reaction solution containing 200 mM HEPES-KOH (pH 8), 20 mM ATP, 20 mM MnCl$_2$, 50 µM of D-tryptophan and 5 µM of TrpRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation to prepare Comparative Product 20.
(Measurement of Pyrophosphoric Acid in Accordance with Molybdenum Blue Method: Comparison of Yield of Pyrophosphoric Acid)

Example 61

Figure 17A:
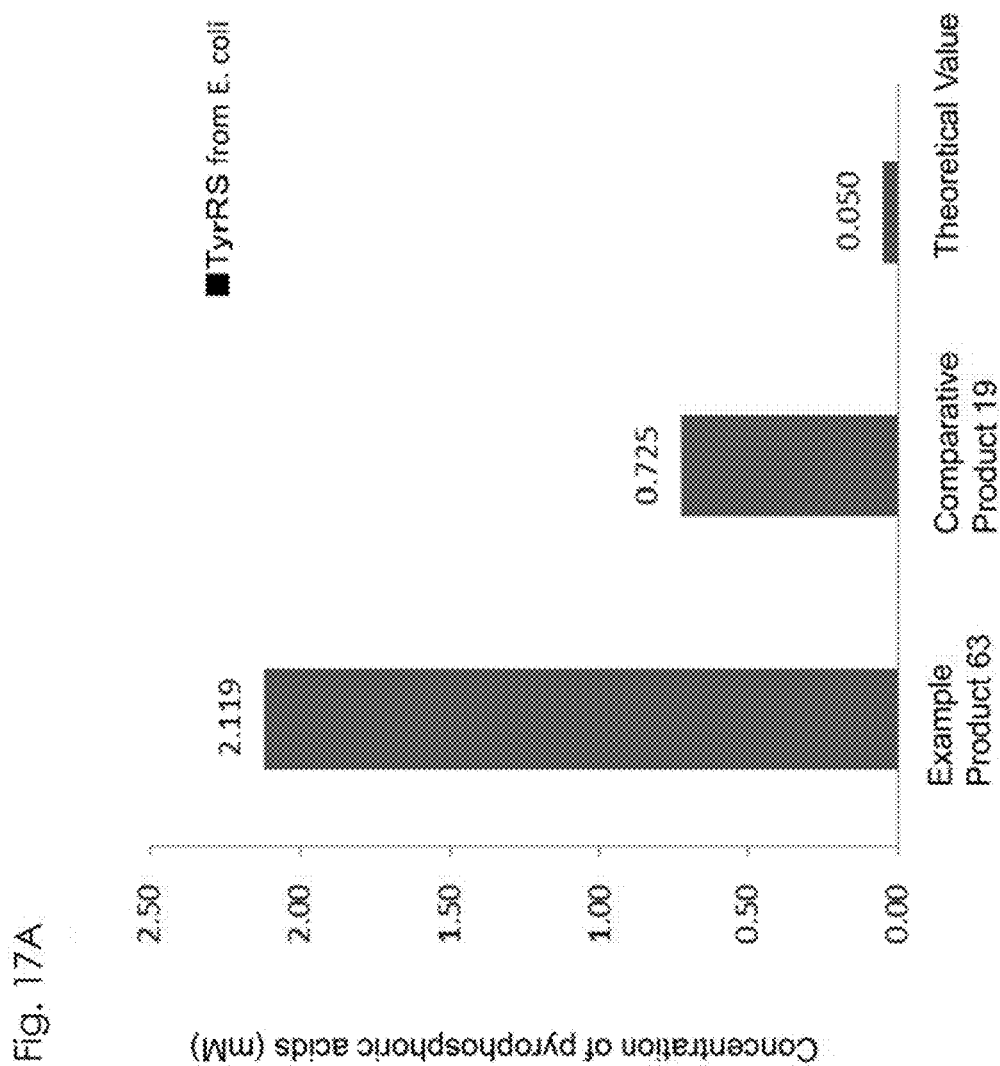
FIGS. 17A-17B illustrate comparison of yields of pyrophosphoric acids in the AARS reaction using D-amino acids between the present invention and under the condition of a low AARS concentration.
Figure 17B:
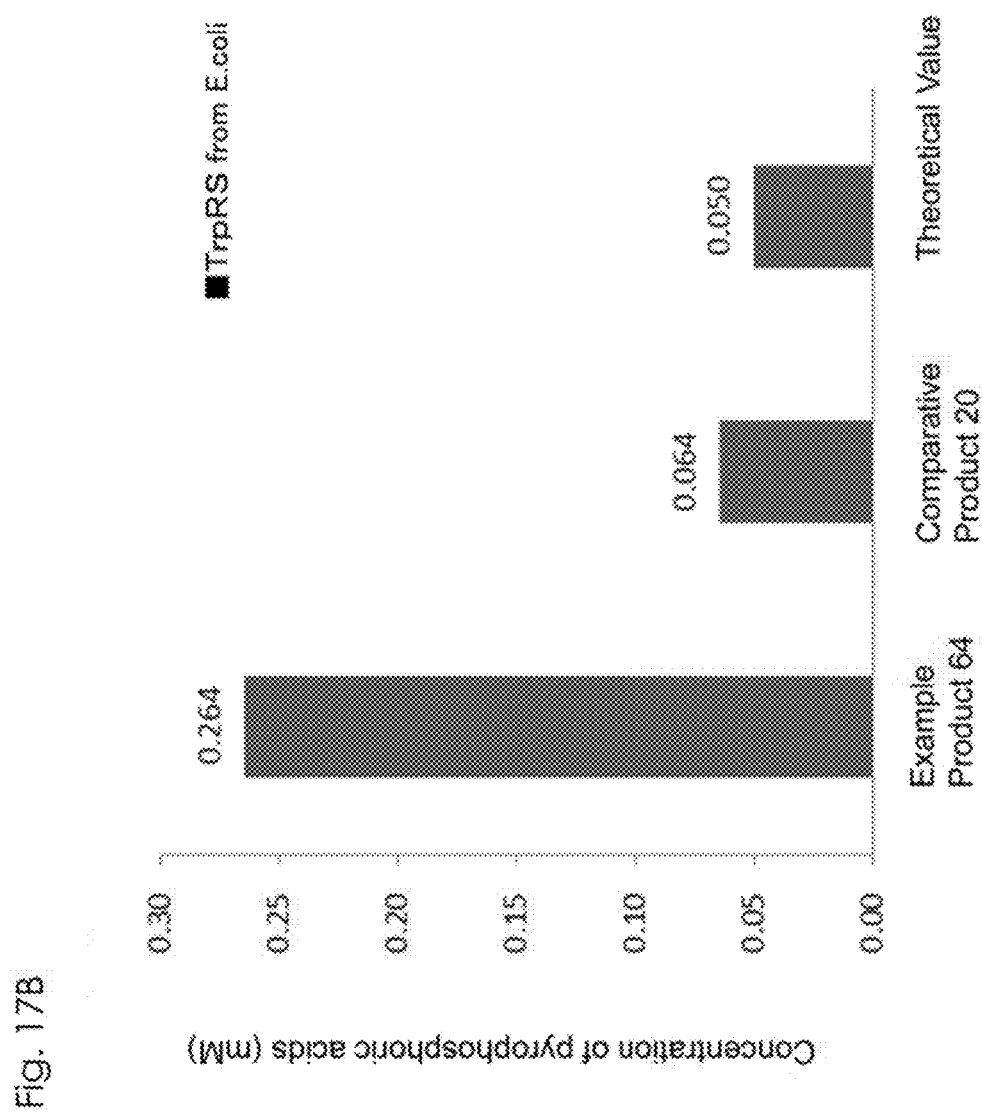

15 µL of 1 M mercaptoethanol and 60 µL of color developing liquid (2.5% ammonium molybdate/5 N sulfuric acid) were mixed in 150 µL of a reaction solution of each of Example Products 63 and 64 prepared in Examples 59 and 60, and Comparative Products 19 and 20 prepared in Comparative Examples 11 and 12, the solution was allowed to stand at room temperature for 20 minutes, and then an absorbance at 580 nm was measured. The pyrophosphoric acid concentration in the reaction solution was determined from a value obtained by subtracting the absorbance value of each sample to which water was added instead of the D-amino acid as a blank from the absorbance value of the respective sample. As a result, as shown in FIGS. 17A-17B, the pyrophosphoric acid was produced in Example Products 63 and 64 in an amount about three times or more than that in Comparative Products 19 and 20 (5 µM of AARS was used), and in an amount five times or more than the theoretical value of the pyrophosphoric acid amount produced when all of the added amino acids were used in the enzyme reaction. Thus, it was revealed that the yields of the pyrophosphoric acid could be significantly increased when compared with the comparative examples, by using the high AARS concentration, and accordingly the high ATP and/or divalent ion concentration as well in the present method.
(Comparison of Measuring Range Using D-Amino Acids)

Example 62

Figure 18A:
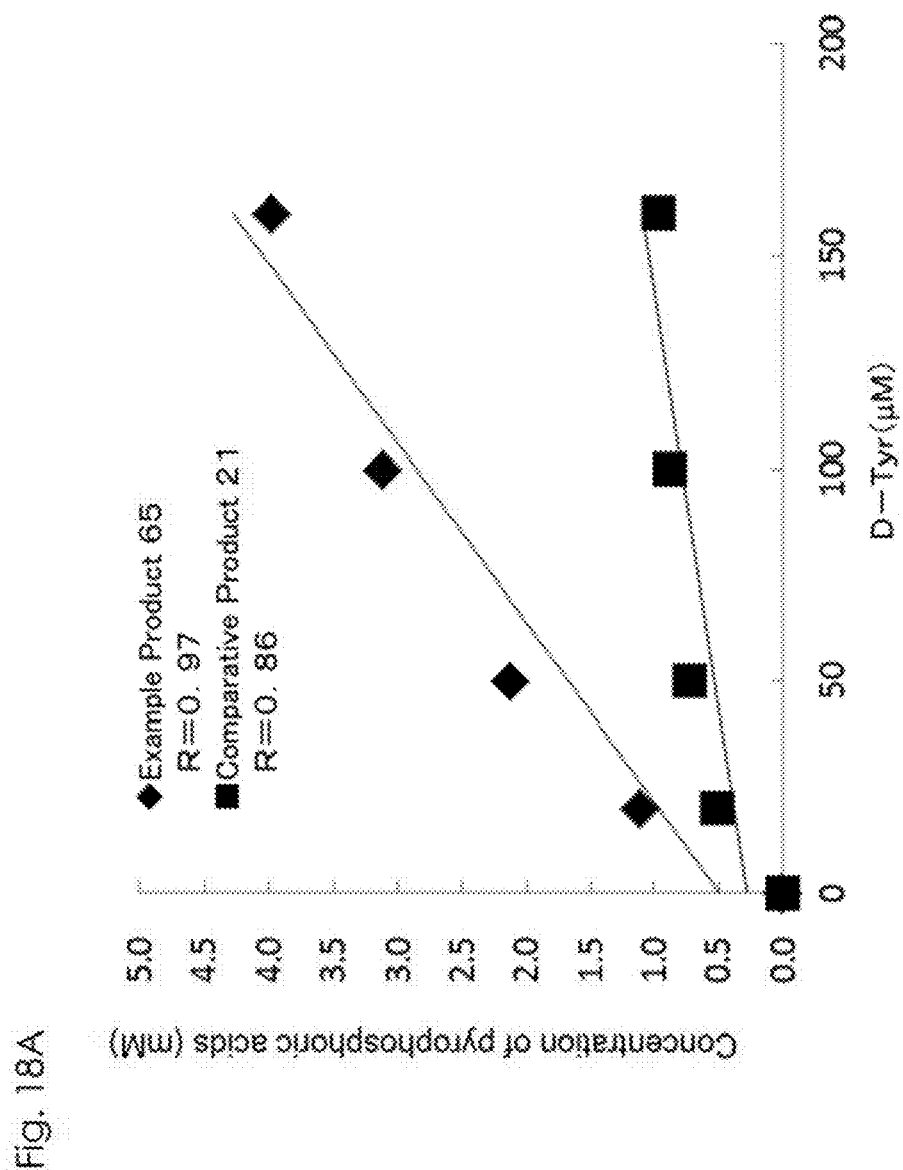
FIGS. 18A-18B illustrate calibration curves for D-amino acids in pyrophosphoric acid measurement in accordance with a molybdenum blue method.
Figure 18B:
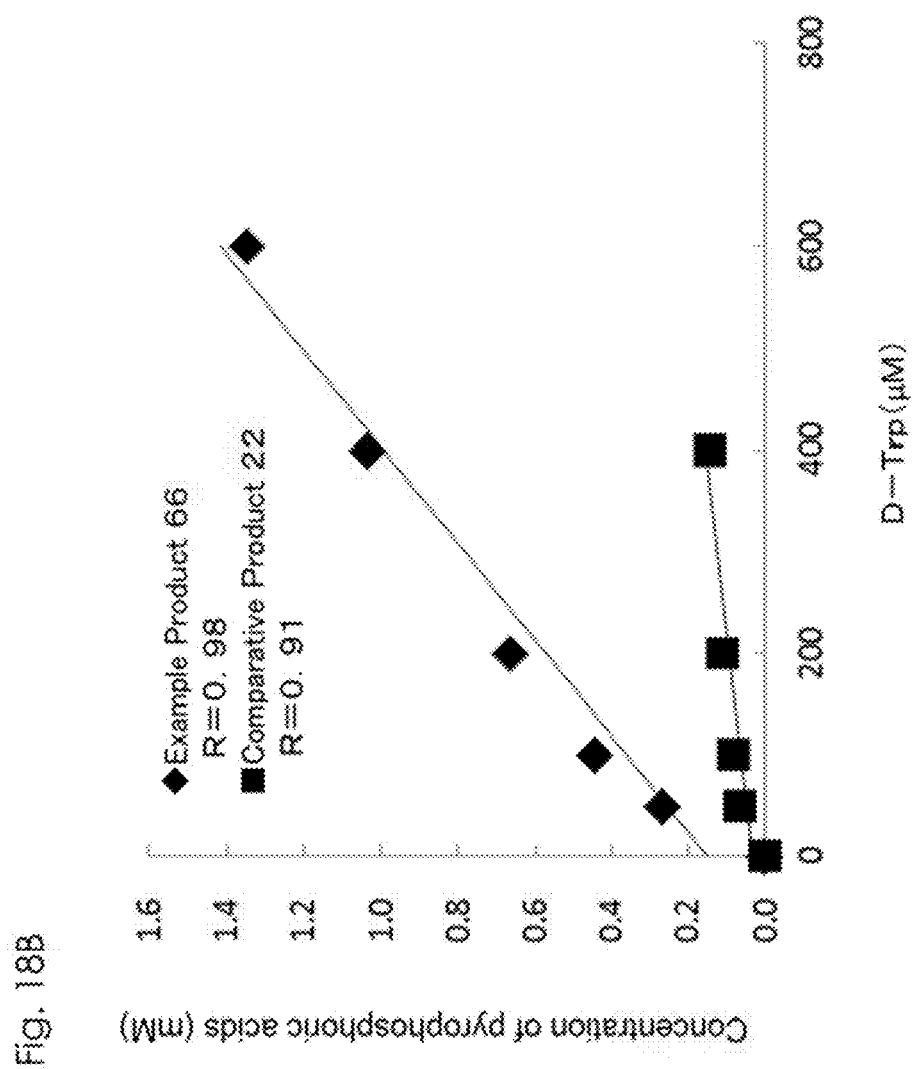

200 µL of a reaction solution containing 200 mM HEPES-KOH (pH 8), 75 mM ATP, 500 mM MgCl$_2$, 0 µM, 20 µM, 50 µM, 100 µM or 160 µM of D-tyrosine and 10 µM of TyrRS (derived from *E. coli*) was prepared and treated at 50° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Example Product 65) was measured by the molybdenum blue method as described in Example 61. On the other hand, as the reaction conditions of such a low AARS concentration as 5 µM, 200 µL a reaction solution containing 200 mM HEPES-KOH (pH 8), 40 mM ATP, 40 mM MnCl$_2$, 0 µM, 20 µM, 50 µM, 100 µM or 160 µM of of D-tyrosine and 5 µM of TyrRS (derived from *E. coli*) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Comparative Product 21) was measured by the molybdenum blue method as described in Example 61. As a result, as shown in FIGS. 18A-18B, while a correlation "R" between the amino acid concentration and the pyrophosphoric acid amount was decreased to 0.86 when measured to a higher amino acid concentration in Comparative Product 21 wherein only 5 µM of TyrRS was used, the correlation (R=0.97) was recognized over a wide range of an amino acid concentration in the present method that used 10 µM of TyrRS, and accordingly the high ATP and/or divalent ion concentration as well.

Example 63

200 µL of a reaction solution containing 200 mM CHES-KOH (pH 9.5), 50 mM ATP, 100 mM $CoCl_2$, 0 µM, 50 µM, 100 µM, 200 µM, 400 µM or 600 µM of D-tryptophan and 10 µM of TrpRS (derived from E. coli) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Example Product 66) was measured by the molybdenum blue method as described in Example 61. On the other hand, as the reaction conditions of such a low AARS concentration as 5 µM, 200 µL a reaction solution containing 200 mM HEPES-KOH (pH 8), 20 mM ATP, 20 mM $MnCl_2$, 0 µM, 50 µM, 100 µM, 200 µM or 400 µM of D-tryptophan and 5 µM of TrpRS (derived from E. coli) was prepared and treated at 40° C. for 30 minutes. After the reaction, 40 µL of trichloroacetic acid was added so that its final concentration was 4%, to terminate the reaction. After the termination of the reaction, the precipitate was removed by centrifugation and the pyrophosphoric acid in the supernatant (Comparative Product 22) was measured by the molybdenum blue method as described in Example 61. As a result, as shown in FIGS. 18A-18B, while a correlation "R" between the amino acid concentration and the pyrophosphoric acid amount was decreased to 0.91 when measured to a higher amino acid concentration in Comparative Product 22 wherein only 5 µM of TrpRS was used, the correlation (R=0.98) was recognized over a wide range of an amino acid concentration in the present method that used 10 µM of TrpRS, and accordingly the high ATP and/or divalent ion concentration as well.

As shown in Examples 44-48 and Examples 59-61, when a sample containing a relatively high amino acid (L-form and/or D-form amino acids) concentration such as about 50 µM and 100 µM was a subject to be measured, the present method produced the reaction products up to a molar number larger than that of the amino acids contained in the sample, and produced pyrophosphoric acid in an amount twice or more than that in the method wherein a low AARS concentration (5 µM) was used, showing that an amount of the reaction products could be extremely increased. As shown in Examples 49-51, the AARS reaction in the present method could produce a significantly large amount of pyrophosphoric acid. Thus, it produced pyrophosphoric acid in an amount equivalent to in a shorter time than in the method using the low AARS concentration (5 µM), revealing that the amino acids could be quantified in a short time. Furthermore, as shown in Examples 52-55, 62 and 63, the pyrophosphoric acid in the AARS would be lineally increased depending on the amino acid (L-form and/or D-form amino acids) concentration. Thus, the amino acid concentration and the pyrophosphoric acid amount were correlated with each other, so that the amino acid can be quantified in a wide range of from a low concentration to a high concentration such as 1-1,000 µM. This range is extremely wider than a range of 1-250 µM in the amino acid-quantifying method which is the high sensitive analysis by fluorometry or the like using the multistep enzymatic reaction in the prior art.

INDUSTRIAL APPLICABILITY

As described above, in the conventional amino acid quantifying method using the AARS, the amounts of the produced pyrophosphoric acid and the like were small, and thus a high-sensitivity analysis in accordance with fluorometry or the like using a multistep enzyme reaction was necessary. However, in the method of the present invention, even when only a small amount of amino acid was contained in a sample, a large amount of pyrophosphoric acid and hydrogen ions could be produced by releasing the AARS and amino acids from the formed aminoacyl AMP-AARS complex and repeatedly reusing them for formation of the aminoacyl AMP-AARS complex, and thus it was found that the high-sensitivity analysis by means of fluorometry or the like using the multistep enzyme reaction was unnecessary. Consequently, according to the present invention, it became possible to provide a method and an amino acid quantification kit for selectively and easily quantifying amino acids to be measured in a wide range of the amino acid concentration using an AARS with high sensitivity.

The invention claimed is:

1. A method for quantifying amino acids in a sample, comprising:

Step (I) comprising following steps:

(Step I-1) a step including a reaction (Reaction 1) wherein L-form and/or D-form amino acids (L-AA and/or D-AA) in the sample, an aminoacyl tRNA synthetase (AARS) corresponding to the amino acids and an adenosine triphosphate (ATP) are reacted with a divalent ion or a polyamine to form a complex comprising an aminoacyl adenylate (aminoacyl AMP) and the AARS (aminoacyl AMP-AARS complex);

(Step I-2) a step including a reaction (Reaction 2) wherein an amino acid-regenerating agent acts on the aminoacyl AMP-AARS complex formed in Reaction 1 to release the AARS and the amino acids (L-AA and/or D-AA) from the complex;

(Step I-3) a step including a reaction (Reaction 3) wherein the amino acids (L-AA and/or D-AA) and the AARS released in Reaction 2 are reused in Reaction 1 to cause the aminoacyl AMP-AARS complex reaction; and (Step I-4) a step of repeating the Step I-2 and the Step I-3, and Step (II) comprising measuring an amount of reaction products produced in the Step (I) and determining an amount of the L-form and/or D-form amino acids on the basis of the measured amount of the reaction products, wherein when Step I-2 is repeated, the amino acid-regenerating agent acts on the aminoacyl AMP-AARS complex formed in Reaction 1 or Reaction 3 to release the AARS and the amino acids (L-AA and/or D-AA) from the complex in Step (I-2) and, wherein the reaction products produced in Step (I) have a molar number that is larger than that of the amino acids in the sample.

2. The method for quantifying amino acids according to claim 1, wherein an AARS concentration in a reaction solution of Step (I) is 5.3 µM or more.

3. The method for quantifying amino acids according to claim 2, wherein the AARS concentration is in a range of 5.3 µM to 70 µM.

4. The method for quantifying amino acids according to claim 1, wherein the amino acid-regenerating agent used in Step (I) is a nucleotide and/or an alkaline compound.

5. The method for quantifying amino acids according to claim 1, wherein a polar solvent is added into Step (I).

6. The method for quantifying amino acids according to claim 1, wherein an amino acid concentration in the sample is in a range of 300 µM to 1,000 µM.

7. The method for quantifying amino acids according to claim 1, wherein the amount of the reaction products produced in the Step (I) is measured by measuring potential change by an ion-sensitive field effect transistor, a glass electrode membrane or a multielectrode electrometer.

8. The method for quantifying amino acids according claim 1, wherein the amount of the reaction products produced in the Step (I) is measured by measuring change in absorbance in accordance with absorptiometry.

9. The method for quantifying amino acids according to claim 1, wherein at least one of a pyrophosphoric acid and hydrogen ion is measured as the reaction products produced in the Step (I).

10. The method for quantifying amino acids according to claim 1, wherein either one of the L-form and D-form amino acids in the sample is removed as a pretreatment prior to Step (I).

* * * * *

SEQUENCE LISTING

```
<160> NUMBER OF SEQ ID NOS: 11

<210> SEQ ID NO 1
<211> LENGTH: 420
<212> TYPE: PRT
<213> ORGANISM: Thermotoga maritima MSB8
<220> FEATURE:
<223> OTHER INFORMATION: HisRS

<400> SEQUENCE: 1

Met Lys Tyr Arg Arg Ile Lys Gly Thr Asn Asp Ile Phe Gly Glu Glu
1               5                   10                  15

Ile Trp Tyr Trp Arg Tyr Val Glu Glu Thr Phe Arg Asn Val Cys Glu
            20                  25                  30
```

Ser Ala Gly Ile Glu Glu Ile Arg Thr Pro Ile Phe Glu Gln Thr Glu
     35                  40                  45

Leu Phe Val Arg Ser Val Gly Glu Glu Ser Asp Ile Val Gln Lys Glu
     50                  55                  60

Met Tyr Thr Phe Gln Asp Lys Ala Gly Arg Ser Ile Thr Leu Arg Pro
 65                  70                  75                  80

Glu Gly Thr Ala Pro Val Val Arg Ala Phe Leu Glu Asn Ser Leu Ile
                 85                  90                  95

Asp Arg Gly Phe Gln Gln Arg Tyr Tyr Ile Gly Pro Met Phe Arg
                100                 105                 110

Tyr Glu Lys Pro Gln Ser Gly Arg Leu Arg Gln Phe His Gln Val Gly
         115                 120                 125

Phe Glu Ile Ile Gly Pro Glu Ser Pro Lys Ala Asp Phe Glu Val Ile
         130                 135                 140

Met Leu Val Asp Thr Phe Leu Arg Arg Leu Gly Leu Thr Lys Tyr Lys
145                 150                 155                 160

Ile His Leu Asn Ser Ile Gly Cys Pro Val Cys Arg Lys Asn Tyr Arg
                165                 170                 175

Glu Ala Leu Lys Glu Tyr Tyr Gly Arg Ile Leu Asp Asn Leu Cys Asp
             180                 185                 190

Asp Cys Lys Arg Arg Tyr Glu Thr Asn Ile Leu Arg Leu Leu Asp Cys
             195                 200                 205

Lys Val Asp His Glu Tyr Ser Leu Asn Ala Pro Lys Ser Val Asp Tyr
         210                 215                 220

Leu Cys Asp Ser Cys Arg Ala His Tyr Lys Lys Leu Lys Glu Tyr Leu
225                 230                 235                 240

Asn Thr Phe Glu Ile Glu Tyr Val Glu Asp His Thr Leu Val Arg Gly
                245                 250                 255

Leu Asp Tyr Tyr Thr Arg Thr Val Phe Glu Val Arg His Glu Gly Leu
             260                 265                 270

Gly Ala Gln Ser Ala Ile Ala Gly Gly Gly Arg Tyr Asp Gly Leu Phe
         275                 280                 285

Ala Glu Leu Gly Gly Ser Ser Val Pro Ala Leu Gly Phe Ala Gly Gly
         290                 295                 300

Ile Glu Arg Ile Ile Leu Ala Leu Lys Ala Glu Gly Ile Glu Ile Pro
305                 310                 315                 320

Met Lys Asn Val His Leu Val Tyr Ile Ala Thr Leu Gly Glu Lys Ala
                325                 330                 335

Phe Met Asp Gly Val Arg Leu Ala Gly Glu Leu Arg Lys Lys Gly Leu
             340                 345                 350

Ser Val Asp Val Asp Ile Met Asp Arg Lys Leu Ser Gly Gln Leu Lys
         355                 360                 365

His Ala Ser Arg Met Gly Ser Arg Tyr Ala Val Ile Ile Gly Asp Glu
     370                 375                 380

Glu Leu Glu Lys Gly Ile Val Ile Leu Arg Asp Leu Glu Thr Gly Asp
385                 390                 395                 400

Gln Val Glu Ile Asp Arg Asp Phe Ala Ala Asp Tyr Ile Ala Glu Arg
                405                 410                 415

Val Ser Lys Asp
             420

<210> SEQ ID NO 2
<211> LENGTH: 425

```
<212> TYPE: PRT
<213> ORGANISM: Thermotoga maritima MSB8
<220> FEATURE:
<223> OTHER INFORMATION: SerRS

<400> SEQUENCE: 2
```

| | | | | | | | | | | | | | | |
|---|---|---|---|---|---|---|---|---|---|---|---|---|---|---|
| Met | Ile | Asp | Ile | Lys | Leu | Ile | Arg | Gln | Asn | Pro | Asp | Phe | Val | Lys | Glu |
| 1 | | | | 5 | | | | | 10 | | | | | 15 | |
| Ala | Leu | Arg | Lys | Arg | Gly | Glu | Asp | Pro | Ala | Ile | Ile | Asp | Glu | Ile | Leu |
| | | | 20 | | | | | 25 | | | | | 30 | | |
| Lys | Ile | Asp | Ala | Asp | Trp | Arg | Ala | Thr | Ile | Thr | Lys | Thr | Asn | Glu | Leu |
| | | 35 | | | | | 40 | | | | | 45 | | | |
| Arg | Ser | Arg | Arg | Asn | Glu | Ile | Ser | Lys | Asn | Val | Ala | Arg | Leu | Lys | Lys |
| | 50 | | | | | 55 | | | | | 60 | | | | |
| Glu | Gly | Lys | Asn | Ala | Glu | Ala | Glu | Ala | Leu | Ile | Glu | Glu | Gly | Lys | Arg |
| 65 | | | | 70 | | | | 75 | | | | | 80 | | |
| Leu | Gly | Glu | Glu | Ile | Lys | Ala | Leu | Glu | Glu | Lys | Glu | Lys | Glu | Leu | Gln |
| | | | | 85 | | | | | 90 | | | | | 95 | |
| Lys | Lys | Leu | Asn | Asp | Leu | Leu | Leu | Met | Ile | Pro | Asn | Ile | Pro | His | Glu |
| | | | 100 | | | | | 105 | | | | | 110 | | |
| Ser | Val | Pro | Val | Gly | Glu | Asp | Glu | Ser | Gln | Asn | Val | Gly | Val | Arg | Arg |
| | | 115 | | | | | 120 | | | | | 125 | | | |
| Trp | Gly | Glu | Pro | Arg | Glu | Phe | Asp | Phe | Thr | Pro | Leu | Ala | His | Trp | Asp |
| 130 | | | | | | 135 | | | | | 140 | | | | |
| Leu | Gly | Pro | Ala | Trp | Gly | Leu | Met | Asp | Phe | Ser | Arg | Ala | Ser | Lys | Leu |
| 145 | | | | | 150 | | | | | 155 | | | | | 160 |
| Ser | Gly | Ser | Arg | Phe | Thr | Val | Met | Tyr | Gly | Lys | Leu | Ala | Arg | Leu | Glu |
| | | | | 165 | | | | | 170 | | | | | 175 | |
| Arg | Ala | Leu | Ile | Asn | Phe | Met | Leu | Asp | Val | His | Thr | Lys | Glu | His | Gly |
| | | | 180 | | | | | 185 | | | | | 190 | | |
| Tyr | Thr | Glu | Val | Trp | Val | Pro | His | Leu | Val | Lys | Arg | Glu | Thr | Ile | Thr |
| | | 195 | | | | | 200 | | | | | 205 | | | |
| Ile | Thr | Gly | Gln | Leu | Pro | Lys | Phe | Glu | Glu | Glu | Leu | Tyr | Leu | Ala | Glu |
| 210 | | | | | 215 | | | | | 220 | | | | | |
| Arg | Asp | Asp | Leu | Phe | Leu | Ile | Pro | Thr | Ala | Glu | Val | Pro | Leu | Ala | Ala |
| 225 | | | | | 230 | | | | | 235 | | | | | 240 |
| Leu | His | Ser | Gly | Glu | Ile | Leu | Glu | Glu | Lys | Glu | Leu | Pro | Lys | Lys | Tyr |
| | | | | 245 | | | | | 250 | | | | | 255 | |
| Val | Ser | Tyr | Thr | Pro | Cys | Tyr | Arg | Arg | Glu | Ala | Gly | Ser | Tyr | Gly | Lys |
| | | | 260 | | | | | 265 | | | | | 270 | | |
| Asp | Val | Arg | Gly | Met | Ile | Arg | Gln | His | Gln | Phe | Asp | Lys | Val | Glu | Leu |
| | | 275 | | | | | 280 | | | | | 285 | | | |
| Val | Trp | Val | Thr | Thr | Pro | Glu | Arg | Ser | Phe | Glu | Asp | Leu | Glu | Glu | Leu |
| 290 | | | | | 295 | | | | | 300 | | | | | |
| Val | Lys | Asp | Ala | Glu | Thr | Ile | Leu | Arg | Lys | Leu | Glu | Leu | Pro | Tyr | Arg |
| 305 | | | | | 310 | | | | | 315 | | | | | 320 |
| Val | Val | Ser | Leu | Cys | Thr | Gly | Asp | Leu | Gly | Phe | Thr | Ser | Ala | Lys | Thr |
| | | | | 325 | | | | | 330 | | | | | 335 | |
| Tyr | Asp | Ile | Glu | Val | Trp | Leu | Pro | Ser | Tyr | Asn | Ala | Tyr | Lys | Glu | Ile |
| | | | 340 | | | | | 345 | | | | | 350 | | |
| Ser | Ser | Cys | Ser | Asn | Val | Thr | Asp | Phe | Gln | Ala | Arg | Arg | Gly | Asn | Met |
| | | 355 | | | | | 360 | | | | | 365 | | | |
| Arg | Tyr | Arg | Arg | Arg | Ser | Asp | Gly | Lys | Leu | Glu | Tyr | Val | His | Thr | Leu |
| 370 | | | | | 375 | | | | | 380 | | | | | |

```
Asn Gly Ser Gly Ile Ala Val Gly Arg Ala Leu Val Ala Ile Leu Glu
385                 390                 395                 400

Asn Tyr Gln Gln Pro Asp Gly Ser Val Arg Val Pro Glu Val Leu Val
                405                 410                 415

Pro Tyr Thr Gly Phe Glu Val Ile Pro
                420                 425

<210> SEQ ID NO 3
<211> LENGTH: 328
<212> TYPE: PRT
<213> ORGANISM: Thermotoga maritima MSB8
<220> FEATURE:
<223> OTHER INFORMATION: TrpRS

<400> SEQUENCE: 3

Met Arg Ile Leu Ser Gly Met Arg Pro Thr Gly Lys Leu His Ile Gly
1               5                   10                  15

His Leu Val Gly Ala Leu Glu Asn Trp Val Lys Leu Gln Glu Glu Gly
                20                  25                  30

Asn Glu Cys Phe Tyr Phe Val Ala Asp Trp His Ala Leu Thr Thr His
                35                  40                  45

Tyr Asp Asp Val Ser Lys Leu Lys Glu Tyr Thr Arg Asp Leu Val Arg
50                  55                  60

Gly Phe Leu Ala Cys Gly Ile Asp Pro Glu Lys Ser Val Ile Phe Val
65                  70                  75                  80

Gln Ser Gly Val Lys Glu His Ala Glu Leu Ala Leu Leu Phe Ser Met
                85                  90                  95

Ile Val Ser Val Ser Arg Leu Glu Arg Val Pro Thr Tyr Lys Glu Ile
                100                 105                 110

Lys Ser Glu Leu Asn Tyr Lys Asp Leu Ser Thr Ala Gly Phe Leu Ile
                115                 120                 125

Tyr Pro Val Leu Gln Ala Ala Asp Ile Leu Ile Tyr Lys Ala Glu Gly
                130                 135                 140

Val Pro Val Gly Glu Asp Gln Val Tyr His Ile Glu Leu Thr Arg Glu
145                 150                 155                 160

Ile Ala Arg Arg Phe Asn Tyr Leu Tyr Asp Glu Val Phe Pro Glu Pro
                165                 170                 175

Glu Ala Ile Leu Ser Arg Val Pro Lys Leu Pro Gly Thr Asp Gly Arg
                180                 185                 190

Lys Met Ser Lys Ser Tyr Gly Asn Ile Ile Asn Leu Glu Ile Ser Glu
                195                 200                 205

Lys Glu Leu Glu Gln Thr Ile Leu Arg Met Met Thr Asp Pro Ala Arg
                210                 215                 220

Val Arg Arg Ser Asp Pro Gly Asn Pro Glu Asn Cys Pro Val Trp Lys
225                 230                 235                 240

Tyr His Gln Ala Phe Asp Ile Ser Glu Glu Ser Lys Trp Val Trp
                245                 250                 255

Glu Gly Cys Thr Thr Ala Ser Ile Gly Cys Val Asp Cys Lys Lys Leu
                260                 265                 270

Leu Leu Lys Asn Met Lys Arg Lys Leu Ala Pro Ile Trp Glu Asn Phe
                275                 280                 285

Arg Lys Ile Asp Glu Asp Pro His Tyr Val Asp Val Ile Met Glu
                290                 295                 300

Gly Thr Lys Lys Ala Arg Glu Val Ala Ala Lys Thr Met Glu Glu Val
305                 310                 315                 320
```

```
Arg Arg Ala Met Asn Leu Met Phe
                325

<210> SEQ ID NO 4
<211> LENGTH: 492
<212> TYPE: PRT
<213> ORGANISM: Thermus thermophilus HB8
<220> FEATURE:
<223> OTHER INFORMATION: LysRS

<400> SEQUENCE: 4

Met Asn Asp Gln Thr Arg Gln Arg Leu Leu Asn Leu Glu Ala Leu Val
1               5                   10                  15

Glu Ala Gly Phe Ala Pro Tyr Pro Tyr Arg Phe Pro Lys Thr His Ser
            20                  25                  30

Ala Glu Ala Ile Leu Lys Ala Lys Arg Gly Ala Pro Pro Glu Ser Glu
        35                  40                  45

Trp Pro Glu Glu Val Ala Val Ala Gly Arg Leu Val Ala Leu Arg
    50                  55                  60

Arg Met Gly Lys Val Thr Phe Ala His Leu Leu Asp Glu Thr Gly Arg
65                  70                  75                  80

Ile Gln Leu Tyr Phe Gln Arg Asp Leu Thr Pro Lys Tyr Glu Leu Leu
                85                  90                  95

Lys Lys Leu Asp Val Gly Asp Ile Leu Gly Val Arg Gly His Pro Phe
            100                 105                 110

Thr Thr Lys Thr Gly Glu Val Thr Val Lys Val Leu Asp Trp Thr Pro
        115                 120                 125

Leu Val Lys Ser Leu His Pro Leu Pro Asp Lys Trp His Gly Leu Arg
    130                 135                 140

Asp Lys Glu Val Arg Tyr Arg Gln Arg Tyr Leu Asp Leu Ile Val Asn
145                 150                 155                 160

Pro Glu Val Arg Glu Val Phe Arg Arg Ser Glu Ile Val Arg Tyr
                165                 170                 175

Ile Arg Arg Phe Phe Glu Ala Lys Gly Phe Leu Glu Val Glu Thr Pro
            180                 185                 190

Ile Leu Gln Pro Thr Thr Gly Gly Ala Glu Ala Arg Pro Phe Lys Thr
        195                 200                 205

Tyr His Asn Ala Leu Asp His Glu Phe Tyr Leu Arg Ile Ser Leu Glu
    210                 215                 220

Leu Tyr Leu Lys Arg Leu Leu Val Gly Gly Tyr Glu Lys Val Phe Glu
225                 230                 235                 240

Ile Gly Arg Asn Phe Arg Asn Glu Gly Ile Asp His Asn His Asn Pro
                245                 250                 255

Glu Phe Thr Met Leu Glu Ala Tyr Trp Ala Tyr Ala Asp Tyr Gln Asp
            260                 265                 270

Met Ala Gly Leu Val Glu Glu Leu Leu Ser Gly Leu Val Leu His Leu
        275                 280                 285

Phe Gly Ser His Glu Val Pro Tyr Gln Gly Arg Val Leu Asn Phe Lys
    290                 295                 300

Pro Pro Phe Arg Arg Ile Ser Phe Val Glu Ala Leu Lys Glu Lys Ala
305                 310                 315                 320

Gly Leu Pro Phe Asp Pro Leu Asp Leu Glu Arg Leu Arg Leu Trp Ala
                325                 330                 335

Asp Ala His His Pro Glu Leu Ser Gln Val Pro Asn Tyr Lys Leu Leu
            340                 345                 350
```

Asp Lys Leu Phe Gly Ile Tyr Val Glu Pro Glu Leu Gln Asp Pro Thr
        355                 360                 365

Phe Val Phe Asp Phe Pro Leu Ala Ile Ser Pro Leu Ala Lys Arg His
370                 375                 380

Arg Glu Lys Pro Gly Leu Val Glu Arg Trp Asp Leu Tyr Ala Gly Gly
385                 390                 395                 400

Met Glu Leu Ala Pro Cys Tyr Ser Glu Leu Asn Asp Pro Leu Asp Gln
                405                 410                 415

Arg Glu Arg Phe Leu Glu Gln Ala Arg Arg Lys Glu Gly Asp Glu
            420                 425                 430

Glu Ala Pro Glu Pro Asp Glu Asp Phe Leu Leu Ala Leu Glu Tyr Gly
            435                 440                 445

Met Pro Pro Ala Ala Gly Leu Gly Leu Gly Ile Asp Arg Leu Ala Met
450                 455                 460

Leu Leu Thr Asp Gln Pro Ser Leu Arg Asp Val Leu Leu Phe Pro Leu
465                 470                 475                 480

Leu Lys Pro Lys Lys Glu Ala Val Glu Glu Gly Val
                485                 490

<210> SEQ ID NO 5
<211> LENGTH: 424
<212> TYPE: PRT
<213> ORGANISM: Escherichia coli NBRC3992
<220> FEATURE:
<223> OTHER INFORMATION: TyrRS

<400> SEQUENCE: 5

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

```
Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 6
<211> LENGTH: 951
<212> TYPE: PRT
<213> ORGANISM: Escherichia coli NBRC3992
<220> FEATURE:
<223> OTHER INFORMATION: ValRS

<400> SEQUENCE: 6

Met Glu Lys Thr Tyr Asn Pro Gln Asp Ile Glu Gln Pro Leu Tyr Glu
1               5                   10                  15

His Trp Glu Lys Gln Gly Tyr Phe Lys Pro Asn Gly Asp Glu Ser Gln
            20                  25                  30

Glu Ser Phe Cys Ile Met Ile Pro Pro Pro Asn Val Thr Gly Ser Leu
        35                  40                  45

His Met Gly His Ala Phe Gln Gln Thr Ile Met Asp Thr Met Ile Arg
    50                  55                  60

Tyr Gln Arg Met Gln Gly Lys Asn Thr Leu Trp Gln Val Gly Thr Asp
65                  70                  75                  80

His Ala Gly Ile Ala Thr Gln Met Val Val Glu Arg Lys Ile Ala Ala
                85                  90                  95

Glu Glu Gly Lys Thr Arg His Asp Tyr Gly Arg Glu Ala Phe Ile Asp
            100                 105                 110

Lys Ile Trp Glu Trp Lys Ala Glu Ser Gly Gly Thr Ile Thr Arg Gln
        115                 120                 125

Met Arg Arg Leu Gly Asn Ser Val Asp Trp Glu Arg Glu Arg Phe Thr
    130                 135                 140

Met Asp Glu Gly Leu Ser Asn Ala Val Lys Glu Val Phe Val Arg Leu
145                 150                 155                 160
```

-continued

Tyr Lys Glu Asp Leu Ile Tyr Arg Gly Lys Arg Leu Val Asn Trp Asp
            165                 170                 175
Pro Lys Leu Arg Thr Ala Ile Ser Asp Leu Glu Val Glu Asn Arg Glu
        180                 185                 190
Ser Lys Gly Ser Met Trp His Ile Arg Tyr Pro Leu Ala Asp Gly Ala
    195                 200                 205
Lys Thr Ala Asp Gly Lys Asp Tyr Leu Val Val Ala Thr Thr Arg Pro
210                 215                 220
Glu Thr Leu Leu Gly Asp Thr Gly Val Ala Val Asn Pro Glu Asp Pro
225                 230                 235                 240
Arg Tyr Lys Asp Leu Ile Gly Lys Tyr Val Ile Leu Pro Leu Val Asn
            245                 250                 255
Arg Arg Ile Pro Ile Val Gly Asp Glu His Ala Asp Met Glu Lys Gly
        260                 265                 270
Thr Gly Cys Val Lys Ile Thr Pro Ala His Asp Phe Asn Asp Tyr Glu
    275                 280                 285
Val Gly Lys Arg His Ala Leu Pro Met Ile Asn Ile Leu Thr Phe Asp
290                 295                 300
Gly Asp Ile Arg Glu Ser Ala Gln Val Phe Asp Thr Lys Gly Asn Glu
305                 310                 315                 320
Ser Asp Val Tyr Ser Ser Glu Ile Pro Ala Glu Phe Gln Lys Leu Glu
            325                 330                 335
Arg Phe Ala Ala Arg Lys Ala Val Ala Ala Val Asp Ala Leu Gly
        340                 345                 350
Leu Leu Glu Glu Ile Lys Pro His Asp Leu Thr Val Pro Tyr Gly Asp
    355                 360                 365
Arg Gly Gly Val Val Ile Glu Pro Met Leu Thr Asp Gln Trp Tyr Val
370                 375                 380
Arg Ala Asp Val Leu Ala Lys Pro Ala Val Glu Ala Val Glu Asn Gly
385                 390                 395                 400
Asp Ile Gln Phe Val Pro Lys Gln Tyr Glu Asn Met Tyr Phe Ser Trp
            405                 410                 415
Met Arg Asp Ile Gln Asp Trp Cys Ile Ser Arg Gln Leu Trp Trp Gly
        420                 425                 430
His Arg Ile Pro Ala Trp Tyr Asp Glu Ala Gly Asn Val Tyr Val Gly
    435                 440                 445
Arg Asn Glu Asp Glu Val Arg Lys Glu Asn Asn Leu Gly Ala Asp Val
450                 455                 460
Val Leu Arg Gln Asp Glu Asp Val Leu Asp Thr Trp Phe Ser Ser Ala
465                 470                 475                 480
Leu Trp Thr Phe Ser Thr Leu Gly Trp Pro Glu Asn Thr Asp Ala Leu
            485                 490                 495
Arg Gln Phe His Pro Thr Ser Val Met Val Ser Gly Phe Asp Ile Ile
        500                 505                 510
Phe Phe Trp Ile Ala Arg Met Ile Met Thr Met His Phe Ile Lys
    515                 520                 525
Asp Glu Asn Gly Lys Pro Gln Val Pro Phe His Thr Val Tyr Met Thr
530                 535                 540
Gly Leu Ile Arg Asp Asp Glu Gly Gln Lys Met Ser Lys Ser Lys Gly
545                 550                 555                 560
Asn Val Ile Asp Pro Leu Asp Met Val Asp Gly Ile Ser Leu Pro Glu
            565                 570                 575
Leu Leu Glu Lys Arg Thr Gly Asn Met Met Gln Pro Gln Leu Ala Asp

```
                580             585             590
Lys Ile Arg Lys Arg Thr Glu Lys Gln Phe Pro Asn Gly Ile Glu Pro
            595                 600             605

His Gly Thr Asp Ala Leu Arg Phe Thr Leu Ala Ala Leu Ala Ser Thr
610             615                 620

Gly Arg Asp Ile Asn Trp Asp Met Lys Arg Leu Gly Tyr Arg Asn
625             630              635                  640

Phe Cys Asn Lys Leu Trp Asn Ala Ser Arg Phe Val Leu Met Asn Thr
            645             650                 655

Glu Gly Gln Asp Cys Gly Phe Asn Gly Gly Glu Met Thr Leu Ser Leu
            660             665                 670

Ala Asp Arg Trp Ile Leu Ala Glu Phe Asn Gln Thr Ile Lys Ala Tyr
            675             680                 685

Arg Glu Ala Leu Asp Ser Phe Arg Phe Asp Ile Ala Ala Gly Ile Leu
            690             695                 700

Tyr Glu Phe Thr Trp Asn Gln Phe Cys Asp Trp Tyr Leu Glu Leu Thr
705             710                 715                 720

Lys Pro Val Met Asn Gly Gly Thr Glu Ala Glu Leu Arg Gly Thr Arg
                725             730                 735

His Thr Leu Val Thr Val Leu Glu Gly Leu Leu Arg Leu Ala His Pro
                740             745                 750

Ile Ile Pro Phe Ile Thr Glu Thr Ile Trp Gln Arg Val Lys Val Leu
            755             760                 765

Cys Gly Ile Thr Ala Asp Thr Ile Met Leu Gln Pro Phe Pro Gln Tyr
            770             775                 780

Asp Ala Ser Gln Val Asp Glu Ala Ala Leu Ala Asp Thr Glu Trp Leu
785             790                 795                 800

Lys Gln Ala Ile Val Ala Val Arg Asn Ile Arg Ala Glu Met Asn Ile
                805             810                 815

Ala Pro Gly Lys Pro Leu Glu Leu Leu Leu Arg Gly Cys Ser Ala Asp
            820             825                 830

Ala Glu Arg Arg Val Asn Glu Asn Arg Gly Phe Leu Gln Thr Leu Ala
            835             840                 845

Arg Leu Glu Ser Ile Thr Val Leu Pro Ala Asp Asp Lys Gly Pro Val
850             855                 860

Ser Val Thr Lys Ile Ile Asp Gly Ala Glu Leu Leu Ile Pro Met Ala
865             870                 875                 880

Gly Leu Ile Asn Lys Glu Asp Glu Leu Ala Arg Leu Ala Lys Glu Val
            885             890                 895

Ala Lys Ile Glu Gly Glu Ile Ser Arg Ile Glu Asn Lys Leu Ala Asn
            900             905                 910

Glu Gly Phe Val Ala Arg Ala Pro Glu Ala Val Ile Ala Lys Glu Arg
            915             920                 925

Glu Lys Leu Glu Gly Tyr Ala Glu Ala Lys Ala Lys Leu Ile Glu Gln
            930             935                 940

Gln Ala Val Ile Ala Ala Leu
945             950

<210> SEQ ID NO 7
<211> LENGTH: 334
<212> TYPE: PRT
<213> ORGANISM: Escherichia coli NBRC3992
<220> FEATURE:
<223> OTHER INFORMATION: TrpRS
```

<400> SEQUENCE: 7

```
Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
            20                  25                  30

Asp Tyr His Cys Ile Tyr Cys Ile Val Asp Gln His Ala Ile Thr
        35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
            100                 105                 110

Lys Ser Ala Arg Tyr Ala Glu Asn Ile Asn Ala Gly Leu Phe Asp Tyr
        115                 120                 125

Pro Val Leu Met Ala Ala Asp Ile Leu Leu Tyr Gln Thr Asn Leu Val
    130                 135                 140

Pro Val Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
            180                 185                 190

Thr Lys Lys Met Ser Lys Ser Asp Asp Asn Arg Asn Asn Val Ile Gly
        195                 200                 205

Leu Leu Glu Asp Pro Lys Ser Val Val Lys Ile Lys Arg Ala Val
    210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
            260                 265                 270

Leu Lys Gly Glu Val Ala Asp Ala Val Ser Gly Met Leu Thr Glu Leu
        275                 280                 285

Gln Glu Arg Tyr His Arg Phe Arg Asn Asp Glu Ala Phe Leu Gln Gln
    290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330
```

<210> SEQ ID NO 8
<211> LENGTH: 938
<212> TYPE: PRT
<213> ORGANISM: Escherichia coli NBRC3992
<220> FEATURE:
<223> OTHER INFORMATION: IleRS

<400> SEQUENCE: 8

```
Met Ser Asp Tyr Lys Ser Thr Leu Asn Leu Pro Glu Thr Gly Phe Pro
1               5                   10                  15

Met Arg Gly Asp Leu Ala Lys Arg Glu Pro Gly Met Leu Ala Arg Trp
```

-continued

```
                20                  25                  30
Thr Asp Asp Leu Tyr Gly Ile Ile Arg Ala Ala Lys Gly Lys
            35                  40                  45
Lys Thr Phe Ile Leu His Asp Gly Pro Tyr Ala Asn Gly Ser Ile
        50                  55                  60
His Ile Gly His Ser Val Asn Lys Ile Leu Lys Asp Ile Val Lys
 65                  70                  75                  80
Ser Lys Gly Leu Ser Gly Tyr Asp Ser Pro Tyr Val Pro Gly Trp Asp
            85                  90                  95
Cys His Gly Leu Pro Ile Glu Leu Lys Val Glu Gln Glu Tyr Gly Lys
                100                 105                 110
Pro Gly Glu Lys Phe Thr Ala Ala Glu Phe Arg Ala Lys Cys Arg Glu
            115                 120                 125
Tyr Ala Ala Thr Gln Val Asp Gly Gln Arg Lys Asp Phe Ile Arg Leu
        130                 135                 140
Gly Val Leu Gly Asp Trp Ser His Pro Tyr Leu Thr Met Asp Phe Lys
145                 150                 155                 160
Thr Glu Ala Asn Ile Ile Arg Ala Leu Gly Lys Ile Ile Gly Asn Gly
                165                 170                 175
His Leu His Lys Gly Ala Lys Pro Val His Trp Cys Val Asp Cys Arg
            180                 185                 190
Ser Ala Leu Ala Glu Ala Glu Val Glu Tyr Tyr Asp Lys Thr Ser Pro
        195                 200                 205
Ser Ile Asp Val Ala Phe Gln Ala Val Asp Gln Asp Ala Leu Lys Ala
    210                 215                 220
Lys Phe Ala Val Ser Asn Val Asn Gly Pro Ile Ser Leu Val Ile Trp
225                 230                 235                 240
Thr Thr Thr Pro Trp Thr Leu Pro Ala Asn Arg Ala Ile Ser Ile Ala
                245                 250                 255
Pro Asp Phe Asp Tyr Ala Leu Val Gln Ile Asp Gly Gln Ala Val Ile
            260                 265                 270
Leu Ala Lys Asp Leu Val Glu Ser Val Met Gln Arg Ile Gly Val Thr
        275                 280                 285
Asp Tyr Thr Ile Leu Gly Thr Val Lys Gly Ala Glu Leu Glu Leu Leu
    290                 295                 300
Arg Phe Thr His Pro Phe Met Gly Phe Asp Val Pro Ala Ile Leu Gly
305                 310                 315                 320
Asp His Val Thr Leu Asp Ala Gly Thr Gly Ala Val His Thr Ala Pro
                325                 330                 335
Gly His Gly Pro Asp Asp Tyr Val Ile Gly Gln Lys Tyr Gly Leu Glu
            340                 345                 350
Thr Ala Asn Pro Val Gly Pro Asp Gly Thr Tyr Leu Pro Gly Thr Tyr
        355                 360                 365
Pro Thr Leu Asp Gly Val Asn Val Phe Lys Ala Asn Asp Ile Val Val
    370                 375                 380
Ala Leu Leu Gln Glu Lys Gly Ala Leu Leu His Val Glu Lys Met Gln
385                 390                 395                 400
His Ser Tyr Pro Cys Cys Trp Arg His Lys Thr Pro Ile Ile Phe Arg
                405                 410                 415
Ala Thr Pro Gln Trp Phe Val Ser Met Asp Gln Lys Gly Leu Arg Ala
            420                 425                 430
Gln Ser Leu Lys Glu Ile Lys Gly Val Gln Trp Ile Pro Asp Trp Gly
        435                 440                 445
```

```
Gln Ala Arg Ile Glu Ser Met Val Ala Asn Arg Pro Asp Trp Cys Ile
    450                 455                 460

Ser Arg Gln Arg Thr Trp Gly Val Pro Met Ser Leu Phe Val His Lys
465                 470                 475                 480

Asp Thr Glu Glu Leu His Pro Arg Thr Leu Glu Leu Met Glu Glu Val
                485                 490                 495

Ala Lys Arg Val Glu Val Asp Gly Ile Gln Ala Trp Trp Asp Leu Asp
            500                 505                 510

Ala Lys Glu Ile Leu Gly Asp Glu Ala Asp Gln Tyr Val Lys Val Pro
        515                 520                 525

Asp Thr Leu Asp Val Trp Phe Asp Ser Gly Ser Thr His Ser Ser Val
    530                 535                 540

Val Asp Val Arg Pro Glu Phe Ala Gly His Ala Ala Asp Met Tyr Leu
545                 550                 555                 560

Glu Gly Ser Asp Gln His Arg Gly Trp Phe Met Ser Ser Leu Met Ile
                565                 570                 575

Ser Thr Ala Met Lys Gly Lys Ala Pro Tyr Arg Gln Val Leu Thr His
            580                 585                 590

Gly Phe Thr Val Asp Gly Gln Gly Arg Lys Met Ser Lys Ser Ile Gly
        595                 600                 605

Asn Thr Val Ser Pro Gln Asp Val Met Asn Lys Leu Gly Ala Asp Ile
    610                 615                 620

Leu Arg Leu Trp Val Ala Ser Thr Asp Tyr Thr Gly Glu Met Ala Val
625                 630                 635                 640

Ser Asp Glu Ile Leu Lys Arg Ala Ala Asp Ser Tyr Arg Arg Ile Arg
                645                 650                 655

Asn Thr Ala Arg Phe Leu Leu Ala Asn Leu Asn Gly Phe Asp Pro Ala
            660                 665                 670

Lys Asp Met Val Lys Pro Glu Glu Met Val Val Leu Asp Arg Trp Ala
        675                 680                 685

Val Gly Cys Ala Lys Ala Ala Gln Glu Asp Ile Leu Lys Ala Tyr Glu
    690                 695                 700

Ala Tyr Asp Phe His Glu Val Val Gln Arg Leu Met Arg Phe Cys Ser
705                 710                 715                 720

Val Glu Met Gly Ser Phe Tyr Leu Asp Ile Ile Lys Asp Arg Gln Tyr
                725                 730                 735

Thr Ala Lys Ala Asp Ser Val Ala Arg Arg Ser Cys Gln Thr Ala Leu
            740                 745                 750

Tyr His Ile Ala Glu Ala Leu Val Arg Trp Met Ala Pro Ile Leu Ser
        755                 760                 765

Phe Thr Ala Asp Glu Val Trp Gly Tyr Leu Pro Gly Glu Arg Glu Lys
    770                 775                 780

Tyr Val Phe Thr Gly Glu Trp Tyr Glu Gly Leu Phe Gly Leu Ala Asp
785                 790                 795                 800

Ser Glu Ala Met Asn Asp Ala Phe Trp Asp Leu Leu Lys Val Arg
                805                 810                 815

Gly Glu Val Asn Lys Val Ile Glu Gln Ala Arg Ala Asp Lys Lys Val
            820                 825                 830

Gly Gly Ser Leu Glu Ala Ala Val Thr Leu Tyr Ala Glu Pro Glu Leu
        835                 840                 845

Ser Ala Lys Leu Thr Ala Leu Gly Asp Glu Leu Arg Phe Val Leu Leu
    850                 855                 860
```

```
Thr Ser Gly Ala Thr Val Ala Asp Tyr Asn Asp Ala Pro Ala Asp Ala
865                 870                 875                 880

Gln Gln Ser Glu Val Leu Lys Gly Leu Lys Val Ala Leu Ser Lys Ala
            885                 890                 895

Glu Gly Glu Lys Cys Pro Arg Cys Trp His Tyr Thr Gln Asp Val Gly
            900                 905                 910

Lys Val Ala Glu His Ala Glu Ile Cys Gly Arg Cys Val Ser Asn Val
            915                 920                 925

Ala Gly Asp Gly Glu Lys Arg Lys Phe Ala
            930                 935

<210> SEQ ID NO 9
<211> LENGTH: 505
<212> TYPE: PRT
<213> ORGANISM: Escherichia coli NBRC3992
<220> FEATURE:
<223> OTHER INFORMATION: LysRS

<400> SEQUENCE: 9

Met Ser Glu Gln His Ala Gln Gly Ala Asp Ala Val Val Asp Leu Asn
1               5                   10                  15

Asn Glu Leu Lys Thr Arg Arg Glu Lys Leu Ala Asn Leu Arg Glu Gln
            20                  25                  30

Gly Ile Ala Phe Pro Asn Asp Phe Arg Arg Asp His Thr Ser Asp Gln
        35                  40                  45

Leu His Ala Glu Phe Asp Gly Lys Glu Asn Glu Glu Leu Glu Ala Leu
    50                  55                  60

Asn Ile Glu Val Ala Val Ala Gly Arg Met Met Thr Arg Arg Ile Met
65                  70                  75                  80

Gly Lys Ala Ser Phe Val Thr Leu Gln Asp Val Gly Gly Arg Ile Gln
            85                  90                  95

Leu Tyr Val Ala Arg Asp Asp Leu Pro Glu Gly Val Tyr Asn Glu Gln
            100                 105                 110

Phe Lys Lys Trp Asp Leu Gly Asp Ile Leu Gly Ala Lys Gly Lys Leu
        115                 120                 125

Phe Lys Thr Lys Thr Gly Glu Leu Ser Ile His Cys Thr Glu Leu Arg
    130                 135                 140

Leu Leu Thr Lys Ala Leu Arg Pro Leu Pro Asp Lys Phe His Gly Leu
145                 150                 155                 160

Gln Asp Gln Glu Ala Arg Tyr Arg Gln Arg Tyr Leu Asp Leu Ile Ser
            165                 170                 175

Asn Asp Glu Ser Arg Asn Thr Phe Lys Val Arg Ser Gln Ile Leu Ser
            180                 185                 190

Gly Ile Arg Gln Phe Met Val Asn Arg Gly Phe Met Glu Val Glu Thr
        195                 200                 205

Pro Met Met Gln Val Ile Pro Gly Gly Ala Ala Ala Arg Pro Phe Ile
    210                 215                 220

Thr His His Asn Ala Leu Asp Leu Asp Met Tyr Leu Arg Ile Ala Pro
225                 230                 235                 240

Glu Leu Tyr Leu Lys Arg Leu Val Val Gly Gly Phe Glu Arg Val Phe
            245                 250                 255

Glu Ile Asn Arg Asn Phe Arg Asn Glu Gly Ile Ser Val Arg His Asn
            260                 265                 270

Pro Glu Phe Thr Met Met Glu Leu Tyr Met Ala Tyr Ala Asp Tyr Lys
        275                 280                 285
```

```
Asp Leu Ile Glu Leu Thr Glu Ser Leu Phe Arg Thr Leu Ala Gln Asp
    290                 295                 300
Ile Leu Gly Lys Thr Glu Val Thr Tyr Gly Asp Val Thr Leu Asp Phe
305                 310                 315                 320
Gly Lys Pro Phe Glu Lys Leu Thr Met Arg Glu Ala Ile Lys Lys Tyr
                325                 330                 335
Arg Pro Glu Thr Asp Met Ala Asp Leu Asp Asn Phe Asp Ser Ala Lys
                340                 345                 350
Ala Ile Ala Glu Ser Ile Gly Ile His Val Glu Lys Ser Trp Gly Leu
            355                 360                 365
Gly Arg Ile Val Thr Glu Ile Phe Glu Glu Val Ala Glu Ala His Leu
370                 375                 380
Ile Gln Pro Thr Phe Ile Thr Glu Tyr Pro Ala Glu Val Ser Pro Leu
385                 390                 395                 400
Ala Arg Arg Asn Asp Val Asn Pro Glu Ile Thr Asp Arg Phe Glu Phe
                405                 410                 415
Phe Ile Gly Gly Arg Glu Ile Gly Asn Gly Phe Ser Glu Leu Asn Asp
                420                 425                 430
Ala Glu Asp Gln Ala Gln Arg Phe Leu Asp Gln Val Ala Ala Lys Asp
            435                 440                 445
Ala Gly Asp Asp Glu Ala Met Phe Tyr Asp Glu Asp Tyr Val Thr Ala
450                 455                 460
Leu Glu His Gly Leu Pro Pro Thr Ala Gly Leu Gly Ile Gly Ile Asp
465                 470                 475                 480
Arg Met Val Met Leu Phe Thr Asn Ser His Thr Ile Arg Asp Val Ile
                485                 490                 495
Leu Phe Pro Ala Met Arg Pro Val Lys
                500                 505

<210> SEQ ID NO 10
<211> LENGTH: 424
<212> TYPE: PRT
<213> ORGANISM: Escherichia coli NBRC3992
<220> FEATURE:
<223> OTHER INFORMATION: HisRS

<400> SEQUENCE: 10

Met Ala Lys Asn Ile Gln Ala Ile Arg Gly Met Asn Asp Tyr Leu Pro
1               5                   10                  15
Gly Glu Thr Ala Ile Trp Gln Arg Ile Glu Gly Thr Leu Lys Asn Val
            20                  25                  30
Leu Gly Ser Tyr Gly Tyr Ser Glu Ile Arg Leu Pro Ile Val Glu Gln
        35                  40                  45
Thr Pro Leu Phe Lys Arg Ala Ile Gly Glu Val Thr Asp Val Val Glu
    50                  55                  60
Lys Glu Met Tyr Thr Phe Glu Asp Arg Asn Gly Asp Ser Leu Thr Leu
65                  70                  75                  80
Arg Pro Glu Gly Thr Ala Gly Cys Val Arg Ala Gly Ile Glu His Gly
                85                  90                  95
Leu Leu Tyr Asn Gln Glu Gln Arg Leu Trp Tyr Ile Gly Pro Met Phe
            100                 105                 110
Arg His Glu Arg Pro Gln Lys Gly Arg Tyr Arg Gln Phe His Gln Leu
        115                 120                 125
Gly Cys Glu Val Phe Gly Leu Gln Gly Pro Asp Ile Asp Ala Glu Leu
    130                 135                 140
```

```
Ile Met Leu Thr Ala Arg Trp Trp Arg Ala Leu Gly Ile Ser Glu His
145                 150                 155                 160

Val Thr Leu Glu Leu Asn Ser Ile Gly Ser Leu Glu Ala Arg Ala Asn
                165                 170                 175

Tyr Arg Asp Ala Leu Val Ala Phe Leu Glu Gln His Lys Glu Lys Leu
            180                 185                 190

Asp Glu Asp Cys Lys Arg Arg Met Tyr Thr Asn Pro Leu Arg Val Leu
        195                 200                 205

Asp Ser Lys Asn Pro Glu Val Gln Ala Leu Leu Asn Asp Ala Pro Ala
    210                 215                 220

Leu Gly Asp Tyr Leu Asp Glu Glu Ser Arg Glu His Phe Ala Gly Leu
225                 230                 235                 240

Cys Lys Leu Leu Glu Ser Ala Gly Ile Ala Tyr Thr Val Asn Gln Arg
                245                 250                 255

Leu Val Arg Gly Leu Asp Tyr Tyr Asn Arg Thr Val Phe Glu Trp Val
            260                 265                 270

Thr Asn Ser Leu Gly Ser Gln Gly Thr Val Cys Ala Gly Gly Arg Tyr
        275                 280                 285

Asp Gly Leu Val Glu Gln Leu Gly Gly Arg Ala Thr Pro Ala Val Gly
    290                 295                 300

Phe Ala Met Gly Leu Glu Arg Leu Val Leu Val Gln Ala Val Asn
305                 310                 315                 320

Pro Glu Phe Lys Ala Asp Pro Val Val Asp Ile Tyr Leu Val Ala Ser
                325                 330                 335

Gly Ala Asp Thr Gln Ser Ala Ala Met Ala Leu Ala Glu Arg Leu Arg
            340                 345                 350

Asp Glu Leu Pro Gly Val Lys Leu Met Thr Asn His Gly Gly Gly Asn
        355                 360                 365

Phe Lys Lys Gln Phe Ala Arg Ala Asp Lys Trp Gly Ala Arg Val Ala
    370                 375                 380

Val Val Leu Gly Glu Ser Glu Val Ala Asn Gly Thr Ala Val Val Lys
385                 390                 395                 400

Asp Leu Arg Ser Gly Glu Gln Thr Ala Val Ala Gln Asp Ser Val Ala
                405                 410                 415

Ala His Leu Arg Thr Leu Leu Gly
            420

<210> SEQ ID NO 11
<211> LENGTH: 430
<212> TYPE: PRT
<213> ORGANISM: Escherichia coli NBRC3992
<220> FEATURE:
<223> OTHER INFORMATION: SerRS

<400> SEQUENCE: 11

Met Leu Asp Pro Asn Leu Leu Arg Asn Glu Pro Asp Ala Val Ala Glu
1               5                   10                  15

Lys Leu Ala Arg Arg Gly Phe Lys Leu Asp Val Asp Lys Leu Gly Ala
            20                  25                  30

Leu Glu Glu Arg Arg Lys Val Leu Gln Val Lys Thr Glu Asn Leu Gln
        35                  40                  45

Ala Glu Arg Asn Ser Arg Ser Lys Ser Ile Gly Gln Ala Lys Ala Arg
    50                  55                  60

Gly Glu Asp Ile Glu Pro Leu Arg Leu Glu Val Asn Lys Leu Gly Glu
65                  70                  75                  80
```

```
Glu Leu Asp Ala Ala Lys Ala Glu Leu Asp Ala Leu Gln Ala Glu Ile
                85                  90                  95
Arg Asp Ile Ala Leu Thr Ile Pro Asn Leu Pro Ala Asp Glu Val Pro
            100                 105                 110
Val Gly Lys Asp Glu Asn Asp Asn Val Glu Val Ser Arg Trp Gly Thr
        115                 120                 125
Pro Arg Glu Phe Asp Phe Glu Val Arg Asp His Val Thr Leu Gly Glu
    130                 135                 140
Met His Ser Gly Leu Asp Phe Ala Ala Ala Val Lys Leu Thr Gly Ser
145                 150                 155                 160
Arg Phe Val Val Met Lys Gly Gln Ile Ala Arg Met His Arg Ala Leu
                165                 170                 175
Ser Gln Phe Met Leu Asp Leu His Thr Glu Gln His Gly Tyr Ser Glu
                180                 185                 190
Asn Tyr Val Pro Tyr Leu Val Asn Gln Asp Thr Leu Tyr Gly Thr Gly
            195                 200                 205
Gln Leu Pro Lys Phe Ala Gly Asp Leu Phe His Thr Arg Pro Leu Glu
        210                 215                 220
Glu Glu Ala Asp Thr Ser Asn Tyr Ala Leu Ile Pro Thr Ala Glu Val
225                 230                 235                 240
Pro Leu Thr Asn Leu Val Arg Gly Glu Ile Ile Asp Glu Asp Asp Leu
            245                 250                 255
Pro Ile Lys Met Thr Ala His Thr Pro Cys Phe Arg Ser Glu Ala Gly
        260                 265                 270
Ser Tyr Gly Arg Asp Thr Arg Gly Leu Ile Arg Met His Gln Phe Asp
        275                 280                 285
Lys Val Glu Met Val Gln Ile Val Arg Pro Glu Asp Ser Met Ala Ala
        290                 295                 300
Leu Glu Glu Met Thr Gly His Ala Glu Lys Val Leu Gln Leu Leu Gly
305                 310                 315                 320
Leu Pro Tyr Arg Lys Ile Ile Leu Cys Thr Gly Asp Met Gly Phe Gly
            325                 330                 335
Ala Cys Lys Thr Tyr Asp Leu Glu Val Trp Ile Pro Ala Gln Asn Thr
            340                 345                 350
Tyr Arg Glu Ile Ser Ser Cys Ser Asn Val Trp Asp Phe Gln Ala Arg
            355                 360                 365
Arg Met Gln Ala Arg Cys Arg Ser Lys Ser Asp Lys Lys Thr Arg Leu
        370                 375                 380
Val His Thr Leu Asn Gly Ser Gly Leu Ala Val Gly Arg Thr Leu Val
385                 390                 395                 400
Ala Val Met Glu Asn Tyr Gln Gln Ala Asp Gly Arg Ile Glu Val Pro
                405                 410                 415
Glu Val Leu Arg Pro Tyr Met Asn Gly Leu Glu Tyr Ile Gly
            420                 425                 430
```